US007004976B2

(12) United States Patent
Ornberg et al.

(10) Patent No.: US 7,004,976 B2
(45) Date of Patent: Feb. 28, 2006

(54) BIOPOLYMERS MODIFIED WITH SUPEROXIDE DISMUTASE MIMICS

(75) Inventors: Richard L. Ornberg, Wildwood, MO (US); Kishore Udipi, San Rosa, CA (US); Denis Forster, Ladue, MO (US); Dennis P. Riley, Chesterfield, MO (US); Kenneth B. Thurmond, Plano, TX (US); Susan Henke, Webster Groves, MO (US); Kerry Brethaur, Belleville, IL (US); Saikat Joardar, Ballwin, MO (US)

(73) Assignee: Pharmacia Corporation, St. Louis, MO (US)

( * ) Notice: Subject to any disclaimer, the term of this patent is extended or adjusted under 35 U.S.C. 154(b) by 44 days.

(21) Appl. No.: 10/702,407

(22) Filed: Nov. 5, 2003

(65) Prior Publication Data

US 2004/0116332 A1 Jun. 17, 2004

Related U.S. Application Data

(63) Continuation of application No. 09/580,007, filed on May 26, 2000.

(60) Provisional application No. 60/136,298, filed on May 27, 1999.

(51) Int. Cl.
  *A61F 2/02* (2006.01)
  *A61K 31/715* (2006.01)
  *C08G 37/08* (2006.01)
(52) U.S. Cl. .................. 623/23.58; 514/54; 536/20
(58) Field of Classification Search ............... 623/11.1, 623/23.58, 902; 514/55–57, 6; 530/400; 536/20, 31, 53
See application file for complete search history.

(56) References Cited

U.S. PATENT DOCUMENTS

| 4,514,589 A | 4/1985 | Aldinger et al. ............ 174/119 |
|---|---|---|
| 4,718,908 A | 1/1988 | Wigginton et al. ........... 623/16 |
| 4,775,426 A | 10/1988 | Murley et al. .................. 148/2 |
| 5,013,323 A | 5/1991 | Kobayashi et al. ........... 623/16 |
| 5,386,012 A | 1/1995 | Strid .......................... 530/331 |
| 5,397,362 A | 3/1995 | Noda .......................... 623/16 |
| 5,403,834 A | 4/1995 | Malfroy-Camine et al. . 514/185 |
| 5,525,621 A | 6/1996 | Burt et al. .................... 514/393 |
| 5,610,293 A | 3/1997 | Riley et al. .................. 540/474 |
| 5,626,861 A | 5/1997 | Laurencin et al. .......... 540/426 |
| 5,626,863 A | 5/1997 | Hubbell et al. ............. 424/426 |
| 5,637,578 A | 6/1997 | Riley et al. .................. 514/186 |
| 5,665,428 A | 9/1997 | Cha et al. ................. 427/213.3 |
| 5,696,109 A | 12/1997 | Malfroy-Camine et al. . 514/185 |

(Continued)

FOREIGN PATENT DOCUMENTS

CN  1088069  6/1994

(Continued)

OTHER PUBLICATIONS

Alexander et al. (1970). *Inorg. Nucl. Chem. Lett.* 6: 445-448.

(Continued)

*Primary Examiner*—David J. Isabella
(74) *Attorney, Agent, or Firm*—Mintz, Levin, Cohn, Ferris, Glovsky and Popeo, P.C.; Ivor R. Elrifi; Heidi A. Erlacher

(57) ABSTRACT

This invention provides modified biopolymers comprising biopolymers attached to at least one non-proteinaceous catalyst capable of dismutating superoxide in the biological system or precursor ligand thereof. The invention further provides pharmaceutical compositions comprising the modified biopolymer and therapeutic methods comprising administering the modified biopolymer to a subject in need thereof.

6 Claims, 13 Drawing Sheets

Figure 1:
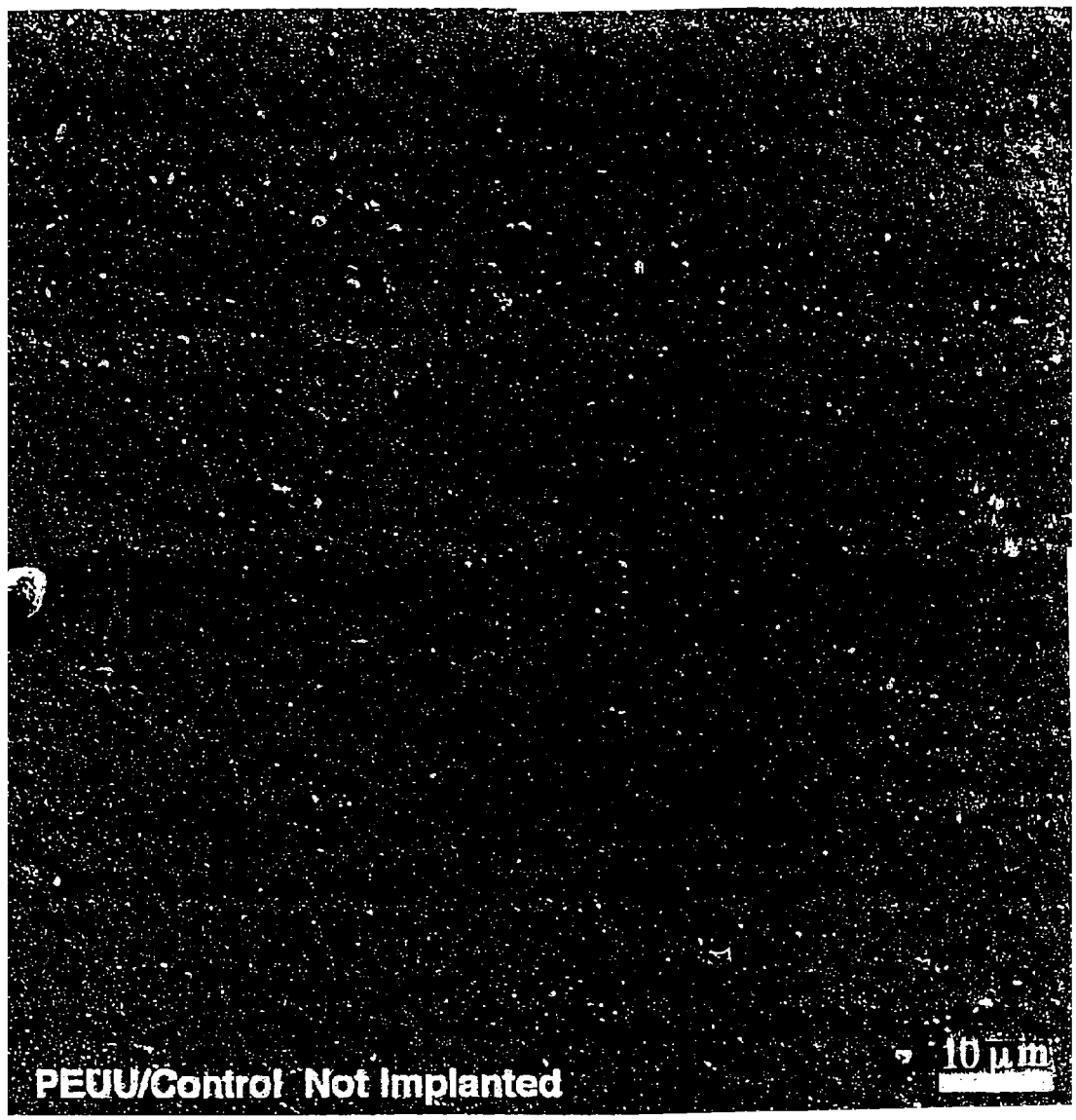

SODm - Polyurethane Implants at Day 28.

Capsule tissue next to Implant. Bar = 20 um.

A. Control; Foreign body giant cells, FBGCs, lie next to implant (arrow). Implant capsule consists of layered fibroblast and matrix.
B. Low dose SODm; FBGCs are reduced. Capsule of layered fibroblasts and matrix has thickness similar to control.
C. High dose SODm; FBGCs are reduced but observed. Implant capsule thickness is less than control.

U.S. PATENT DOCUMENTS

| | | | |
|---|---|---|---|
| 5,711,763 A | 1/1998 | Nonami et al. | 623/16 |
| 5,749,839 A | 5/1998 | Kovacs | 601/153 |
| 5,766,618 A | 6/1998 | Laurencin et al. | 424/426 |
| 5,800,456 A | 9/1998 | Maeda et al. | 606/198 |
| 5,817,303 A | 10/1998 | Stedronsky et al. | 424/78.02 |
| 5,824,047 A | 10/1998 | Moreland | 623/1 |
| 5,827,880 A | 10/1998 | Malfroy-Camine et al. | 514/492 |
| 5,830,539 A | 11/1998 | Yan et al. | 427/551 |
| 5,834,509 A | 11/1998 | Malfroy-Camine et al. | 514/492 |
| 5,836,313 A | 11/1998 | Perez et al. | 128/898 |
| 5,837,752 A * | 11/1998 | Shastri et al. | 523/116 |
| 5,840,319 A | 11/1998 | Alakhov et al. | 424/400 |
| 5,851,227 A | 12/1998 | Spehr | 607/126 |
| 5,861,032 A | 1/1999 | Subramaniam | 623/11 |
| 5,869,103 A | 2/1999 | Yeh et al. | 424/501 |
| 5,871,535 A | 2/1999 | Wolff et al. | 623/1 |
| 5,873,904 A | 2/1999 | Ragheb et al. | 623/1 |
| 5,874,421 A | 2/1999 | Riley et al. | 514/161 |
| 5,876,433 A | 3/1999 | Lunn | 623/1 |
| 5,876,452 A | 3/1999 | Athanasiou et al. | 623/16 |
| 5,877,263 A | 3/1999 | Patnaik et al. | 525/453 |
| 5,879,359 A | 3/1999 | Dorigatti et al. | 606/152 |
| 5,879,697 A | 3/1999 | Ding et al. | 424/422 |
| 5,885,609 A | 3/1999 | Amiji | 424/425 |
| 5,889,130 A | 3/1999 | Worley et al. | 526/261 |
| 5,891,862 A | 4/1999 | Mandeville, III et al. | 514/54 |
| 6,323,218 B1 | 11/2001 | Bush et al. | 514/311 |
| 6,506,411 B1 | 1/2003 | Hunter et al. | 424/501 |
| 6,774,278 B1 * | 8/2004 | Ragheb et al. | 623/1.1 |
| 2003/0232784 A1 | 12/2003 | Benedict | 514/54 |

FOREIGN PATENT DOCUMENTS

| | | |
|---|---|---|
| EP | 0 524 161 | 1/1993 |
| EP | 0 598 753 | 6/1994 |
| EP | 0 679 155 | 11/1995 |
| WO | WO 93/11800 | 6/1993 |
| WO | WO 93/14093 | 7/1993 |
| WO | WO 95/28968 | 11/1995 |
| WO | WO 96/39396 | 12/1996 |
| WO | WO 96/40658 | 12/1996 |
| WO | WO 98/58636 | 12/1998 |

OTHER PUBLICATIONS

Aston et al. (1994). *Tetrahedron Lett.* 35: 3687-3690.
Babior, B. (1997). *Brazilian J. Med. Biol. Res.* 30: 141-155.
Bannister et al. (1987). *CRC Critical Reviews in Biochem.* 22: 111-180.
Black et al. (1994). *J. Pharmacol. and Exp. Therapeutics* 270: 1208-1215.
Borowiec et al. (1997). *Thorac. Cardiovasc. Surgeon* 45: 295-301.
Bradshaw et al. (1989). *J. Heterocyclic Chem.* 26: 1431-1435.
Brady et al. (1979). *J. Org. Chem.* 44: 3101-3105.
Bulkley, G. (1994). *The Lancet* 344: 934-936.
Cremer et al. (1989). *J. Heart Transplantation* 8: 330-336.
Cundiff and Markunas (1961). *Anal. Chem.* 33: 1028-1030.
Ferrari et al. (1989). *Pharmacological Res.* 21: 57-65.
Gristina, A. (1994). *Clinical Orthopaedics & Related Res.* 298: 106-118.
Gryglewski et al. (1986). *Nature 320*: 454-456.
Hardy et al. (1994). *J. Biol. Chem.* 269: 18535-18540.
Kaplan et al. (1992). *J. Biomedical Mat. Res.* 26: 1039-1051.
Kasten et al. (1995). *Proc. Soc. Exp. Biol. Med.* 208: 170-177.
Kilgore et al. (1994). *J. Mol. Cell Cardiol.* 26: 995-1006.
Kimura et al. (1981). *Biochimica et Biophysica Acta* 678: 172-179.
Krakowiak et al. (1990). *J. Org. Chem.* 55: 3364-3368.
Lin et al. (1994). *Int. J. Oral Maxillofac. Surg.* 23: 428-429.
Lindoy, L. In *The Chemistry of Macrocyclic Ligand Complexes*, The Press Syndicate of the University of Cambridge, 1989, pp. 16, 40-42.
Michelson, A.M., In *Handbook of Methods for Oxygen Radical Research*, Greenwald, R.A., Ed.; CRC Boca Raton, 1982, pp. 71-75.
Moore et al. (1997). *J. Biomedical Mat. Res.* 34: 137-147.
Newton and Jackels (1988). *J. Coord. Chem.* 19: 265-277.
Park et al. (1991). *J. Polymer Sci.* 20: 1725-1737.
Richman et al. (1974). *J. Am. Chem. Soc.* 96: 7-9.
Riley and Weiss (1997). *Cat. Tech.* I pp. 41-49.
Riley et al. (1991). *Anal. Biochem.* 196: 344-349.
Riley et al. (1999). *Inorg. Chem.* 38: 1908-1917.
Ross et al. (1996). *Bio. Sci. Inst.* 32: 71-79.
Shanbhag et al. (1992). *J. Biomedical Mat. Res.* 26: 185-195.
Siggia et al. "Quantitative Organic Analysis Via Functional Groups", 4th Ed., John Wiley & Sons, pp. 169-172.
Venturini et al. "A Manganese Based Superoxide Dismutase Mimic Protects Feline Myocardium for Necrosis After Ischemia and Reperfusion." In *The Biology of Nitric Oxide*, Portland Press, London, 1994, 65-69.
Weiss and Riley (1996). *Drugs of the Future* 21: 383-389.
Weiss et al. (1991). *J. Cell. Biochem. Suppl.* 15C: 216, Abstract No. CC110.
Weiss et al. In *The Oxygen Paradox*, CLEUP University Press, Padova, Italy, 1995, pp. 641-651.
Weiss et al. (1996). *J. Biol. Chem.* 271: 26149-26156.
Weiss and Riley "Therapuetic Aspects of Manganese (II)-Based Superoxide Dismutase Mimics" In *Inorganic Chemistry in Medicine*, Farrell, N. Ed., Royal Society of Chemistry, 1999, Ch. 5.

* cited by examiner

FIG. 4
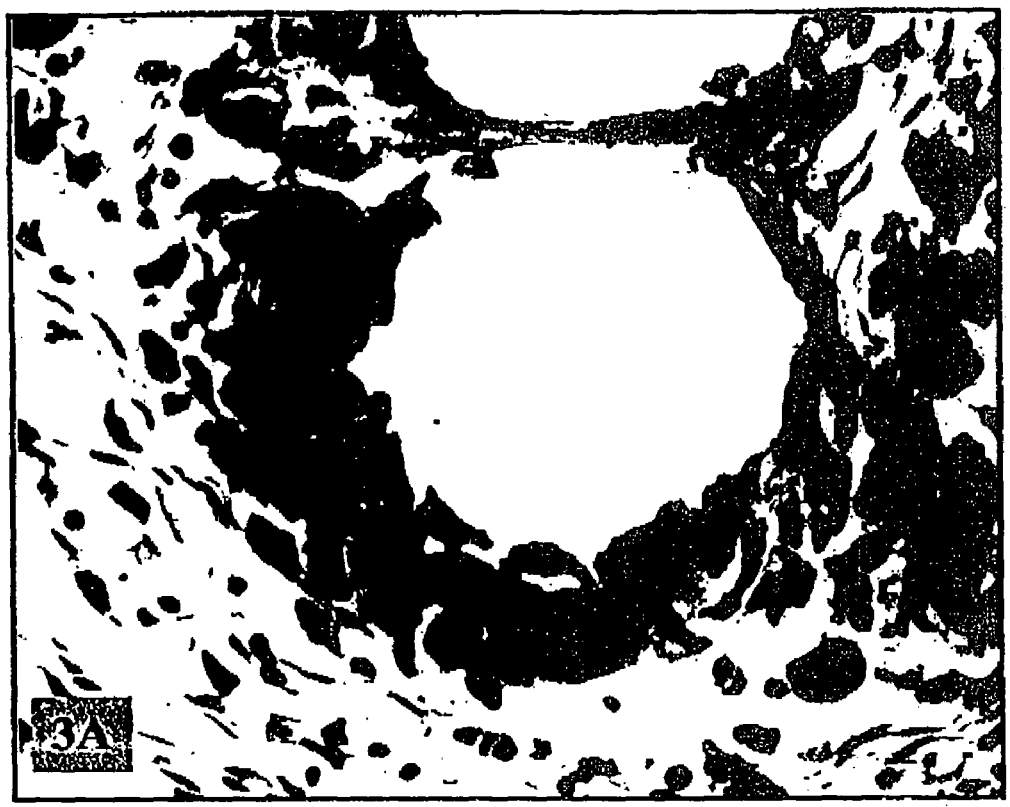
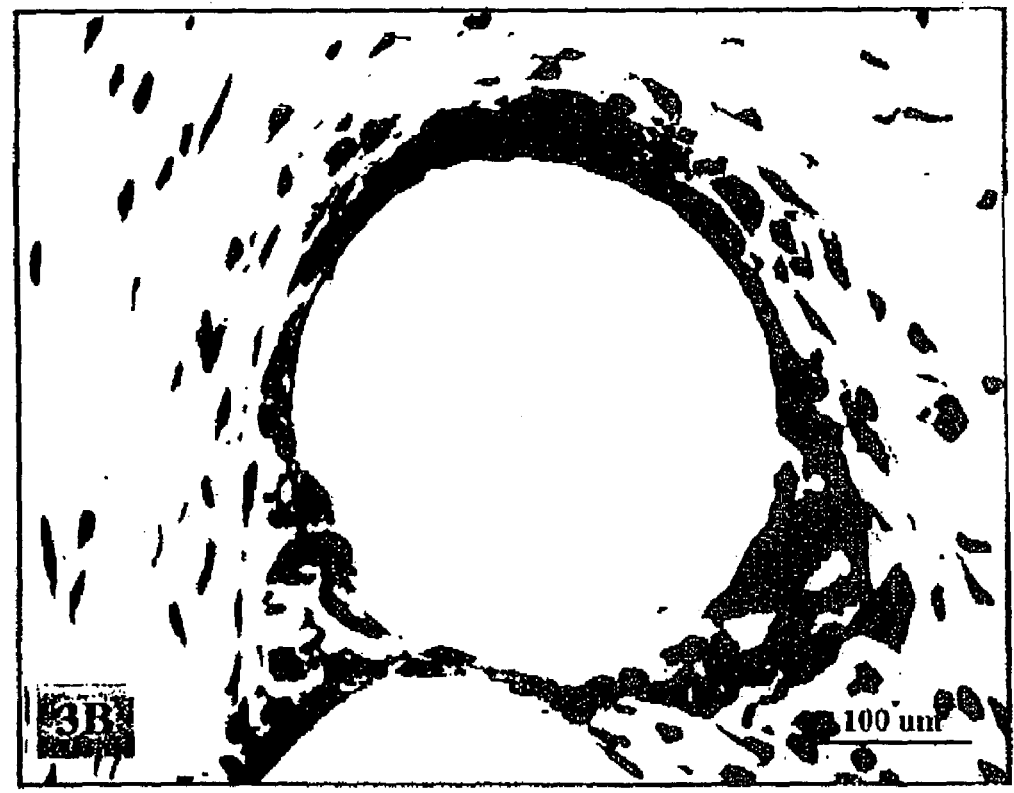

FIG. 5 SODm – Polyethylene Implants at Day 3.

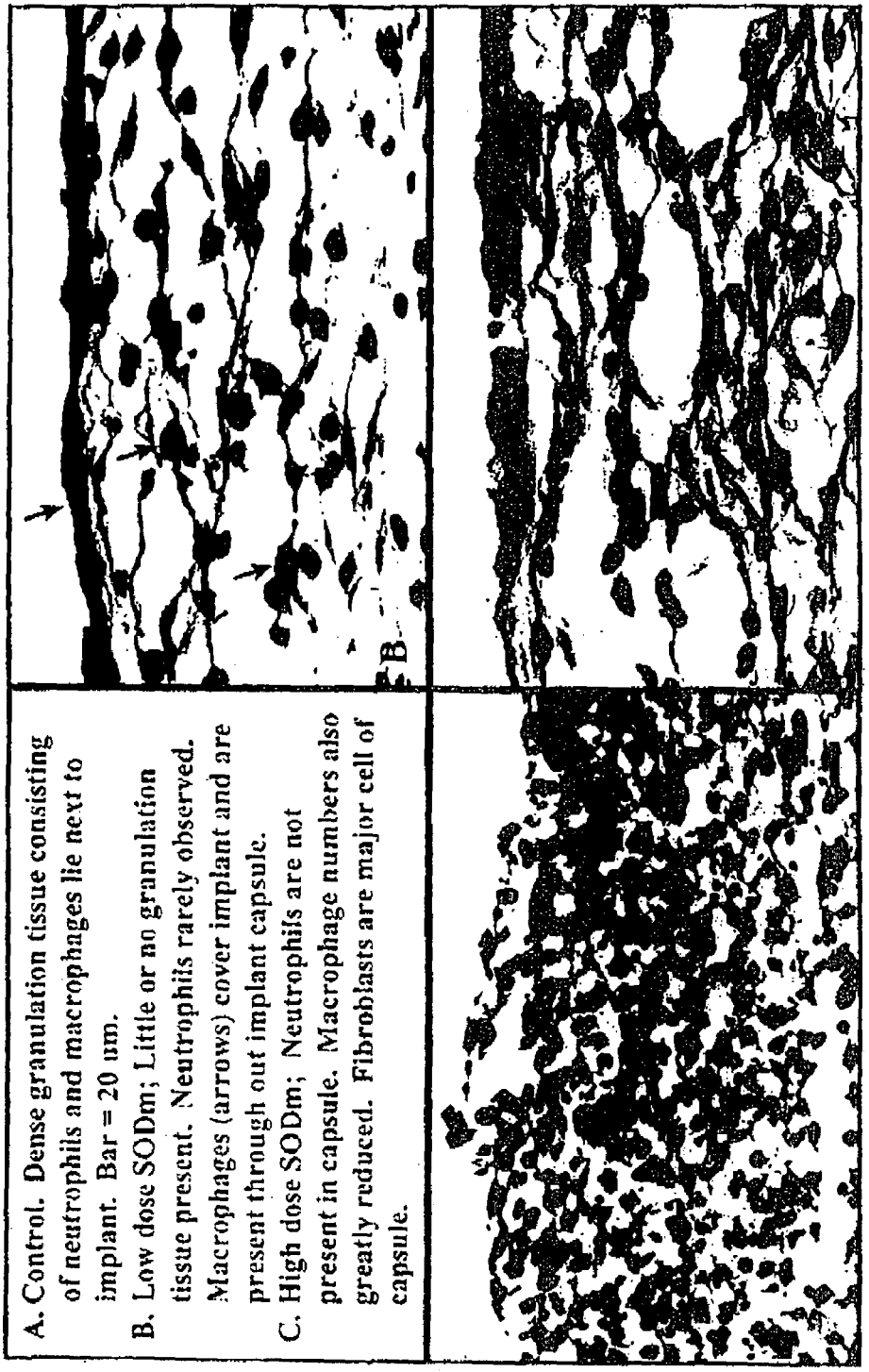

A. Control. Dense granulation tissue consisting of neutrophils and macrophages lie next to implant. Bar = 20 um.
B. Low dose SODm; Little or no granulation tissue present. Neutrophils rarely observed. Macrophages (arrows) cover implant and are present through out implant capsule.
C. High dose SODm; Neutrophils are not present in capsule. Macrophage numbers also greatly reduced. Fibroblasts are major cell of capsule.

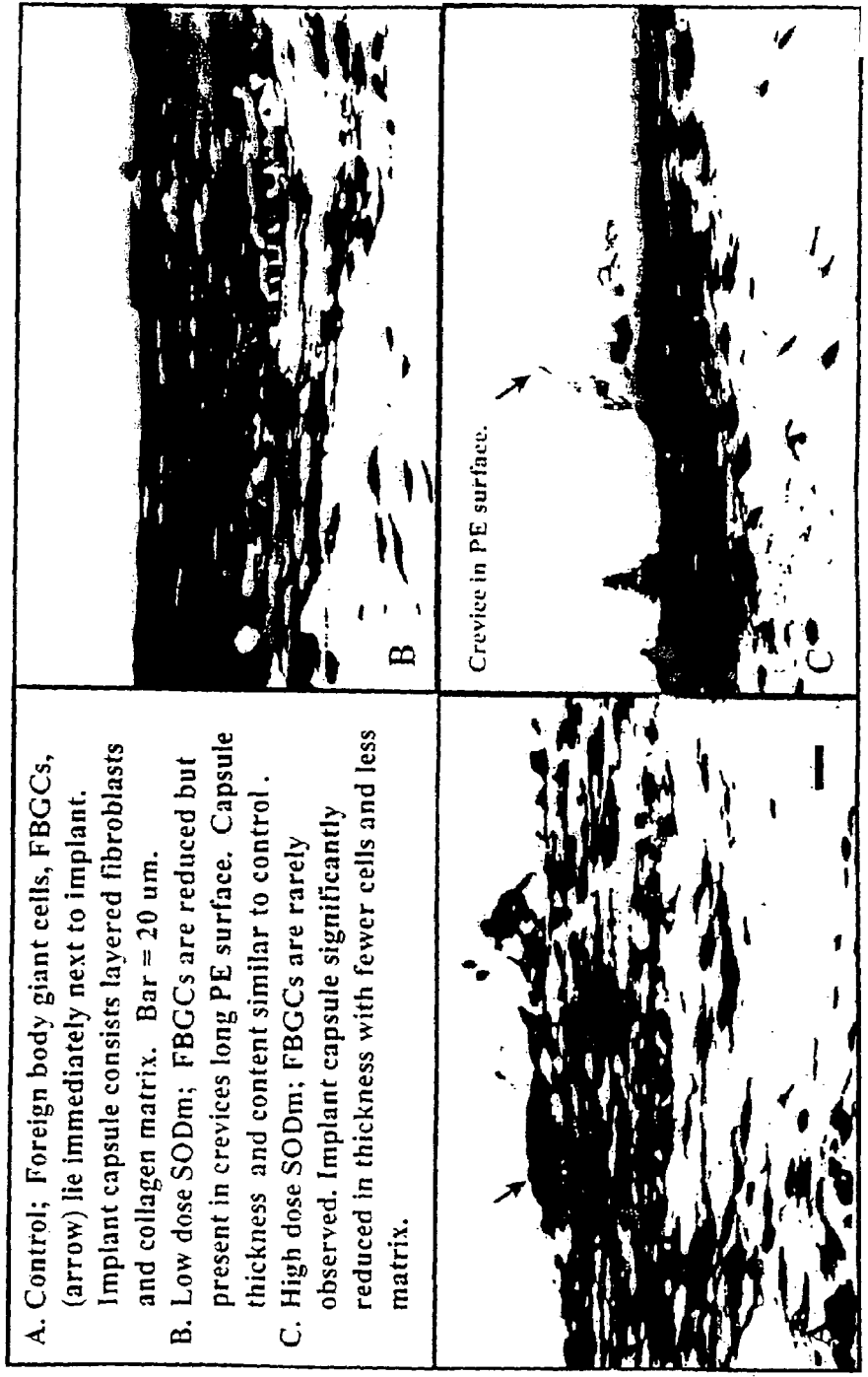
FIG. 6 SODm - Polyethylene Implants at Day 28.

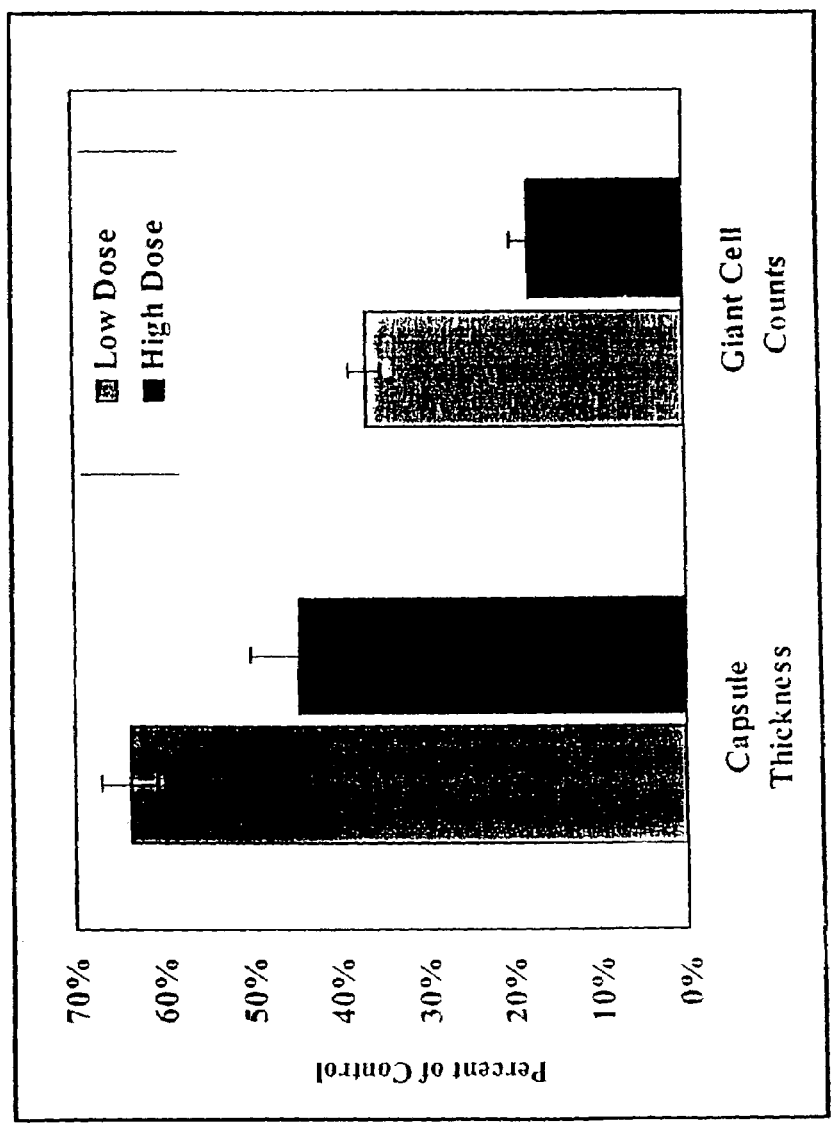
FIG. 7 Effect of SODm on Chronic Inflammation; Foreign Body Giant Cells and Capsule Thickness; Day 28

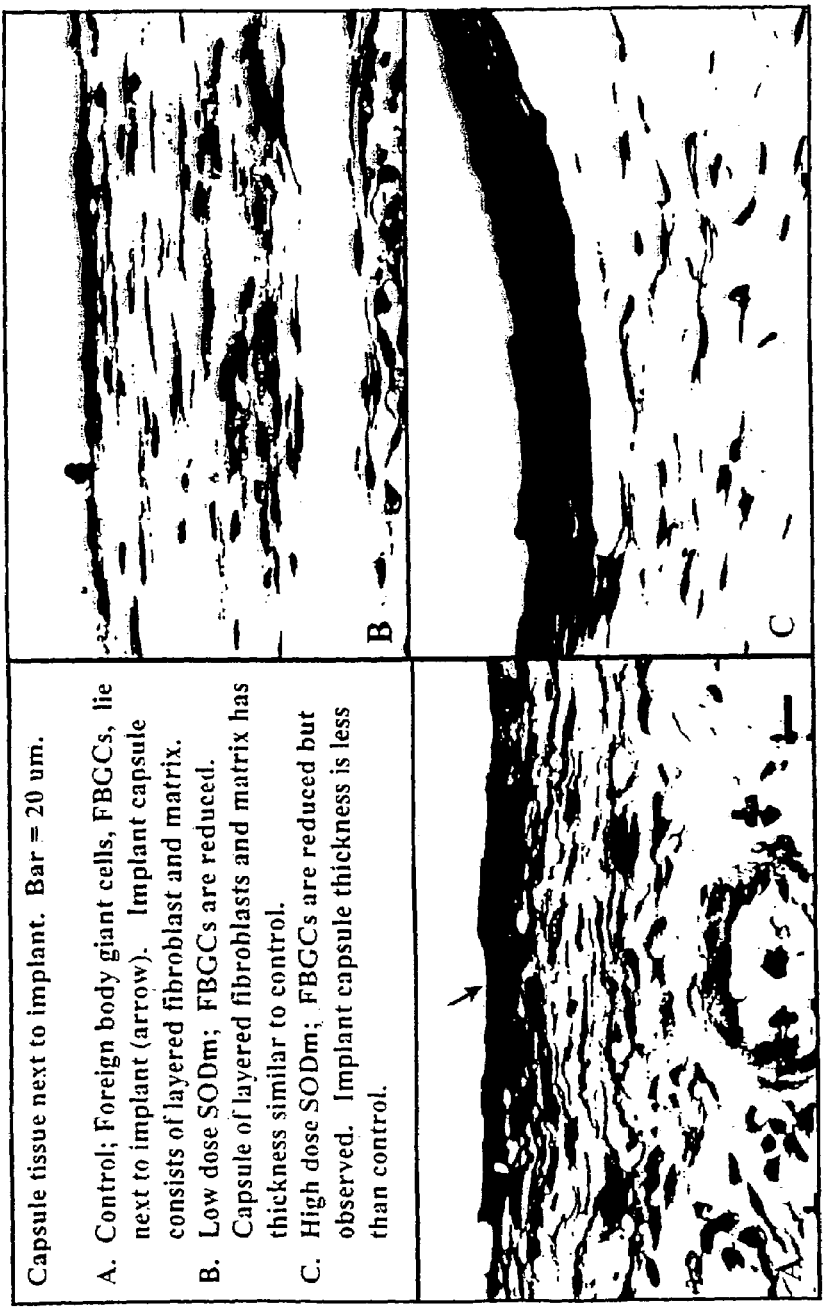

FIG. 8
SODm - Polyurethane Implants at Day 28.

Capsule tissue next to implant. Bar = 20 um.

A. Control; Foreign body giant cells, FBGCs, lie next to implant (arrow). Implant capsule consists of layered fibroblast and matrix.
B. Low dose SODm; FBGCs are reduced. Capsule of layered fibroblasts and matrix has thickness similar to control.
C. High dose SODm; FBGCs are reduced but observed. Implant capsule thickness is less than control.

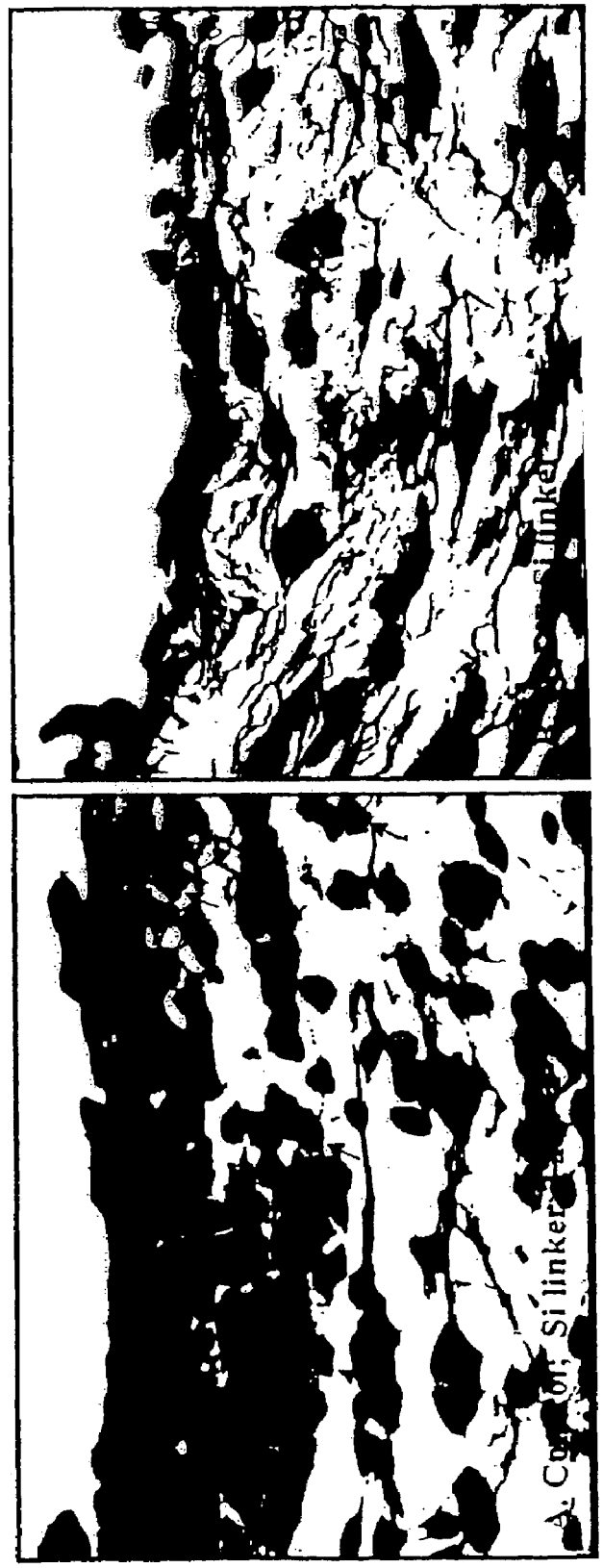
FIG. 9 SODm-Tantalum Implant at 3 days

SODm -Tantalum Implant at 28 days

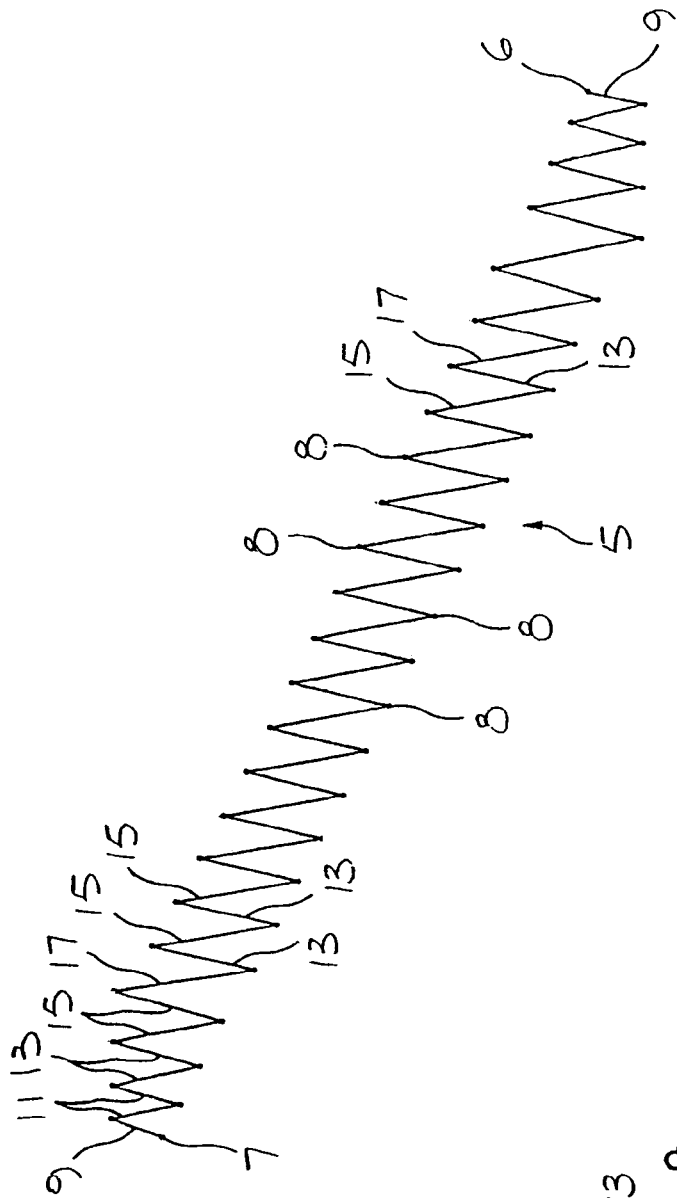

BIOPOLYMERS MODIFIED WITH SUPEROXIDE DISMUTASE MIMICS

CROSS-REFERENCE TO RELATED APPLICATIONS

This application is a continuation of U.S. Ser. No. 09/580,007, filed May 26, 2000, which claims priority from provisional application No. 60/136,298 filed May 27, 1999, which are hereby incorporated by reference in their entirety for all purposes.

BACKGROUND OF THE INVENTION

The present invention relates to biomaterials modified with non-proteinaceous catalysts for the dismutation of superoxide, and processes for making such materials. This modification may be by covalent conjugation, copolymerization, or admixture of the non-proteinaceous catalysts with the biomaterial. The resulting modified biomaterials exhibit a marked decrease in inflammatory response and subsequent degradation when placed in contact with vertebrate biological systems.

"Biomaterial" is a term given to a wide variety of materials which are generally considered appropriate for use in biological systems, including metals, polymers, biopolymers, and ceramics. Also included in the term are composites of such materials, such as the polymer-hydroxyapatite composite disclosed in U.S. Pat. No. 5,626,863. Biomaterials are used in a variety of medical and scientific applications where a man-made implement comes into contact with living tissue. Heart valves, stents, replacement joints, screws, pacemaker leads, blood vessel grafts, sutures and other implanted devices constitute one major use of biomaterials. Machines which handle bodily fluids for return to the patient, such as heart/lung and hemodialysis machines, are another significant use for biomaterials.

Common metal alloy biomaterials used for implants include titanium alloys, cobalt-chromium-molybdenum alloys, cobalt-chromium-tungsten-nickel alloys and non-magnetic stainless steels (300 series stainless steel). See U.S. Pat. No. 4,775,426. Titanium alloys are frequently used for implants because they have excellent corrosion resistance. However, they have inferior wear characteristics when compared with either cobalt-chromium-molybdenum alloys or 300 series stainless steel. Cobalt-chromium-molybdenum alloys have about the same tensile strength as the titanium alloys, but are generally less corrosion resistant. They also have the further disadvantage of being difficult to work. In contrast, the 300 series stainless steels were developed to provide high-strength properties while maintaining workability. These steels are, however, even less resistant to corrosion and hence more susceptible to corrosion fatigue. See U.S. Pat. No. 4,718,908. Additional examples of biocompatible metals and alloys include tantalum, gold, platinum, iridium, silver, molybdenum, tungsten, inconel and nitinol. Because certain types of implants (artificial joints, artificial bones or artificial tooth roots) require high strength, metallic biomaterials have conventionally been used. However, as mentioned above, certain alloys corrode within the body and, as a result, dissolved metallic ions can produce adverse effects on the surrounding cells and can result in implant breakage.

In an attempt to solve this problem, ceramic biomaterials such as alumina have been used in high-stress applications such as in artificial knee joints. Ceramic biomaterials have an excellent affinity for bone tissue and generally do not corrode in the body. But when used under the load of walking or the like, they may not remain fixed to the bone. In many cases additional surgery is required to secure the loosened implant. This shortcoming led to the development of bioactive ceramic materials. Bioactive ceramics such as hydroxyapatite and tricalcium phosphate are composed of calcium and phosphate ions (the main constituents of bone) and are readily resorbed by bone tissue to become chemically united with the bone. U.S. Pat. No. 5,397,362. However, bioactive ceramics such as hydroxyapatite and tricalcium phosphate are relatively brittle and can fail under the loads in the human body. This has led in turn to the development of non-calcium phosphate bioactive ceramics with high strength. See U.S. Pat. No. 5,711,763. Additional examples of biocompatible ceramics include zirconia, silica, calcia, magnesia, and titania series materials, as well as the carbide series materials and the nitride series materials.

Polymeric biomaterials are desirable for implants because of their chemical inertness and low friction properties. However, polymers used in orthopedic devices such as hip and knee joints have a tendency for wear and build-up of fine debris, resulting in a painful inflammatory response. Examples of biocompatible polymeric materials include silicone, polyurethane, polyureaurethane, polyethylene terphthalate, ultra high molecular weight polyethylene, polypropylene, polyester, polyamide, polycarbonate, polyorthoesters, polyesteramides, polysiloxane, polyolefin, polytetrafluoroethylene, polysulfones, polyanhydrides, polyalkylene oxide, polyvinyl halide, polyvinyledene halide, acrylic, methacrylic, polyacrylonitrile, vinyl, polyphosphazene, polyethylene-co-acrylic acid, hydrogels and copolymers. Specific applications include the use of polyethylene in hip and knee joint implants and the use of hydrogels in ocular implants. See U.S. Pat. No. 5,836,313. In addition to relatively inert polymeric materials discussed above, certain medical applications require the use of biodegradable polymers for use as sutures and pins for fracture fixation. These materials serve as a temporary scaffold which is replaced by host tissue as they are degraded. See U.S. Pat. No. 5,766,618. Examples of such biodegradable polymers include polylactic acid, polyglycolic acid, and polyparadioxanone.

In addition to wholly synthetic polymers, polymers which are naturally produced by organisms have been used in several medical applications. Such polymers, including polysaccharides such as chitin, cellulose and hyaluronic acid, and proteins such as fibroin, keratin, and collagen, offer unique physical properties in the biological environment, and are also useful when a biodegradable polymer is required. In order to adapt these polymers for certain uses, many have been chemically modified, such as chitosan and methyl cellulose. These polymers have found niches in a variety of applications. Chitosan is often used to cast semipermeable films, such as the dialysis membranes in U.S. Pat. No. 5,885,609. Fibroin (silk protein) has been used as a support member in tissue adhesive compositions, U.S. Pat. No. 5,817,303. Also, esters of hyaluronic acid have been used to create bioabsorbable scaffolding for the regrowth of nerve tissue, U.S. Pat. No. 5,879,359.

As is evident from the preceding paragraphs, individual biomaterials have both desirable and undesirable characteristics. Thus, it is common to create medical devices which are composites of various biocompatible materials in order to overcome these deficiencies. Examples of such composite materials include: the implant material comprising glass fiber and polymer material disclosed in U.S. Pat. No. 5,013,323; the polymeric-hydroxyapatite bone composite disclosed in U.S. Pat. No. 5,766,618; the implant comprising a ceramic substrate, a thin layer of glass on the substrate and a layer of calcium phosphate over the glass disclosed in U.S. Pat. No. 5,397,362; and an implant material comprising carbon fibers in a matrix of fused polymeric microparticles. The diverse uses of biomaterials require a range of mechanical and physical properties for particular applications. As medical science advances, many applications will require new and diverse materials which can be safely and effectively used in biological systems.

Biomaterials, especially polymers, have been chemically modified in several ways in order to give them certain biological characteristics. For instance, thrombogenesis has posed a perennial problem for the use of biomaterials in hemodialysis membranes. In order to decrease thrombogenesis, hemodialysis fluid circuit materials have been modified by ionic complexation and interpenetration of heparin, U.S. Pat. No. 5,885,609, and by graft copolymer techniques in which heparin is linked to the backbone polymer by polyethylene oxide, Park, K. D., "Synthesis and Characterization of SPUU-PEO-Heparain Graft Copolymers", J. Polymer. Sci., Vol. 20, p. 1725–37 (1991). Similarly, polymers containing incorporated drugs for elution into the body have been co-implanted with stents in order to prevent restenosis, U.S. Pat. No. 5,871,535.

Although most biomaterials in current use are considered non-toxic, implanted biomaterial devices are seen as foreign bodies by the immune system, and so elicit a well characterized inflammatory response. See Gristina, A. G. "Implant Failure and the Immuno-Incompetent Fibro-Inflammatory Zone" In "Clinical Orthopaedics and Related Research" (1994), No. 298, pp. 106–118. This response is evidenced by the increased activity of macrophages, granulocytes, and neutrophils, which attempt to remove the foreign object by the secretion of degradative enzymes and free radicals like superoxide ion ($O_2^-$) to inactivate or decompose the foreign object. Woven dacron polyester, polyurethane, velcro, polyethylene, and polystyrene were shown to elicit superoxide production from neutrophils by Kaplan, S. S., et al, "Biomaterial-induced alterations of neutrophil superoxide production" In "Jour.Bio.Mat.Res." (1992), Vol. 26, pp. 1039–1051. To a lesser extent, polysulfone/carbon fiber and polyetherketoneketone/carbon fiber composites were shown to elicit a superoxide response by Moore, R., et al, "A comparison of the inflammatory potential of particulates derived from two composite materials" In "Jour.Bio.Mat.Res." (1997), Vol. 34, pp. 137–147. Hydroxyapatite, tricalcium phosphate, and aluminum-calcium-phosphorous oxide bioceramics were shown to be degraded by macrophages by Ross, L., et al, "The Effect of HA, TCP and Alcap Bioceramic Capsules on the Viability of Human Monocyte and Monocyte Derived Macrophages" in "Bio.Sci.Inst." (1996), Vol. 32, pp. 71–79. Similarly, cobalt-chrome alloy beads were degraded by neutrophils in a study by Shanbhag, A., et al, "Decreased neutrophil respiratory burst on exposure to cobalt-chrome alloy and polystyrene in vitro" In "Jour.Bio.Mat.Res." (1992), Vol. 26, 2, pp. 185–195. Even biomaterials which have been modified to present biologically acceptable molecules, such as heparin, have been found to elicit an inflammatory response, Borowiec, J. W., et al, "Biomaterial-Dependent Blood Activation During Simulated Extracorporeal Circulation: a Study of Heparin-Coated and Uncoated Circuits", Thorac. Cardiovasc. Surgeon 45 (1997) 295–301. In addition, chemical modification has posed several difficulties. Because of the unique chemical characteristics of each biomaterial and bioactive molecule, covalent linkage of the desired bioactive molecule to the biomaterial is not always possible. In addition, the activity of many bioactive molecules, especially proteins, is diminished or extinguished when anchored to a solid substrate. Finally, the fact that many biologically active substances are heat liable has prevented their use with biomaterials that are molded or worked at high temperatures.

The impact of continual attempts by the organism to degrade biomaterial implants can lead to increased morbidity and device failure. In the case of polyurethane pacemaker lead wire coatings, this results in polymer degradation and steady loss of function. In the use of synthetic vascular grafts, this results in persistent thrombosis, improper healing, and restenosis. As mentioned above, orthopedic devices such as hip and knee joints have a tendency for wear and build-up of fine debris resulting in a painful inflammatory response. In addition, the surrounding tissue does not properly heal and integrate into the prosthetic device, leading to device loosening and opportunistic bacterial infections. It has been proposed by many researchers that chronic inflammation at the site of implantation leads to the exhaustion of the macrophages and neutrophils, and an inability to fight off infection.

Superoxide anions are normally removed in biological systems by the formation of hydrogen peroxide and oxygen in the following reaction (hereinafter referred to as dismutation):

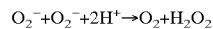

$$O_2^- + O_2^- + 2H^+ \rightarrow O_2 + H_2O_2$$

This reaction is catalyzed in vivo by the ubiquitous superoxide dismutase enzyme. Several non-proteinaceous catalysts which mimic this superoxide dismutating activity have been discovered. A particularly effective family of non-proteinaceous catalysts for the dismutation of superoxide consists of the manganese(II), manganese(III), iron(II) or iron(III) complexes of nitrogen-containing fifteen-membered macrocyclic ligands which catalyze the conversion of superoxide into oxygen and hydrogen peroxide, described in U.S. Pat. Nos. 5,874,421 and 5,637,578, all of which are incorporated herein by reference. See also Weiss, R. H., et al, "Manganese(II)-Based Superoxide Dismutase Mimetics: Rational Drug Design of Artificial Enzymes", (1996) Drugs of the Future 21, 383–389; and Riley, D. P., et al, "Rational Design of Synthetic Enzymes and Their Potential Utility as Human Pharmaceuticals" (1997) in CatTech, I, 41. These mimics of superoxide dismutase have been shown to have a variety of therapeutic effects, including anti-inflammatory activity. See Weiss, R. H., et al, "Therapeutic Aspects of Manganese (II)-Based Superoxide Dismutase Mimics" In "Inorganic Chemistry in Medicine", (Farrell, N., Ed.), Royal Society of Chemistry, in Press; Weiss, R. H., et al, "Manganese-Based Superoxide Dismutase Mimics: Design, Discovery and Pharmacologic Efficacies" (1995) In "The Oxygen Paradox (Davies, K. J. A., and Ursini, F., Eds.) pp. 641–651, CLEUP University Press, Padova, Italy; Weiss, R. H., et al, "Manganese-Based Superoxide Dismutase Mimetic Inhibit Neutrophil Infiltration In Vitro", J.Biol.Chem., 271, 26149 (1996); and Hardy, M. M., et al, "Superoxide Dismutase Mimetics Inhibit Neutrophil-Mediated Human Aortic Endothelial Cell Injury In Vitro", (1994) J.Biol.Chem. 269, 18535–18540. Other non-proteinaceous catalysts which have been shown to have superoxide dismutating activity are the salen-transition metal cation complexes, described in U.S. Pat. No. 5,696,109, and complexes of porphyrins with iron and manganese cations.

SUMMARY OF THE INVENTION

Applicants have discovered that the modification of biomaterials with non-proteinaceous catalysts for the dismutation of superoxide greatly improves the biomaterial's resistance to degradation and reduces the inflammatory response. Thus, the present invention is directed to biomaterials which have been modified with non-proteinaceous catalysts for the dismutation of superoxide, or precursor ligands of non-proteinaceous catalysts for the dismutation of superoxide.

The present invention is directed to biomaterials which have been modified with non-proteinaceous catalysts for the dismutation of superoxide, or precursor ligands of a non-proteinaceous catalyst for the dismutation of superoxide, by utilizing methods of physical association, such as surface covalent conjugation, copolymerization, and physical admixing. The present invention is also directed to biomaterials modified with non-proteinaceous catalysts for the dismutation of superoxide wherein one or more of these methods has been used to modify the biomaterial.

A variety of biomaterials are appropriate for modification in the present invention. Because the non-proteinaceous catalysts for the dismutation of superoxide are suitable for use in a range of methods for physically associating the catalyst with the biomaterial, almost any biomaterial may be modified according to the present invention. The biomaterial to be modified may be any biologically compatible metal, ceramic, polymer, biopolymer, biologically derived material, or a composite thereof. Thus, the present invention is further directed towards any of the above biomaterials modified with non-proteinaceous catalysts for the dismutation of superoxide.

As previously mentioned, the non-proteinaceous catalysts for the dismutation of superoxide for use in the present invention comprise an organic ligand and a transition metal cation. Particularly preferred catalysts are manganese and iron chelates of pentaazacyclopentadecane compounds (hereinafter referred to as "PACPeD catalysts"). Also suitable for use in the present invention are the salen complexes of manganese and iron disclosed in U.S. Pat. No. 5,696,109, and iron or manganese porphyrins, such as $Mn^{III}$ tetrakis(4-N-methylpyridyl)porphyrin, $Mn^{III}$ tetrakis-o-(4-N-methylisonicotinamidophenyl)porphyrin, $Mn^{III}$ tetrakis(4-N-N-N-trimethylanilinium)porphyrin, $Mn^{III}$ tetrakis(1-methyl-4-pyridyl)porphyrin, $Mn^{III}$ tetrakis(4-benzoic acid)porphyrin, $Mn^{III}$ octabromo-meso-tetrakis(N-methylpyridinium-4-yl) porphyrin, $Fe^{III}$ tetrakis(4-N-methylpyridyl)porphyrin, and $Fe^{III}$ tetrakis-o-(4-N-methylisonicotinamidophenyl)porphyrin. These non-proteinaceous catalysts for the dismutation of superoxide also preferably contain a reactive moiety when the methods of surface covalent conjugation or copolymerization are used to modify the biomaterial. Thus, the present invention is directed to biomaterials which have been modified with any of the above non-proteinaceous catalysts for the dismutation of superoxide. In addition, as sometimes it is advantageous to add the chelated transition metal ion after the biomaterial has been modified, the present invention is also directed to biomaterials which have been modified with the precursor ligand of any of the above non-proteinaceous catalysts.

The present invention is also directed to processes for producing biomaterials modified by surface covalent conjugation with at least one non-proteinaceous catalyst for the dismutation of superoxide or at least one precursor ligand of a non-proteinaceous catalyst for the dismutation of superoxide, the process comprising:

a. providing at least one reactive functional group on a surface of the biomaterial to be modified;

b. providing at least one complementary reactive functional group on the non-proteinaceous catalyst for the dismutation of superoxide or on the precursor ligand; and c. conjugating the non-proteinaceous catalyst for the dismutation of superoxide or the precursor ligand with the surface of the biomaterial through at least one covalent bond.

The non-proteinaceous catalyst for the dismutation of superoxide or the precursor ligand can be covalently bound directly to the surface of the biomaterial, or bound to the surface through a linker molecule. Thus, the present invention is also directed to the above process further comprising providing a bi-functional linker molecule.

The present invention is also directed to a process for producing a biomaterial modified by co-polymerization with at least one non-proteinaceous catalyst for the dismutation of superoxide or at least on ligand precursor of a non-proteinaceous catalyst for the dismutation of superoxide, the process comprising:

a. providing at least one monomer;

b. providing at least one non-proteinaceous catalyst for the dismutation of superoxide or at least one ligand precursor of a non-proteinaceous catalyst for the dismutation of superoxide containing at least one functional group capable of reaction with the monomer and also containing at least one functional group capable of propagation of the polymerization reaction, c. copolymerizing the monomers and the non-proteinaceous catalyst for the dismutation of superoxide or the ligand precursor in a polymerization reaction.

The present invention is also directed to a process for producing a biomaterial modified by admixture with at least one non-proteinaceous catalyst for the dismutation of superoxide or a precursor ligand of a non-proteinaceous catalyst for the dismutation of superoxide, the process comprising:

a. providing at least one unmodified biomaterial;

b. providing at least one non-proteinaceous catalyst for the dismutation of superoxide or at least one ligand precursor of a non-proteinaceous catalyst for the dismutation of superoxide; and c. admixing the unmodified biomaterial and the non-proteinaceous catalyst for the dismutation of superoxide or the ligand precursor.

In addition, the present invention is also directed to a novel method of synthesizing PACPeD catalysts by using manganese or other transition metal ions as a template for cyclization the ligand.

The present invention is also directed to a biocompatible article comprising a biomaterial modified with at least one non-proteinaceous catalyst for the dismutation of superoxide or a ligand precursor of a non-proteinaceous catalyst for the dismutation of superoxide, wherein the catalyst or ligand precursor is presented on a surface of the article. The invention is also directed to the use of the biomaterials of the present invention in a stent, a vascular graft fabric, a nerve growth channel, a cardiac lead wire, or other medical devices for implantation in or contact with the body or bodily fluids.

BRIEF DESCRIPTION OF DRAWINGS AND DEFINITIONS

Drawings

FIG. 1: An electron micrograph of the surface of a control disk of poly(etherurethane urea) which has not been implanted.

Figure 2:
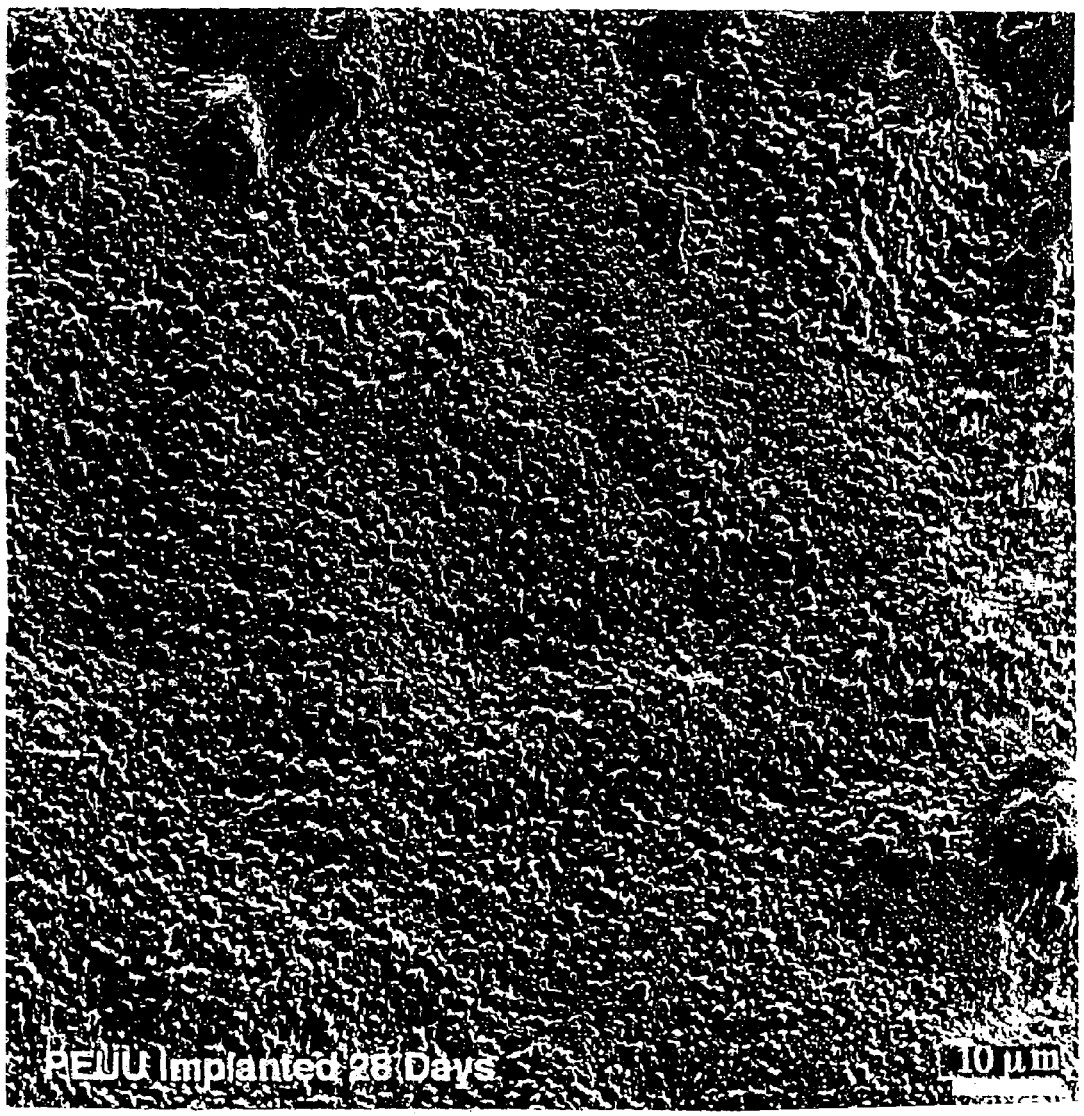

FIG. 2: An electron micrograph of the surface of a control disk of poly(etherurethane urea) (not conjugated with a non-proteinaceous catalyst for the dismutation of superoxide) which has been implanted in a rat for 28 days.

Figure 3:
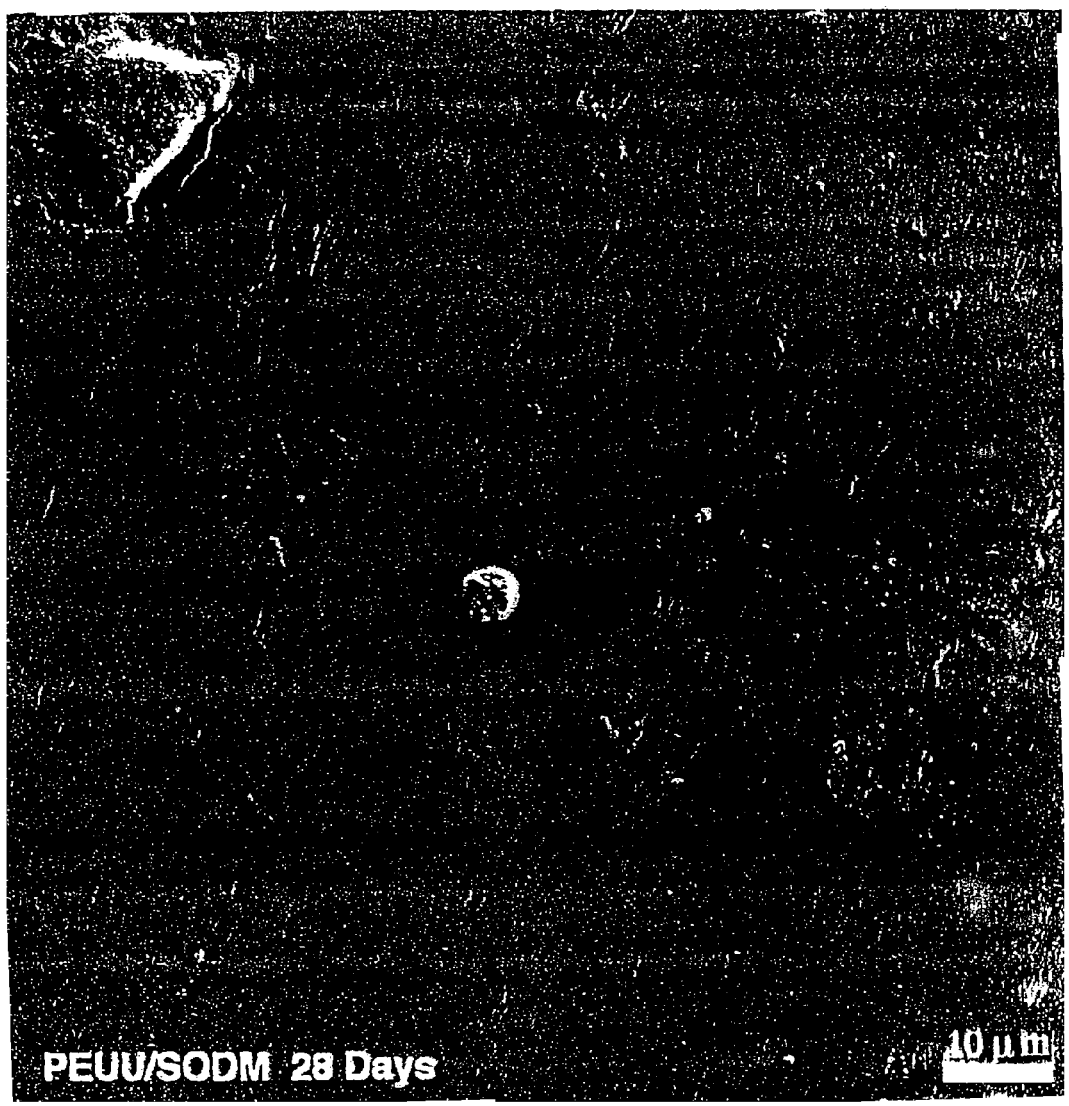

FIG. 3: An electron micrograph of the surface of a poly(etherurethane urea) disc which has been conjugated with Compound 43 and which has been implanted in a rat for 28 days.

FIG. 4: A comparison of capsules formed around polypropylene fibers which have been implanted into a rat. A) a control fiber, made of polypropylene which has not been admixed with a non-proteinaceous catalyst for the dismutation of superoxide; B) a fiber made of polypropylene which has been admixed with Compound 54, 2% by weight.

FIG. 5: A comparison of capsules formed around disks of polyethylene which have been implanted in a rat for 3 days. A) control disk, not conjugated with a non-proteinaceous catalyst; B) a disk conjugated with Compound 43, 0.06% by weight; C) a disc conjugated with Compound 43, 1.1% by weight.

FIG. 6: A comparison of capsules formed around disks of polyethylene which have been implanted in a rat for 28 days. A) control disk, not conjugated with a non-proteinaceous catalyst; B) a disk conjugated with Compound 43, 0.06% by weight; C) a disc conjugated with Compound 43, 1.1% by weight.

FIG. 7: A graphical comparison of the capsule thickness and number of giant cells in the capsule for polyethylene disks conjugated with Compound 43, 0.06% by weight, and polyethylene disks conjugated with Compound 43, 1.1% by weight, after implantation for 28 days.

FIG. 8: A comparison of capsules formed around disks of poly(etherurethane urea) which have been implanted in a rat for 28 days. A) control disk, not conjugated with a non-proteinaceous catalyst; B) a disk conjugated with Compound 43, 0.6% by weight; C) a disc conjugated with Compound 43, 3.0% by weight.

FIG. 9: A comparison of capsules formed around disks of tantalum which have been implanted in a rat for 3 days. A) control disk, conjugated only with the silyl linker; B) a disk conjugated with Compound 43 via the silyl linker.

Figure 10:

FIG. 10: A comparison of capsules formed around disks of tantalum which have been implanted in a rat for 28 days. A) control disk, conjugated only with the silyl linker; B) a disk conjugated with Compound 43 via the silyl linker.

FIG. 11: A drawing of the unwound wire used to make the stent of Example 26.

FIG. 12: A close up of the bends and "eyes" in the wire of FIG. 11.

Figure 13:
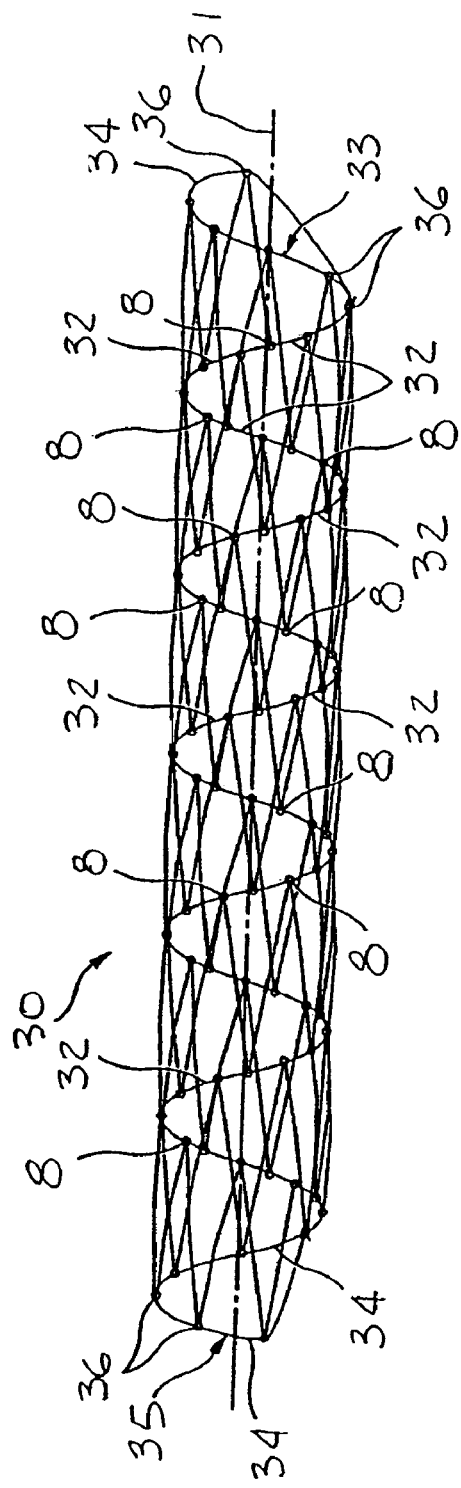

FIG. 13: A side view drawing of the helically wound stent, fully expanded.

Figure 14:
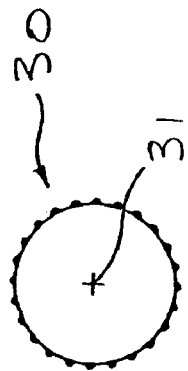

FIG. 14: A cross-section of the helically wound stent.

Figure 15:

FIG. 15: A side view drawing of the helically wound stent, compressed.

Figure 16:
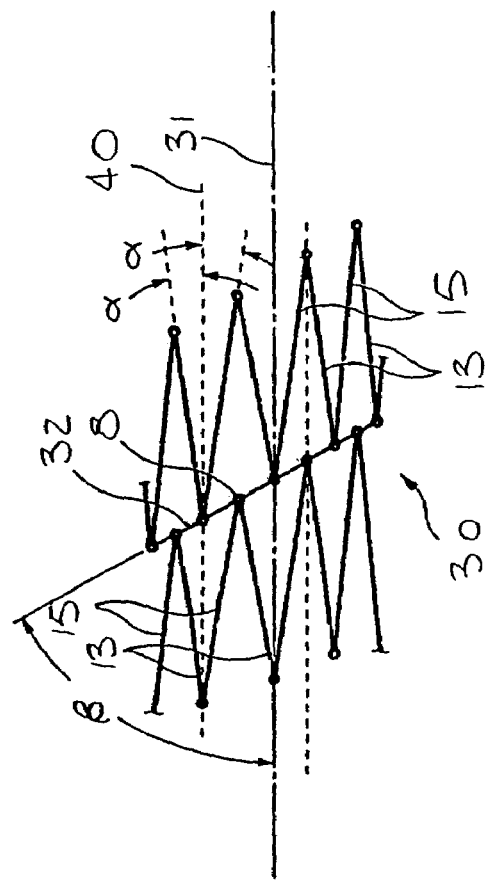

FIG. 16: A detailed view of the helically wound stent, showing the angle of the helix (∃) and the angle between the zig-zags of the stent wire (∀).

Definitions

As utilized herein, the term "biomaterial" includes any generally non-toxic material commonly used in applications where contact with biological systems is expected. Examples of biomaterials include: metals such as stainless steel, tantalum, titanium, nitinol, gold, platinum, inconel, iridium, silver, molybdenum, tungsten, nickel, chromium, vanadium, and alloys comprising any of the foregoing metals and alloys; ceramics such as hydroxyapatite, tricalcium phosphate, and aluminum-calcium-phosphorus oxide; polymers such as polyurethane, polyureaurethane, polyalkylene glycols, polyethylene teraphthalate, ultra high molecular weight polyethylenes, polypropylene, polyesters, polyamides, polycarbonates, polyorthoesters, polyesteramides, polysiloxanes, polyolefins, polytetrafluoroethylenes, polysulfones, polyanhydrides, polyalkylene oxides, polyvinyl halides, polyvinyledene halides, acrylics, methacrylics, polyacrylonitriles, polyvinyls, polyphosphazenes, polyethylene-co-acrylic acid, silicones, block copolymers of any of the foregoing polymers, random copolymers of any of the foregoing polymers, graft copolymers of any of the foregoing polymers, crosslinked polymers of any of the foregoing polymers, hydrogels, and mixtures of any of the foregoing polymers; biopolymers such as chitin, chitosan, cellulose, methyl cellulose, hyaluronic acid, keratin, fibroin, collagen, elastin, and saccharide polymers; biologically derived materials such as fixed tissues, and composites of such materials. "Biocompatible" articles are fabricated out of biomaterials. As used herein, the term "biomaterial" is not meant to encompass drugs and biologically active molecules such as steroids, di-saccharides and short chain polysaccharides, fatty acids, amino acids, antibodies, vitamins, lipids, phospholipids, phosphates, phosphonates, nucleic acids, enzymes, enzyme substrates, enzyme inhibitors, or enzyme receptor substrates.

The term "non-proteinaceous catalysts for the dismutation of superoxide" means a low-molecular-weight catalyst for the conversion of superoxide anions into hydrogen peroxide and molecular oxygen. These catalysts commonly consist of an organic ligand and a chelated transition metal ion, preferably manganese or iron. The term may include catalysts containing short-chain polypeptides (under 15 amino acids), or macrocyclic structures derived from amino acids, as the organic ligand. The term explicitly excludes a superoxide dismutase enzyme obtained from any species.

The term "precursor ligand" means the organic ligand of a non-proteinaceous catalyst for the dismutation of superoxide without the chelated transition metal cation.

The term "biopolymer" means a polymer which can be produced in a living system or synthetically out of amino acids, saccharides, or other typical biological monomers. The term also encompasses derivatives of these biological polymers. Examples of biopolymers include chitin, chitosan, cellulose, methyl cellulose, hyaluronic acid, keratin, fibroin, collagen, and elastin.

The term "biologically derived material" means biological tissue which has been chemically modified for implantation into a new host, such as fixed heart valves and blood vessels.

The term "modification" means any method by which a physical association may be effected between a biomaterial and a non-proteinaceous catalyst for the dismutation of superoxide, whereby the non-proteinaceous catalyst becomes integrated into or onto the biomaterial. Modification may be effected by surface covalent conjugation, copolymerization, admixture, or by other methods. When modification is achieved by admixture, it is understood that the non-proteinaceous catalyst is in the same phase as at least a part of the biomaterial that is modified.

The term "surface covalent conjugation" means that the non-proteinaceous catalyst is bound through at least one covalent bond to the surface of a biomaterial. The term encompasses conjugation via a direct covalent bond between the non-proteinaceous catalyst and the surface, as well as an indirect bond which includes a linker molecule between the non-proteinaceous catalyst and the surface of the biomaterial.

The term "linker" means any molecule with at least two functional groups which can be used to "link" one molecule to another. Examples of linkers include low molecular weight polyethylene glycol, hexamethyl di(imidi)-isocyanate, silyl chloride, and polyglycine.

The term "copolymerization" means that the non-proteinaceous catalyst is copolymerized with the monomer which forms the biomaterial, and thus integrated into the polymer chain of the modified biomaterial.

The term "inflammatory response" means that the material elicits the inflammation of the surrounding tissues and the production of degradative enzymes and reactive molecular species when exposed to biological systems.

The term "substituted" means that the described moiety has one or more of the following substituents:

(1) —NR$_{30}$R$_{31}$ wherein R$_{30}$ and R$_{31}$ are independently selected from hydrogen, alkyl, aryl or aralkyl; or R$_{30}$ is hydrogen, alkyl, aryl or aralkyl and R$_{31}$ is selected from the group consisting of —NR$_{32}$R$_{33}$, —OH, —OR$_{34}$,

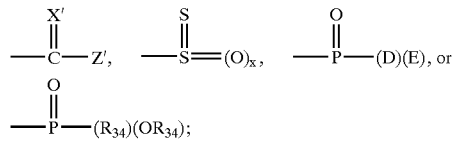

wherein R$_{32}$ and R$_{33}$ are independently hydrogen, alkyl, aryl or acyl, R$_{34}$ is alkyl, aryl or alkaryl, Z' is hydrogen, alkyl, aryl, alkaryl, —OR$_{34}$, —SR$_{34}$ or —NR$_{40}$R$_{41}$. R$_{37}$ is alkyl, aryl or alkaryl, X' is oxygen or sulfur, and R$_{38}$ and R$_{39}$ are independently selected from hydrogen, alkyl, or aryl;

(2) —SR$_{42}$ wherein R$_{42}$ is hydrogen, alkyl, aryl, alkaryl, —SR$_{34}$, —NR$_{32}$R$_{33}$,

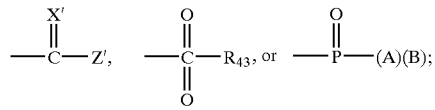

wherein R$_{43}$ is —OH, —OR$_{34}$ or —NR$_{32}$R$_{33}$, and A and B are independently —OR$_{34}$, —SR$_{34}$ or —NR$_{32}$R$_{33}$ (3) wherein x is 1 or 2, and R$_{44}$ is halide, alkyl, aryl, alkaryl, —OH, —OR$_{34}$ or —NR$_{32}$R$_{33}$;

(4) —OR$_{45}$ wherein R$_{45}$ is hydrogen, alkyl, aryl, alkaryl, —NR$_{32}$R$_{33}$,

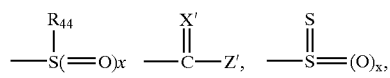

-continued

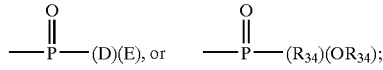

wherein D and E are independently —OR$_{34}$ or —NR$_{32}$R$_{33}$;

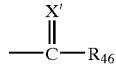

wherein R$_{46}$ is halide, —OH, —SH, —OR$_{34}$, —SR$_{34}$ or —NR$_{32}$R$_{33}$;

(6) amine oxides of the formula

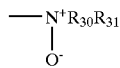

provided R$_{30}$ and R$_{31}$ are not hydrogen;

(7)

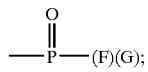

wherein F and G are independently —OH, —SH, —OR$_{34}$, —SR$_{34}$ or —NR$_{32}$R$_{33}$;

(8) —O—(—(CH$_2$)$_a$—O)$_b$—R$_{10}$ wherein R$_{10}$ is hydrogen or alkyl, and a and b are integers independently selected from 1+6;

(9) halogen, cyano, nitro or azido; or

(10) aryl, heteroaryl, alkynyl, or alkenyl.

Alkyl, aryl and alkaryl groups on the substituents of the above-defined alkyl groups may contain one or more additional substituents, but are preferably unsubstituted.

The term "functional group" means a group capable of reacting with another functional group to form a covalent bond. Functional groups preferably used in the present invention include acid halide (XCO— wherein X=Cl, F, Br, I), amino (H$_2$N—), isocyanate (OCN—), mercapto (HS—), glycidyl (H$_2$COCH—), carboxyl (HOCO—), hydroxy (HO—), and chloromethyl (ClH$_2$C—), silyl or silyl chloride, and substituted or unsubstituted alkenyl, alkynyl, aryl, and heteroaryl.

The term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms. Examples of such radicals include, but are not limited to, methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl.

The term "alkenyl", alone or in combination, means an alkyl radical having one or more double bonds. Examples of such alkenyl radicals include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl.

The term "alkynyl", alone or in combination, means an alkyl radical having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl.

The term "cycloalkyl", alone or in combination means a cycloalkyl radical containing from 3 to about 10, preferably from 3 to about 8, and most preferably from 3 to about 6, carbon atoms. Examples of such cycloalkyl radicals include, but are not limited to, cyclopropyl, cyclobutyl, cyclopentyl, cyclohexyl, cycloheptyl, cyclooctyl, and perhydronaphthyl.

The term "cycloalkylalkyl" means an alkyl radical as defined above which is substituted by a cycloalkyl radical as defined above. Examples of cycloalkylalkyl radicals include, but are not limited to, cyclohexylmethyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl.

The term "cycloalkylcycloalkyl" means a cycloalkyl radical as defined above which is substituted by another cycloalkyl radical as defined above. Examples of cycloalkylcycloalkyl radicals include, but are not limited to, cyclohexylcyclopentyl and cyclohexylcyclohexyl.

The term "cycloalkenyl", alone or in combination, means a cycloalkyl radical having one or more double bonds. Examples of cycloalkenyl radicals include, but are not limited to, cyclopentenyl, cyclohexenyl, cyclooctenyl, cyclopentadienyl, cyclohexadienyl and cyclooctadienyl.

The term "cycloalkenylalkyl" means an alkyl radical as defined above which is substituted by a cycloalkenyl radical as defined above. Examples of cycloalkenylalkyl radicals include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl)pentyl, 1-(1-cyclopenten-1-yl)hexyl, 6-(1-cyclohexen-1-yl)hexyl, 1-(1-cyclopenten-1-yl)nonyl and 1-(1-cyclohexen-1-yl)nonyl.

The terms "alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include, but are not limited to, 2-ethylcyclobutyl, 1-methylcyclopentyl, 1-hexylcyclopentyl, 1-methylcyclohexyl, 1-(9-octadecenyl)cyclopentyl and 1-(9-octadecenyl)cyclohexyl.

The terms "alkylcycloalkenyl" and "alkenylcycloalkenyl" means a cycloalkenyl radical as defined above which is substituted by an alkyl or alkenyl radical as defined above. Examples of alkylcycloalkenyl and alkenylcycloalkenyl radicals include, but are not limited to, 1-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl.

The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The term "aralkyl", alone or in combination, means an alkyl or cycloalkyl radical as defined above in which one hydrogen atom is replaced by an aryl radical as defined above, such as benzyl, 2-phenylethyl, and the like.

The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

The term "saturated, partially saturated or unsaturated cyclic" means fused ring structures in which 2 carbons of the ring are also part of the fifteen-membered macrocyclic ligand. The ring structure can contain 3 to 20 carbon atoms, preferably 5 to 10 carbon atoms, and can also contain one or more other kinds of atoms in addition to carbon. The most common of the other kinds of atoms include nitrogen, oxygen and sulfur. The ring structure can also contain more than one ring.

The term "saturated, partially saturated or unsaturated ring structure" means a ring structure in which one carbon of the ring is also part of the fifteen-membered macrocyclic ligand. The ring structure can contain 3 to 20, preferably 5 to 10, carbon atoms and can also contain nitrogen, oxygen and/or sulfur atoms.

The term "nitrogen containing heterocycle" means ring structures in which 2 carbons and a nitrogen of the ring are also part of the fifteen-membered macrocyclic ligand. The ring structure can contain 2 to 20, preferably 4 to 10, carbon atoms, can be substituted or unsubstituted, partially or fully unsaturated or saturated, and can also contain nitrogen, oxygen and/or sulfur atoms in the portion of the ring which is not also part of the fifteen-membered macrocyclic ligand.

The term "organic acid anion" refers to carboxylic acid anions having from about 1 to about 18 carbon atoms.

The term "halide" means chloride, floride, iodide, or bromide.

As used herein, "R" groups means all of the R groups attached to the carbon atoms of the macrocycle, i.e., R, R', $R_1$, $R'_1$, $R_2$, $R'_2$, $R_3$, $R'_3$, $R_4$, $R'_4$, $R_5$, $R'_5$, $R_6$, $R'_6$, $R'_7$, $R_8$, $R'_8$, $R_9$.

All references cited herein are explicitly incorporated by reference.

DETAILED DESCRIPTION OF THE INVENTION

The present invention concerns novel modified biomaterials and methods for the production of such materials. Prior to applicants' invention, it was not known that non-proteinaceous catalysts for the dismutation of superoxide could be immobilized on the surface of a biomaterial and still retain their catalytic function and exhibit an anti-inflammatory effect. However, applicants have found that these catalysts can be efficaciously immobilized on biomaterial surfaces and still retain superoxide dismutating ability, as shown by Example 23. Applicants have also found that these modified biomaterials have greatly improved durability and decreased inflammatory response when exposed to biological systems, such as the rat model in Examples 21 and 22.

Biomaterials and Non-Proteinaceous Catalysts for the Dismutation of Superoxide for Use in the Present Invention A variety of biomaterials are appropriate for modification in the present invention. The biomaterial to be modified can be any biologically compatible metal, ceramic, polymer, biopolymer, or a composite thereof. Metals suitable for use in the present invention include stainless steel, tantalum, titanium, nitinol, gold, platinum, inconel, iridium, silver, molybdenum, tungsten, nickel, chromium, vanadium, and alloys comprising any of the foregoing metals and alloys. Ceramics suitable for use in the present invention include hydroxyapatite, tricalcium phosphate, and aluminum-calcium-phosphorus oxide. Polymers suitable for use in the present invention include polyurethane, polyureaurethane, polyalkylene glycols, polyethylene teraphthalate, ultra high molecular weight polyethylenes, polypropylene, polyesters, polyamides, polycarbonates, polyorthoesters, polyesteramides, polysiloxanes, polyolefins, polytetrafluoroethylenes, polysulfones, polyanhydrides, polyalkylene oxides, polyvinyl halides, polyvinyledene halides, acrylics, methacrylics, polyacrylonitriles, polyvinyls, polyphosphazenes, polyethylene-co-acrylic acid, silicones, block copolymers of any of the foregoing polymers, random copolymers of any of the foregoing polymers, graft copolymers of any of the foregoing polymers, crosslinked copolymers of any of the foregoing polymers, hydrogels, and mixtures of any of the foregoing polymers. Biopolymers suitable for use in the present invention are chitin, chitosan, cellulose, methyl cellulose, hyaluronic acid, keratin, fibroin, collagen, elastin, and saccharide polymers. Composite materials which may be used in the present invention comprise a relatively inelastic phase such as carbon, hydroxy apatite, tricalcium phosphate, silicates, ceramics, or metals, and a relatively elastic phase such as a polymer or biopolymer.

Where the method used to modify the biomaterial is surface covalent conjugation, the unmodified biomaterial should contain, or be chemically derivatized to contain, a reactive moiety. Preferred reactive moieties include acid halide (XCO— wherein X=Cl, F, Br, I), amino ($H_2N$—), isocyanate (OCN—), mercapto (HS—), glycidyl ($H_2COCH$—), carboxyl (HOCO—), hydroxy (HO—), and chloromethyl ($ClH_2C$—), silyl or silyl chloride, and substituted or unsubstituted alkenyl, alkynyl, aryl, and heteroaryl moieties.

Applicants have discovered that these compounds, especially the preferred pentaaza non-proteinaceous catalysts, will survive a wide range of chemical reactions and processing conditions including extreme chemical and thermal conditions. Particularly, the PACPeD catalysts have been demonstrated by the applicants to be stable at temperatures up to about 350EC, and at pH of about 4. Additionally, the PACPeD's are soluble in a wide range of solvents, including water, methanol, ethanol, methylene chloride, DMSO, DMF, and DMAC, and are partially soluble in toluene and acetonitrile. By adding polar or non-polar substituents at the R group positions on the PACPeD or other non-proteinaceous catalysts, applicants have improved their solubility in specific solvents for particular reactions, and for use with particular biomaterials. As illustrated by Table 1 below, several reactive functional groups may be added as pendant moieties without detrimentally affecting the catalyst's superoxide dismutating ability.

The non-proteinaceous catalysts for the dismutation of superoxide for use in the present invention preferably comprise an organic ligand and a transition metal cation. Particularly preferred catalysts are manganese and iron chelates of pentaazacyclopentadecane compounds, which can be represented by the following formula:

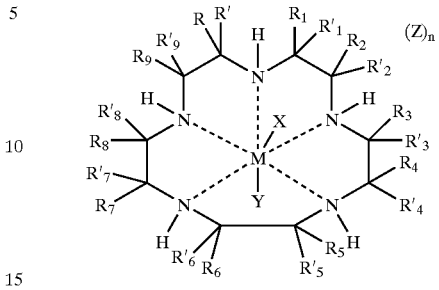

wherein M is a cation of a transition metal, preferably manganese or iron; wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ independently represent hydrogen, or substituted or unsubstituted alkyl, alkenyl, alkynyl, cycloalkyl, cycloalkenyl, cycloalkylalkyl, cycloalkylcycloalkyl, cycloalkenylalkyl, alkylcycloalkyl, alkylcycloalkenyl, alkenylcycloalkenyl, alkenylcycloalkenyl, heterocyclic, aryl and aralkyl radicals; $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a substituted or unsubstituted, saturated, partially saturated or unsaturated cyclic or heterocyclic having 3 to 20 carbon atoms; R or R'and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a substituted or unsubstituted nitrogen containing heterocycle having 2 to 20 carbon atoms, provided that when the nitrogen containing heterocycle is an aromatic heterocycle which does not contain a hydrogen attached to the nitrogen, the hydrogen attached to the nitrogen as shown in the above formula, which nitrogen is also in the macrocyclic ligand or complex, and the R groups attached to the included carbon atoms of the macrocycle are absent; R and R', $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atom to which they are attached independently form a saturated, partially saturated, or unsaturated cyclic or heterocyclic having 3 to 20 carbon atoms; and one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ together with a different one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ which is attached to a different carbon atom in the macrocyclic ligand may be bound to form a strap represented by the formula —$(CH_2)_x$-M-$(CH_2)_w$-L-$(CH_2)_z$—J—$(CH_2)_y$— wherein w, x, y and z independently are integers from 0 to 10 and M, L and J are independently selected from the group consisting of alkyl, alkenyl, alkynyl, aryl, cycloalkyl, heteroaryl, alkaryl, alkheteroaryl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza and combinations thereof; and combinations thereof. Thus, the PACPeD's useful in the present invention can have any combinations of substituted or unsubstituted R groups, saturated, partially saturated or unsaturated cyclics, ring structures, nitrogen containing heterocycles, or straps as defined above.

X, Y and Z represent suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion). X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid (such as acetic acid, trifluoroacetic acid, oxalic acid), aryl carboxylic acid (such as benzoic acid, phthalic acid), urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate aryl thiocarbamate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins. The preferred ligands from which X, Y and Z are selected include halide, organic acid, nitrate and bicarbonate anions.

The "R" groups attached to the carbon atoms of the macrocycle can be in the axial or equatorial position relative to the macrocycle. When the "R" group is other than hydrogen or when two adjacent "R" groups, i.e., on adjacent carbon atoms, together with the carbon atoms to which they are attached form a saturated, partially saturated or unsaturated cyclic or a nitrogen containing heterocycle, or when two R groups on the same carbon atom together with the carbon atom to which they are attached form a saturated, partially saturated or unsaturated ring structure, it is preferred that at least some of the "R" groups are in the equatorial position for reasons of improved activity and stability. This is particularly true when the complex contains more than one "R" group which is not hydrogen.

Where the modification of the biomaterial is effected by the surface covalent conjugation or copolymerization with the unmodified biomaterial, it is preferred that the PACPeD contain a pendant reactive moiety. This reactive moiety may be on a "R" group, a cyclic, a heterocyclic, a nitrogen containing heterocyclic, or a strap structure as described above. Preferred moieties on the non-proteinaceous catalyst for use in the present invention include of amino (—$NH_2$), carboxyl (—OCOH), isocyanate (—NCO), mercapto (—SH), hydroxy (—OH), silyl chloride (—$SiCl_2$), acid halide (—OCX wherein X=Cl, F, Br, I), halide (—X wherein X=Cl, F, Br, I), glycidyl (—$HCOCH_2$), and substituted or unsubstituted alkenyl, alkynyl, and aryl moieties.

Preferred PACPeD's for modification of biomaterials compounds are those wherein at least one "R" group contains a reactive functional group, and those wherein at least one, of R or R'and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached are bound to form a nitrogen containing heterocycle having 2 to 20 carbon atoms and all the remaining "R" groups are independently selected from hydrogen, saturated, partially saturated or unsaturated cyclic or alkyl groups. Examples of PACPeD catalysts useful in making the modified biomaterials of the invention include, but are not limited to, the following compounds:

TABLE 1

| COMPOUND | MOL. WT. | $k_{cat}$ pH 7.4 | $k_{cat}$ pH 8.1 |
|---|---|---|---|
| 1 | 341.19 | 4.13 | 2.24 |

TABLE 1-continued
| COMPOUND | MOL. WT. | $k_{cat}$ pH 7.4 | $k_{cat}$ pH 8.1 |
|---|---|---|---|
| 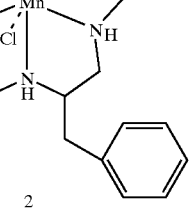 2 | 431.31 | 7.21 | 2.57 |
| 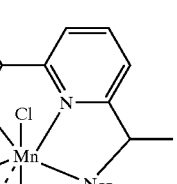 3 | 403.26 |  | 1.00 |
| 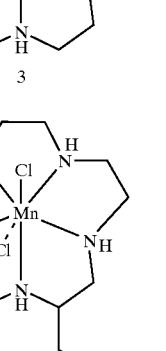 4 | 379.23 |  | 1.75 |
| 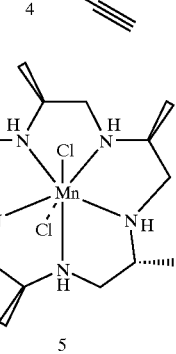 5 | 411.77 | 3.82 | 3.90 |
| 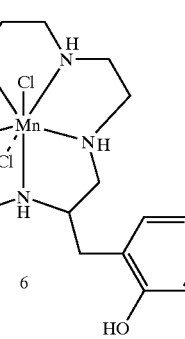 6 | 447.31 | 6.99 | 3.83 |

TABLE 1-continued

| COMPOUND | MOL. WT. | $k_{cat}$ pH 7.4 | $k_{cat}$ pH 8.1 |
|---|---|---|---|
| 7 | 501.37 | 2.00 | 1.58 |
| 8 | 584.39 | 5.95 | 5.90 |
| 9 | 423.22 | 2.71 | 1.68 |
| 10 | 491.32 | 2.68 | 2.68 |

TABLE 1-continued

| COMPOUND | MOL. WT. | $k_{cat}$ pH 7.4 | $k_{cat}$ pH 8.1 |
|---|---|---|---|
| 11 | 452.37 | 4.79 | 2.85 |
| 12 | 610.42 | 10.20 | 5.39 |
| 13 | 383.27 |  | 1.63 |
| 14 | 506.46 | 7.58 | 3.84 |

TABLE 1-continued
| COMPOUND | MOL. WT. | $k_{cat}$ pH 7.4 | $k_{cat}$ pH 8.1 |
|---|---|---|---|
| 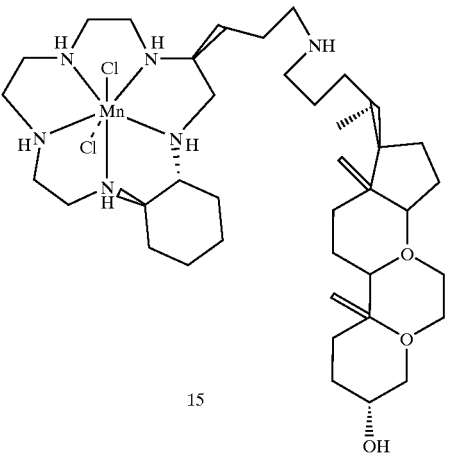 15 | 795.95 | 2.41 | 0.77 |
| 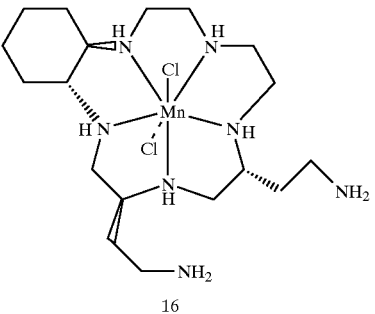 16 | 481.41 | 2.48 | 1.97 |
| 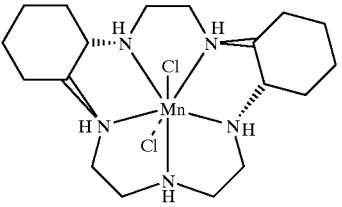 17 | 449.37 | 12.60 | 4.09 |
| 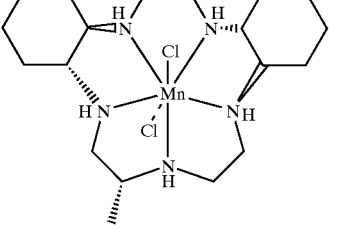 18 | 463.40 | 15.00 | 4.00 |

TABLE 1-continued
| COMPOUND | MOL. WT. | $k_{cat}$ pH 7.4 | $k_{cat}$ pH 8.1 |
|---|---|---|---|
| 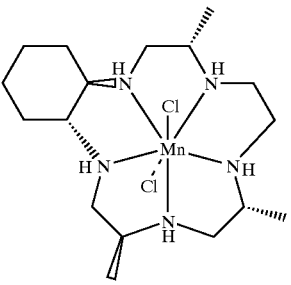 19 | 437.36 | 8.48 | 4.08 |
| 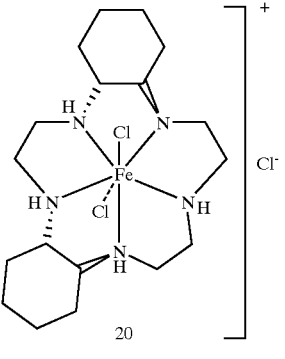 20 | 485.70 | 3.29 | 0.93 |
| 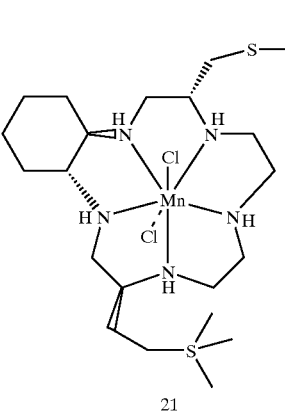 21 | 599.67 | 2.93 | 1.29 |
| 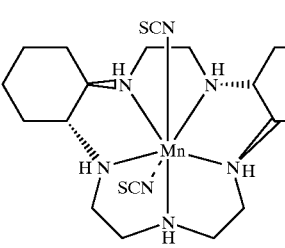 22 | 494.63 | 11.40 | 5.03 |

TABLE 1-continued

| COMPOUND | MOL. WT. | $k_{cat}$ pH 7.4 | $k_{cat}$ pH 8.1 |
|---|---|---|---|
| 23 | 461.29 | 6.61 | 3.47 |
| 24 | 493.38 | 2.55 | 2.55 |
| 25 | 724.39 | 4.04 | 2.34 |
| 26 | 479.40 | 10.12 | 3.47 |

TABLE 1-continued

| COMPOUND | MOL. WT. | $k_{cat}$ pH 7.4 | $k_{cat}$ pH 8.1 |
|---|---|---|---|
| 27 | 525.47 | 4.83 | 2.50 |
| 28 | 411.56 | | |
| 29 | 454.10 | 2.86 | 2.02 |
| 30 | 409.22 | 0.20 | 0.20 |

TABLE 1-continued
| COMPOUND | MOL. WT. | $k_{cat}$ pH 7.4 | $k_{cat}$ pH 8.1 |
|---|---|---|---|
| 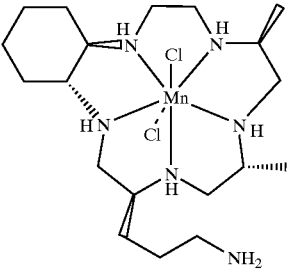 31 | 480.43 | 2.97 | 2.91 |
| 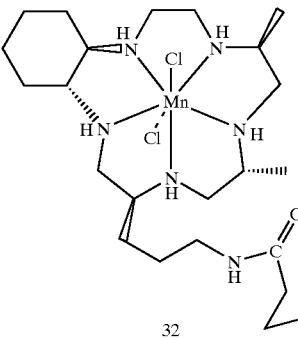 32 | 681.70 | 1.74 | 1.43 |
| 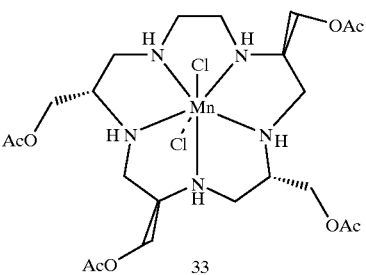 33 | 629.44 | 7.27 | 4.08 |
| 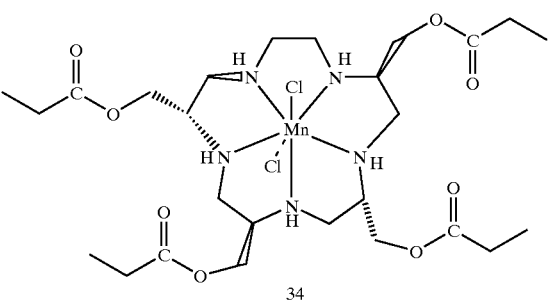 34 | 685.55 | 2.70 | 2.78 |

TABLE 1-continued
| COMPOUND | MOL. WT. | $k_{cat}$ pH 7.4 | $k_{cat}$ pH 8.1 |
|---|---|---|---|
| 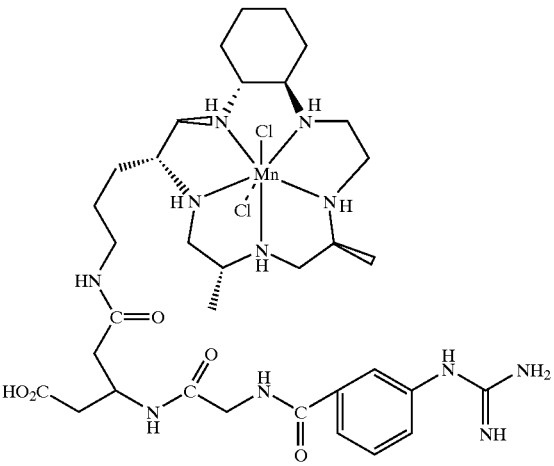 35 | 827.76 | 4.38 | 2.87 |
| 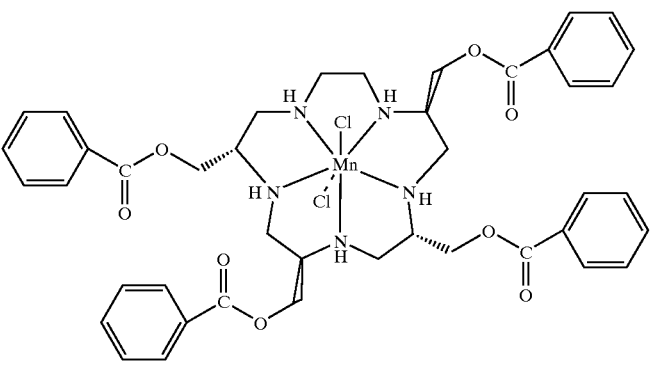 36 | 877.72 | 0.63 | 0.49 |
| 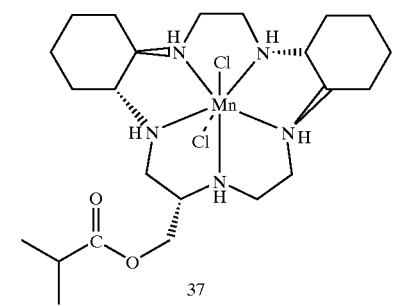 37 | 549.49 | 3.08 | |
| 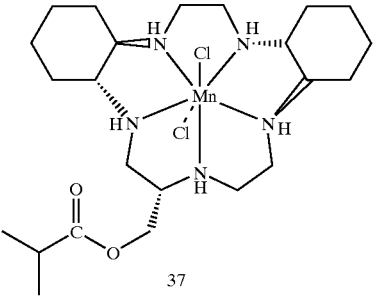 37 | | | |

TABLE 1-continued

| COMPOUND | MOL. WT. | $k_{cat}$ pH 7.4 | $k_{cat}$ pH 8.1 |
|---|---|---|---|
| 38 | 483.39 | 1.64 | 1.19 |
| 39 | 535.46 | 3.89 | 2.32 |
| 40 | 511.44 | 90.00 | 11.00 |
| 41 | 511.44 | 1.57 | 0.41 |

TABLE 1-continued

| COMPOUND | MOL. WT. | $k_{cat}$ pH 7.4 | $k_{cat}$ pH 8.1 |
|---|---|---|---|
| 42 | 517.83 | 1.18 | 0.98 |
| 43 | | | |
| 44 | 679.76 | 1.02 | 0.84 |
| 45 | 587.51 | 2.99 | 0.95 |

TABLE 1-continued

| COMPOUND | MOL. WT. | k$_{cat}$ pH 7.4 | k$_{cat}$ pH 8.1 |
|---|---|---|---|
| 46 | 563.52 | | |
| 47 | 537.48 | | 2.16 |
| 48 | 562.28 | 1.68 | |
| 49 | 614.52 | | |

TABLE 1-continued

| COMPOUND | MOL. WT. | $k_{cat}$ pH 7.4 | $k_{cat}$ pH 8.1 |
|---|---|---|---|
| 50 | 641.50 | 1.31 | |
| 51 | 573.53 | 3.97 | 1.14 |
| 52 | 537.02 | 3.01 | |
| 53 | | | |

TABLE 1-continued

| COMPOUND | MOL. WT. | $k_{cat}$ pH 7.4 | $k_{cat}$ pH 8.1 |
|---|---|---|---|
| 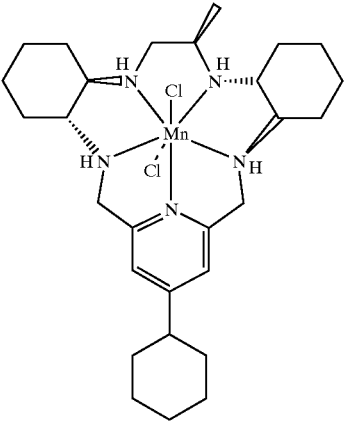 54 | 579.56 | 2.68 | |

Activity of the non-proteinaceous catalysts for the dismutation of superoxide can be demonstrated using the stopped-flow kinetic analysis technique as described in Example 24, and in Riley, D. P., Rivers, W. J. and Weiss, R. H., "Stopped-Flow Kinetic Analysis for Monitoring Superoxide Decay in Aqueous Systems," Anal. Biochem., 196, 344–349 (1991), which is incorporated by reference herein. Stopped-flow kinetic analysis is an accurate and direct method for quantitatively monitoring the decay rates of superoxide in water. The stopped-flow kinetic analysis is suitable for screening compounds for SOD activity and activity of the compounds or complexes of the present invention, as shown by stopped-flow analysis, correlate to usefulness in the modified biomaterials and processes of the present invention. The catalytic constants given for the exemplary compounds in the table above were determined using this method.

As can be observed from the table, a wide variety of PACPeD's with superoxide dismutating activity may be readily synthesized. Generally, the transition metal center of the catalyst is thought to be the active site of catalysis, wherein the manganese or iron ion cycles between the (II) and (III) states. Thus, as long as the redox potential of the ion is in a range in which superoxide anion can reduce the oxidized metal and protonated superoxide can oxidize the reduced metal, and steric hindrance of the approach of the superoxide anion is minimal, the catalyst will function with a kcat of about $10^6$ to $10^8$.

Without limiting themselves to any particular theory, applicants propose that the mechanism described in Riley, et al., 1999, is a reasonable approximation of how the PACPeD catalysts dismutate superoxide. In order for the complex to exhibit superoxide dismutase activity, the ligand should be able to fold into a conformation that allows the stabilization of an octahedral complex between the superoxide anion and the five nitrogens of the ligand ring. If a compound contains several conjugated double bonds within the main 15-membered ring of the ligand, which hold the ring in a rigid conformation, the compound would not be expected to exhibit catalytic activity. R groups which are coordinated with the transition metal ion freeze the conformation of the ligand, and would be expected to be poor catalysts. Large, highly electronegative groups pendant on the macrocycle would also sterically hinder the necessary conformational change. The lack of functionality in these types of PACPeD derivatives would not be unexpected by one of ordinary skill in the art. Specifically, one of skill in the art would avoid materially changing the flexibility of the PACPeD by adding many large groups which would cause steric hindrance, or placing too many double bonds into the main PACPeD ring. This effect would also be present in certain geometric arrangements of smaller R groups which constrain the complex to a rigid, planar geometry. Those particular compounds which do not exhibit superoxide dismutase activity should not be used to modify the biomaterials of the present invention.

Given these examples and guidelines, one of ordinary skill would be able to choose a PACPeD catalyst for use in the present invention which would contain any required functional group, while still retaining superoxide dismutating activity. The PACPeD catalysts described above may be produced by the methods disclosed in U.S. Pat. No. 5,610,293. However, it is preferred that the PACPeD catalysts used in the present invention be synthesized by the template method, diagramed below. This synthesis method is advantageous over previously disclosed methods in that cyclization yields utilizing the template method are usually about 90%, as compared to about 20% with previous methods. Several diamines are commercially available as starting materials, or a diamine may be synthesized. The diamine is reacted with titryl chloride in anhydrous methylene chloride at 0EC and allowed to warm to room temperature overnight, with stirring. The product is then combined with glyoxal in methanol and stirred for 16 hours. The glyoxal bisimine product is then reduced with a borohydride in THF. If a non-symmetrical product is desired, two diamines may be used as starting materials. In addition, a substituted glyoxal may be used if groups pendant from the macrocycle opposite the pyridine are desired ($R_5$ and $R_4$) Commercially available tetraamines may also be used in place of the reduced glyoxal bisimine. After reduction of the glyoxal bisimine, the product is combined with a 2,6 dicarbonyl substituted pyridine, such as 2,6, dicarboxaldyhyde pyridine or 2,6 diacetyl pyridine, and a salt of manganese or iron under basic conditions. The transition metal ion serves as a template to promote cyclization of the substituted pyridine and the tetraamine. Several 2,6 dicarbonyl substituted pyridines are available commercially, allowing for the facile production of a variety of ligands with groups pendant from the macrocycle proximal to the pyridine ($R_2$ and $R_3$). Additionally, pyridines with additional substitutions ($R_6$, $R_7$ and $R_8$) may also be used. After cyclization, the product is reduced with ammonium formate and a palladium catalyst over a period of 3–4 days. In addition to the "R" substitutions, "R'" groups may also be substituted at the same carbons. "R" and "R'" groups may be any of those indicated above. The process may be varied according to principles well known to one of ordinary skill in the art in order to accommodate various starting materials.

able method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

Also suitable for use in the present invention, but less preferred than the PACPeD's, are the salen complexes of manganese and iron disclosed in U.S. Pat. No. 5,696,109,

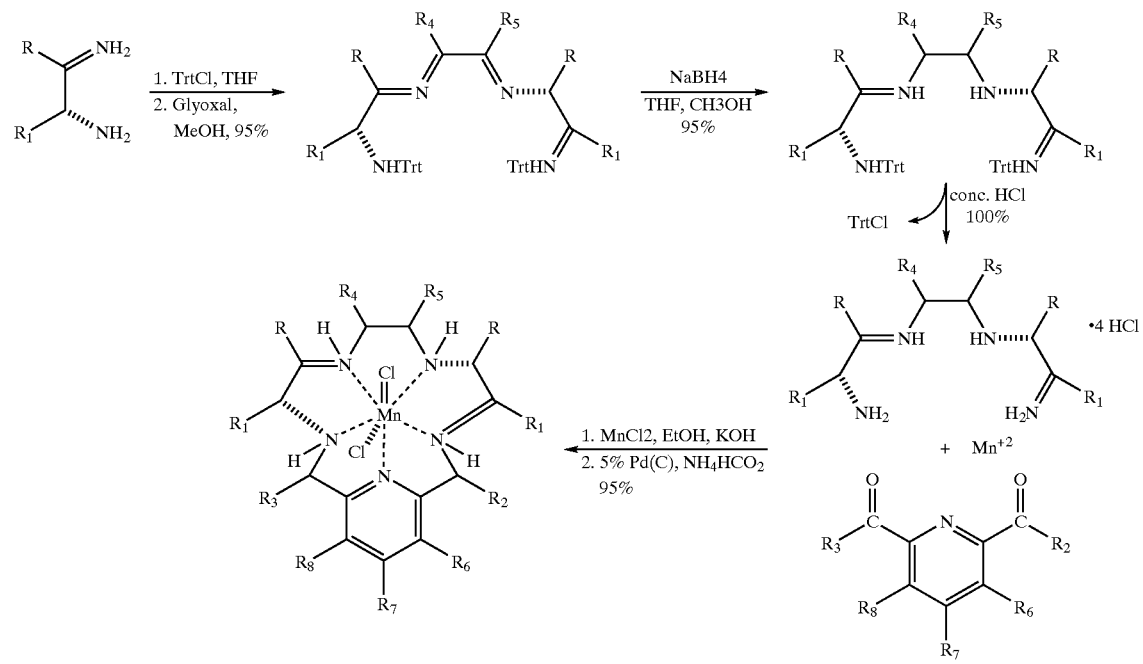

Although the bisimine produced in the template cyclization reaction step above may be reduced by more conventional means using hydrogen gas, it is preferred that the bisimine be reduced with ammonium formate in the presence of a palladium catalyst, as illustrated in Example 6. This process offers the advantages of increased safety and high reduction efficiency.

The PACPeD's useful in the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another availhere incorporated by reference. The term "salen complex" means a ligand complex with the general formula:

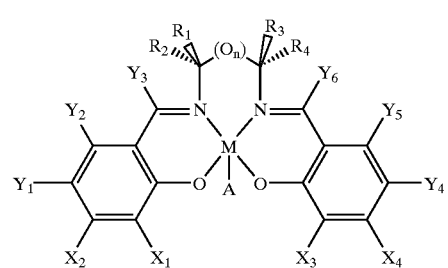

wherein M is a transition metal ion, preferably Mn; A is an anion, typically Cl; and n is either 0, 1, or 2. $X_1$, $X_2$, $X_3$ and $X_4$ are independently selected from the group consisting of hydrogen, silyls, arlyls, aryls, arylalkyls, primary alkyls, secondary alkyls, tertiary alkyls, alkoxys, aryloxys, aminos, quaternary amines, heteroatoms, and hydrogen; typically $X_1$ and $X_3$ are from the same functional group, usually hydrogen, quaternary amine, or tertiary butyl, and $X_2$ and $X_4$ are typically hydrogen. $Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms; aryloxys, alkoxys, and halide; preferably, $Y_1$ and $Y_4$ are alkoxy, halide, or amino groups. Typically, $Y_1$ and $Y_4$ are the same. $R_1$, $R_2$, $R_3$ and $R_4$ are independently selected from the group consisting of H, $CH_3$, $C_2H_5$, $C_6H_5$, O-benzyl, primary alkyls, fatty acid esters, substituted alkoxyaryls, heteroatom-bearing aromatic groups, arylalkyls, secondary alkyls, and tertiary alkyls. Methods of synthesizing these salen complexes are also disclosed in U.S. Pat. No. 5,696,109.

Iron or manganese porphyrins, such as , such as $Mn^{III}$ tetrakis(4-N-methylpyridyl)porphyrin, $Mn^{III}$ tetrakis-o-(4-N-methylisonicotinamidophenyl)porphyrin, $Mn^{III}$ tetrakis (4-N-N-N-trimethylanilinium)porphyrin, $Mn^{III}$ tetrakis(1-methyl-4-pyridyl)porphyrin, $Mn^{III}$ tetrakis(4-benzoic acid) porphyrin, $Mn^{III}$ octabromo-meso-tetrakis(N-methylpyridinium-4-yl)porphyrin, $Fe^{III}$ tetrakis(4-N-methylpyridyl)porphyrin, and $Fe^{III}$ tetrakis-o-(4-N-methylisonicotinamidophenyl)porphyrin. may also be used in the present invention. The catalytic activities and methods of purifying or synthesizing these porphyrins are well known in the organic chemistry arts.

The salen and porphyrin non-proteinaceous catalysts for the dismutation of superoxide also preferably contain a reactive moiety, as described above, when the methods of surface covalent conjugation or copolymerization are used to modify the biomaterial.

In general, the non-proteinaceous catalysts for the dismutation of superoxide used in the present invention are very stable under conditions of high heat, acid or basic conditions, and in a wide variety of solvents. However, under extreme reaction conditions the chelated transition metal ion will dissociate from the non-proteinaceous catalyst. Thus, when extreme reaction conditions are necessary to modify the biomaterial, it is preferable to modify the biomaterial with a precursor ligand of the non-proteinaceous catalyst for the dismutation of superoxide, and then afterwards react the modified biomaterial with a compound containing the appropriate transition metal in order to produce a biomaterial modified with an active non-proteinaceous catalyst for the dismutation of superoxide. For instance, when a PACPeD catalyst is used under reaction conditions of pH <4, the strategy of modifying the biomaterial with the ligand should be used. This strategy is demonstrated in Example 19. Therefore, when the term non-proteinaceous catalyst for the dismutation of superoxide is used in this specification, the reader should assume that, where appropriate, the precursor ligand will be used in the modification of the biomaterial, and that the transition metal cation necessary for activity may be added at a later point in time. Conditions where this approach would be appropriate may be readily determined by one of ordinary skill in the chemical arts.

Choice of Method of Modification

As previously described, the biomaterials of the present invention may be modified by the diverse methods of surface covalent conjugation, copolymerization, or admixture. The methods of surface covalent conjugation and copolymerization use covalent bonds in order to physically associate the non-proteinaceous catalyst for the dismutation of superoxide with the biomaterial. This creates a very stable physical association which preserves the superoxide dismutating activity of the modified biomaterial. In contrast, non-covalent forces create the physical association between the biomaterial and the non-proteinaceous catalysts for the dismutation of superoxide when the technique of physical admixture is used. These non-covalent forces may be weak Van der Wal's forces, or they may be stronger ionic bonding or hydrophobic interaction forces. Although ionic or hydrophobic interactions between the non-proteinaceous catalyst and the biomaterial will prevent elution of the non-proteinaceous catalyst to some degree, the catalyst will still be lost from the biomaterial over time when the biomaterial is exposed to biological tissues or fluids. Thus, it is usually preferred that the methods of covalent surface conjugation or copolymerization be used to modify biomaterials which will be exposed to biological systems for prolonged periods of time. However, uses may arise where the elution of non-proteinaceous catalysts for the dismutation of superoxide into the tissues surrounding an article comprising the modified biomaterial may be desirable. In this case, the use of biomaterials modified by the physical admixture method would be appropriate.

When composite materials are used, it may be necessary to utilize a variety of modification techniques. For instance, in a biomaterial composed of hydroxyapatite and polyethylene, a non-proteinaceous catalyst may be admixed with the hydroxyapatite phase of the composite, and another copolymerized with the polyethylene phase of the composites. The two composites may then be joined together into a fully modified composite biomaterial. Similarly, a composite material which utilizes carbon fiber and polypropylene could be made using a copolymerized polypropylene and a surface covalently conjugated carbon fiber. The flexibility in the production of modified biomaterials offered by the processes of the invention allows for the use of several diverse materials in a device while increasing its durability and decreasing the inflammatory response to the device.

Generally, it is preferred that the non-proteinaceous catalyst be present in an amount of about 0.001 to 25 weight percent. It is more preferable that the catalyst be present in an amount of about 0.01 to 10 weight percent. It is most preferable that the catalyst be present in an amount of about 0.05 to 5 weight percent. However, the amount of the non-proteinaceous catalyst to be used in modifying the biomaterial will depend on several factors, including the characteristics of the catalyst, the characteristics of the biomaterial, and the method of modification used. As is evident from the chart above, the catalytic activity of the non-proteinaceous catalysts for use in the present invention may vary over several orders of magnitude. Thus, less of the more efficient catalysts will be needed to obtain the same protective effects. Also, some biomaterials are more inflammatory than others. Thus, a greater amount of catalyst should be used with these biomaterials in order to counteract the strong inflammatory foreign body response that they provoke. In addition, the amount of catalyst used to modify the biomaterial should not be so high as to significantly alter the mechanical characteristics of the biomaterial. Because a covalently conjugated catalyst is concentrated at the surface of the biomaterial used in a device, almost all of the catalyst will interact with the biological environment. Conversely, because an admixed or copolymerized catalyst is dispersed throughout the biomaterial, less of the catalyst will be available to interact with the biological environment at the surface of the biomaterial. Thus, when the catalyst is covalently conjugated to the surface of the biomaterial, less catalyst will be needed than if the catalyst is admixed or copolymerized with the biomaterial. Given the above considerations, the person of ordinary skill in the art would be able to choose a proper amount of non-proteinaceous catalyst to use in the present invention in order to achieve the desired reduction in the inflammatory response and degradation.

It is to be understood that although the non-proteinaceous catalysts used in the following processes are usually referred to in the singular, multiple catalysts may be used in any of these processes. One of ordinary skill in the art will easily be able to choose complementary catalysts for such modified biomaterials. In addition, although not specifically enumerated herein, the combination of the biomaterial modification techniques of the present invention with other biomaterial modification techniques, such as heparin coating, is contemplated within the present invention.

Modification by Surface Covalent Conjugation

The general process for producing a biomaterial modified by surface covalent conjugation with at least one non-proteinaceous catalyst for the dismutation of superoxide or at least one precursor ligand of a non-proteinaceous catalyst for the dismutation of superoxide, comprises:

a. providing at least one reactive functional group on a surface of the biomaterial to be modified;
b. providing at least one complementary reactive functional group on the non-proteinaceous catalyst for the dismutation of superoxide or on the precursor ligand; and
c. conjugating the non-proteinaceous catalyst for the dismutation of superoxide or the precursor ligand with the surface of the biomaterial through at least one covalent bond.

This process may be effected by a photo-chemical reaction, or any of a number of conjugating reactions known in the art, such as condensation, esterification, oxidative, exchange, or substitution reactions. Preferred conjugation reactions for use in the present invention do not involve extreme reaction conditions, such as a temperature above about 375EC, or pH less than about 4. In addition, it is preferred that the conjugation reaction not produce a covalent bond that is readily cleaved by common enzymes found in biological systems. Usually, it is desirable for the non-proteinaceous catalyst to have only one complementary functional group. However, in cases where crosslinking of the biomaterial is desired, such as in hydrogels, polyfunctional-group catalysts may be used. Care should be taken, however, to choose functional groups which will not allow the non-proteinaceous catalyst to self-polymerize, as this will decrease the efficiency of the conjugation reaction. Likewise, multiple non-proteinaceous catalysts may be used to modify the biomaterial, although complementary functional groups which allow avoid inter-catalyst conjugations would not be preferred.

The non-proteinaceous catalyst for the dismutation of superoxide or the precursor ligand may be covalently bound directly to the surface of the biomaterial, or bound to the surface through a linker molecule. Where the non-proteinaceous catalyst and the surface of the biomaterial are directly conjugated, the reactive functional group and the complementary reactive functional group will form a covalent bond in the conjugation reaction. For instance, poly(ethyleneterephthalate) may be hydrolyzed to carboxyl functional groups. Compound 43 may then be reacted with the derivatized polymer to form the amide bond, as illustrated in Example 7. Examples H and E also illustrate a direct surface covalent conjugation. Further suggestions for reactive groups to use in of direct conjugation may be found in U.S. Pat. No. 5,830,539, herein incorporated by reference. Several exemplary paired functional groups are given in Table 2:

TABLE 2

| Non-proteinaceous Catalyst (SODm) Group | Substrate (R) Group | Resulting Linkage |
|---|---|---|
| SODm-NH$_2$ | R—N=C=O | R—NH—C(=O)—NH-SODm |
| SODm-NH$_2$ | R—C(=O)—OH | R—C(=O)—NH-SODm |
| SODm-NH$_2$ | R—C(=O)—X (X = Cl, F, Br, I) | R—C(=O)—NH-SODm |
| SODm-NH$_2$ | R—C(=O)—H | R—CH=NH-SODm |
| SODm-NH$_2$ | R—CH(—O—)CH$_2$ (epoxide) | R—CH(OH)—CH$_2$—NH-SODm |
| SODm-NH$_2$ | R—N=C=S | R—NH—C(=S)—NH-SODm |
| SODm-OH | R—N=C=O | R—NH—C(=O)—O-SODm |
| SODm-OH | R—C(=O)—OH | R—C(=O)—O-SODm |
| SODm-OH | R—CH(—O—)CH$_2$ (epoxide) | R—CH(OH)—CH$_2$—O-SODm |
| SODm-OH | R—N=C=S | R—NH—C(=S)—O-SODm |
| SODm-OH | R—C(=O)—X | R—C(=O)—O-SODm |
| SODm-OH | R—Si—(OCH$_3$)$_3$ | R—Si—(O-SODm)$_3$ |
| SODm-C(=O)—OH | R—OH | R—O—C(=O)-SODm |
| SODm-C(=O)—OH | R—N=C=O | R—NH—C(=O)—O-SODm |
| SODm-C(=O)—OH | R—C(=O)—X | R—C(=O)—O—C(=O)-SODm |
| SODm-C(=O)—OH | R—CH(—O—)CH$_2$ (epoxide) | R—CH(OH)—CH$_2$—O—C(=O)-SODm |

TABLE 2-continued

| Non-proteinaceous Catalyst (SODm) Group | Substrate (R) Group | Resulting Linkage |
|---|---|---|
| SODm-C(=O)-OH | R-NH$_2$ | R-N(H)-C(=O)-O-SODm |

When a linker molecule is used, the above process further comprises providing at least one linker capable of reacting with both the reactive functional group on a surface of the biomaterial to be modified and the complementary reactive functional group on the non-proteinaceous catalyst for the dismutation of superoxide or the precursor ligand. During the conjugation process, the reactive functional group on the surface of the article and the complementary reactive functional group on the non-proteinaceous catalyst for the dismutation of superoxide form a covalent bond with the linker. This process may occur all in one step, or in a series of steps. For instance, in a two step process, a carboxyl functionalized polymer, such as a hydrolyzed poly(ethyleneterephthalate) polymer ("PET") could first be reacted with a (Gly)$_{12}$ linker in an amide reaction. Then, after removal of excess linker, the PET-glycine linker could react with an amino PACPeD such as Compound 43 to form a polymer-glycine linker-Compound 43 modified biomaterial. Alternately, the hydrolyzed PET could be linked with a low molecular weight PEG to a carboxyl PACPeD such as Compound 52 by an ester reaction in a single step. Linkers suitable for use in this process include polysaccharides, polyalkylene glycols, polypeptides, polyaldehydes, and silyl groups. Silyl groups are particularly useful in conjugating non-proteinaceous catalysts with metal biomaterials. Examples of linkers and functional groups which are useful in the present invention may be found in U.S. Pat. Nos. 5,877,263 and 5,861,032. Persons of ordinary skill in the chemical arts will be able to determine an appropriate linker and non-proteinaceous catalyst for conjugation to any biomaterial, including metals, ceramics, polymers, biopolymers, and various phases of composites.

This method of modification may be used with an article which is already in its final form, or may be used with parts of an article before final assembly. In addition, this method is useful for modifying thin stock materials which will be used in the later manufacture of a device, such as polymer or chitosan films, or fibers which will be woven into fabrics for vascular grafts. This method is also useful for modifying diverse materials in a single step with one non-proteinaceous catalyst. For instance, a tantalum component which has been reacted with a silyl linker, as in Example 13, and a poly(ethyleneterephthalate) component which has been hydrolyzed, as in Example 7, may be assembled into a final device. Then, Compound 43 could be reacted with the entire article to modify the surface of both materials in a single step.

Modification by Copolymerization

Biomaterials may also be modified according to the present invention by co-polymerization with a non-proteinaceous catalyst for the dismutation of superoxide or the ligand precursor of a non-proteinaceous catalyst for the dismutation of superoxide. This process, inc general, comprises:

a. providing at least one monomer;
b. providing at least one least one non-proteinaceous catalyst for the dismutation of superoxide or at least one ligand precursor of a non-proteinaceous catalyst for the dismutation of superoxide containing at least one functional group capable of reaction with the monomer and also containing at least one functional group capable of propagation of the polymerization reaction,
c. copolymerizing the monomers and the non-proteinaceous catalyst for the dismutation of superoxide or the ligand precursor in a polymerization reaction.

The copolymerization technique is advantageous for the modification of polymers and synthetic biopolymers with non-proteinaceous catalysts for the dismutation of superoxide. However, it is preferred that this method be used with polymers whose polymerization reaction occurs at temperatures less than about 375EC, and pH greater than about 4. If the polymerization reaction is carried out at a pH less than 4, a ligand precursor of the non-proteinaceous catalysts for the dismutation of superoxide should be used. Monomers useful in this process include alkylenes, vinyls, vinyl halides, vinyledenes, diacids, acid amines, diols, alcohol acids, alcohol amines, diamines, ureas, urethanes, phthalates, carbonic acids, orthoesters, esteramines, siloxanes, phosphazenes, olefins, alkylene halides, alkylene oxides, acrylic acids, sulfones, anhydrides, acrylonitriles, saccharides, and amino acids.

As demonstrated previously, the non-proteinaceous catalysts for the dismutation of superoxide used in the present invention may be synthesized with any functional group necessary to react with the any of these monomers. In order to prevent the termination of the polymerization reaction, it is necessary that the non-proteinaceous catalyst also contain a polymerization propagation functional group. Often, this will be another functional group identical to the first functional group, as in the diamine PACPeD Compound 16. This catalyst is copolymerized with polyureaurethane in Example 16. However, as when the polymerization reaction involves a vinyl reaction, the reactive and propagative functional groups may be the same, such as in the acryloyl derivatized Compound 53. Copolymerization of this catalyst with acrylic or methacrylic is shown in Example 17. Example 18 also illustrates the modification of biomaterials by copolymerization with non-proteinaceous catalysts.

Biomaterials modified by copolymerization have several advantages. First, the non-proteinaceous catalysts for the dismutation of superoxide are covalently bound to the modified biomaterial, preventing dissociation of the catalysts and a loss of function. Second, the modification of the material is continuous throughout the biomaterial, allowing for continuous protection by the catalyst if the exterior surface of the material is by mechanical or chemical degradation. Third, the material can be melted and re-formed into any useful article after modification, provided that the polymer melts below about 375EC. Alternatively, wet-spinning or solvent casting may be used to make articles from these modified polymer biomaterials. These characteristics make the modified polymer biomaterials produced by this process a versatile tool for various medical device applications.

Modification by Admixture

The biomaterials of the present invention may also be modified by admixture with at least one non-proteinaceous catalyst for the dismutation of superoxide or a precursor ligand of a non-proteinaceous catalyst for the dismutation of superoxide. The general process comprises:

a. providing at least one unmodified biomaterial;
b. providing at least one non-proteinaceous catalyst for the dismutation of superoxide or at least one ligand precursor of a non-proteinaceous catalyst for the dismutation of superoxide; and c. admixing the unmodified biomaterial and the non-proteinaceous catalyst for the dismutation of superoxide or the ligand precursor.

Biomaterials modified according to this process preferably form a solution with the non-proteinaceous catalyst or ligand, although a :m to nm-sized particle mixture is also contemplated by the present invention. The above admixture process may involve heating the constituents in order to melt at least one unmodified biomaterial constituent. For instance, the PACPeD catalyst Compound 38 can be mixed with melted polypropylene at 250EC, as in Example 20. Many other polymer biomaterials melt below 300EC, such as polyethylene, poly(ethyleneterephthalate) and polyamides, and would be especially suitable for use in this melted admixture technique. After admixing, the melted modified biomaterial may be injection or extrusion molded, or spun. Temperatures above about 375EC should not be used, however, as decomposition of the catalyst may result.

Thus, metals, ceramics, and high-melt polymers should not be melted for admixture. Rather, a solvent in which at least one unmodified biomaterial and the non-proteinaceous catalyst for the dismutation of superoxide or the ligand precursor are soluble may be used when admixing these constituents. As noted above, the PACPeD catalysts are soluble in several common solvents. If the solvent method is used, the process preferably further comprises removing the solvent after admixing. Methods suitable for removing a solvent used in the present invention include evaporation and membrane filtration, although care should be taken so that the membrane filter size will retain the non-proteinaceous catalyst. As with the copolymerized modified biomaterials, the admixed modified biomaterials may be wet spun or solution cast.

More hydrophobic or hydrophilic groups may be added to the non-proteinaceous catalyst in order to change its solubility characteristics. Likewise, the non-proteinaceous catalysts may be synthesized with specific pendant groups in order to have a particular affinity for the modified biomaterial. Usually this is accomplished by choosing the non-proteinaceous catalyst used in the admixture process so that ionic or hydrophobic interactions will occur between the catalysts and the modified biomaterial. For instance, the negatively charged carboxyl group of Compound 52 would have an affinity for the positively charged calcium ions in a hydroxyapatite ceramic matrix. Similarly, the added cyclohexyl group of Compound 47, as well as the lack of pendant polar groups, would help this catalyst to integrate into polyethylene. Thus, by increasing the affinity of the non-proteinaceous catalyst for the biomaterial, one can help to prevent the dissociation of the catalyst from the modified biomaterial.

Uses of the Modified Biomaterials

The biomaterials of the present invention show greatly improved durability and decreased inflammatory response when interacting with biological systems. Thus, these biomaterials modified with non-proteinaceous catalysts for the dismutation of superoxide are ideal for use in devices for implantation or the handling of bodily fluids. Since the non-proteinaceous catalysts for the dismutation of superoxide are not consumed during the dismutation reaction, they may retain their activity indefinitely. The biocompatible article can be an article where, during its intended use, at least a portion of the article comprising the modified biomaterial is implanted within a mammal. For instance, one such application would be coating pacemaker lead wires as described in U.S. Pat. No. 5,851,227 with the modified polyureaurethane of Example 16. These improved lead wires are believed to be more durable in the body, and thus prevent the device failure which is often seen with conventional polyurethane coated wires. Similarly, a modified polyester, such as in Example 19, could be used to spin fibers for vascular graft fabric as described in U.S. Pat. No. 5,824,047. Grafts made using this fabric are believed to heal faster, as less inflammation would be caused by the biomaterial. Similarly, the modified polypropylene tested in Example 22 could be used to make surgical sutures. The biocompatible article may also be one where, during its intended use, the surface comprising the modified biomaterial is exposed to biological fluids, such as blood or lymph. For instance, a surface covalently conjugated chitosan film would be ideal for use as a membrane material in heart-lung machines which oxygenate and circulate blood during bypass operations. The copolymerized poly(etherurethane urea) of Example 16 would be useful in manufacturing the direct mechanical bi-ventricular cardiac assist device of U.S. Pat. No. 5,749,839. Use of these biomaterials in tissue engineering devices, such as scaffoldings, would be another application.

The various methods of modifying biomaterials provided by the invention allow for a wide range of practical applications. For instance, in manufacturing stents for use in angioplasty procedures, one would have the option of directly conjugating a PACPeD with a pendant silyl group with the steel of a stent manufactured as described in U.S. Pat. No. 5,800,456, through the formation of a covalent bond. Alternatively, one could copolymerize a PACPeD with pendant amine groups with a polyurethane, as in Example 16, and coat the stent with the polymer. Yet another option would be to admix a PACPeD with polypropylene, as in Example 20, extrude the mixture into a stretchable film, and shrink wrap the stent in the modified polymer film. As shown by this simple example, the diverse processes for the production of modified biomaterials using non-proteinaceous catalysts for the dismutation of superoxide allow the bio-engineer a wide variety of manufacturing techniques. A person of ordinary skill in the art of medical device design would be able to discern which modified material, and which process of modification, would be best for the medical device being produced.

The biocompatible articles of the present invention may comprise several biomaterials modified with a non-proteinaceous catalyst for the dismutation of superoxide or a ligand precursor of a non-proteinaceous catalyst for the dismutation of superoxide. This versatility will make these materials especially useful in medical devices that are subject to continual wear and stress, such as joint replacement implants. The polyethylene "socket" polymer portion of the joint which allows a lowered friction contact point in the implant could be injection molded from a copolymer with the non-proteinaceous catalyst, while the metal "ball" portion of the joint which contacts the polyethylene could be surface covalently conjugated with a non-proteinaceous catalyst. Thus, an entire device with decreased inflammatory response may be manufactured out of the modified biomaterials of the present invention, even though diverse materials are used in its construction. Another use for the modified biomaterials, mentioned in the stent example above, is coatings.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and do not limit of the remainder of the disclosure in any way whatsoever.

EXAMPLES

All reagents were used as received without purification unless otherwise indicated. All NMR spectra were obtained on a Varian VXR-300 or VXR-400 nuclear magnetic resonance spectrometer. Qualitative and quantitative mass spectroscopy was run on a Finnigan MAT90, a Finnigan 4500 and a VG40-250T using m-nitrobenzyl alcohol (NBA) or m-nitrobenzyl alcohol/LiCl (NBA+Li). Melting points (mp) are uncorrected.

Example 1

Preparation of Compounds Used in Template Synthesis

Chemicals, Solvents, and Materials.

UV Grade Acetonitrile (015-4) and Water (AH365-4) were obtained from Burdick & Jackson (Muskegon, Mich.). Isopropanol (27,049-0), R,R-1,2-diaminocyclohexane (34, 672-1), 2,6-diacetylpyridine (D880-1), 2,6-pyridinedicarboxaldehyde (25,600-5), and trifluoroacetic acid (T6508) were purchased from Aldrich (Milwaukee, Wis.). 2-(N-morpholino)-ethanesulfonic acid (475893) and its sodium salt (475894) were purchased from Calbiochem (La Jolla, Calif.).

N-(triphenylmethyl)-(1R,2R)-diaminocyclohexane:

To a solution of (1R,2R)-diaminocyclohexane (250 g, 2.19 mol) in anhydrous CH2Cl2 (3.5 L) at 0° C. was added, dropwise, a solution of trityl chloride (254 g, 912 mol) in anhydrous CH2Cl2 (2 L) over 4 h. The resulting mixture was allowed to warm to RT and stirred overnight. The reaction mixture was washed with water until the pH of the aqueous washes was below 8 (4×2 L) and dried over Na2SO4. Filtration and concentration of the solvent afforded 322.5 g (99% yield) of N-(triphenylmethyl)-(1R,2R)-diaminocyclohexane as a glass: 1H NMR (300 MHz, DMSO-d6) d 7.50 (d, J=7.45 Hz, 6H), 7.26 (app t, J=7.45 Hz, 6H), 7.16 (app t, J=7.25 Hz, 3H), 2.41 (dt, J=10.3, 2.62 Hz, 1H), 1.70 (m, 1H), 1.54–0.60 (complex m, 8H). 13C NMR (75 MHz, DMSO-d6) dc 147.2 (s), 128.4 (d), 127.3 (d), 69.9 (s), 59.0 (d), 54.4 (d), 36.6 (t), 32.5 (t), 24.6 (t), 24.3 (t). MS (LRFAB) m/z=363 [M+Li]+.

Glyoxal bisimine of N-(triphenylmethyl)-(1R,2R)-diaminocyclohexane:

To a solution of N-(triphenylmethyl)-(1R,2R)-diaminocyclohexane (322.5 g, 905 mmol) in methanol (4 L) was added glyoxal (51.9 ml of a 40% solution in water, 452.3 mmol), dropwise over 30 min. The resulting mixture was stirred for 16 h thereafter. The precipitated product was isolated by filtration and dried in vacuo to afford 322.1 g (97% yield) of the bisimine product as a white solid: 1H NMR (300 MHz, CDCl3) d 7.87 (s, 2H), 7.51 (d, J=8.1 Hz, 12H), 7.16–7.05 (m, 18H), 2.95 (b m, 2H), 2.42 (b m, 2H), 1.98–0.81 (complex m, 18H). ). 13C NMR (100 MHz, CDCl3) 161.67 (d), 147.24 (s), 147.22 (s), 128.90 (d), 128.81 (d), 127.73 (d), 127.61 (d), 126.14 (d), 73.66 (s), 70.86 (d), 70.84 (d), 56.74 (d), 32.45 (t), 31.77 (t), 24.02 (t), 23.62 (t). MS (LRES) m/z 757 [M+Na]+.

N,N'-Bis{ (1R,2R)-[2-(Triphenylmethylamino)]cyclohexyl}-1,2-diaminoethane:

The glyoxal bisimine of N-(triphenylmethyl)-(1R,2R)-diaminocyclohexane (586 g, 798 mmol) was dissolved in THF (6 L) and treated with LiBH4 (86.9 g, 4.00 mol) at RT. The mixture was stirred for 12 h at RT and treated with a second 86.9 g (4.00 mol) portion of LiBH4. The reaction was then warmed to 40° C. for 4 h thereafter. The reaction was carefully quenched with water (1 L) and the THF was removed under reduced pressure. The residual slurry was partitioned between CH2Cl2 (3 L) and water (1 additional L). The layers were separated and the aqueous layer was extracted again with CH2Cl2 (1 L). The combined CH2Cl2 extracts were dried (MgSO4), filtered and concentrated to afford 590 g (~100% crude yield) of N,N'-bis{(1R,2R)-[2-(triphenylmethylamino)]cyclohexyl}-1,2-diaminoethane as a white foam: MS (LRES) m/z 739 [M+H]+.

N,N'-Bis{(1R,2R)-[2-(amino)]cyclohexyl}-1,2-diaminoethane tetrahydrochloride:

To a solution of N,N'-bis{(1R,2R)-[2-(triphenylmethylamino)]cyclohexyl}-1,2-diaminoethane (590 g, 798 mmol) in acetone (3 L) was added concentrated HCl (1.5 L). The reaction was stirred for 2 h and concentrated. The residue was partitioned between water (2 L) and CH2Cl2 (1 L). The layers were separated and the aqueous layer was concentrated and dried in vacuo to afford 257 g (80% yield) of the tetrahydrochloride salt as a granular off-white solid: 1H NMR (300 MHz, CDCl3) 3.82–3.57 (complex m, 8H), 2.42 (d, J=9.9 Hz, 2H), 2.29 (d, J=9.3 Hz, 2H), 2.02–1.86 (complex m, 4H), 1.79–1.60 (complex m, 4H), 1.58–1.42 (complex m, 4H). 13C NMR (75 MHz, CDCl3) 59.1 (d), 51.3 (d), 40.8 (t), 29.2 (t), 26.0 (t), 22.3 (t), 22.2 (t). MS (LRFAB) m/z 255 [M+H]+. The tetrahydrochoride salt can be recrystallized or precipitated from a viscous aqueous solution by the addition of ethanol. This treatment removed all color.

Example 2

Template Synthesis of Compound 38

[Manganese (II) dichloro{(4R,9R,14R,19R)-3,10,13,20, 26-pentaazatetracyclo [20.3.1.04,9.014,19]hexacosa-1(26), 22(23),24-triene}].

In a 5-L flask N,N'-Bis {(1R,2R)-[2-(amino)]cyclohexyl}-1,2-diaminoethane tetrahydrochloride, (93.5 g, 234 mmol), was suspended in ethanol (3 L), treated with solid KOH (59.6 g of 88% material, 934 mmol), and the resultant mixture stirred at RT for 1 h. MnCl2 (anhydrous, 29.4 g, 233.5 mmol) was then added in one portion and the reaction was stirred at RT for 15 min. To this suspension was added 2,6-pyridinedicarboxaldehyde (31.6 g, 233.5 mmol) and the resulting mixture was refluxed overnight. After 16 h, the template reaction was complete: MS (LRFAB) m/z 443 [M−Cl]+. See accompanying HPLC analyses. This material was taken on to the next step "as is". The reaction mixture containing the template product in ethanol was cooled to RT and treated (cautiously under Argon flow) with 10% Pd(C) (~100 g in portions over the next 3–4 days) and ammonium formate (~200 g also in portions over the next 3–4 days). The reaction was refluxed for 4 days. HPLC and MS analysis at this time showed complete reduction. The catalyst was filtered through celite and the filtrate was concentrated to afford ca. 110 g of crude material. Recrystallization from water afforded 50.0 g of the product in crop one as a pale yellow finely divided solid. Upon sitting a second crop (12.5 g) was isolated. MS (LRFAB) m/z 447 [M−Cl]+. After drying the combined crops overnight in vacuo at 70° C., a yield of 60.1 g (54%) was obtained. Analysis calc'd for C21H35Cl2N5Mn: C, 52.18; H, 7.30; N, 14.49; Cl, 14.67. Found: C, 51.89; H, 7.35; N, 14.26; Cl, 14.55.

dark red-brown. Mass spectrometry and HPLC analyses showed that the reaction had gone to $^3$95% completion to give the bisimine Mn(II) complex (~94% purity by HPLC): ESI-MS: m/z (relative intensity) 471/473 (100/32) [M−Cl]$^+$; only traces of diacetylpyridine (~5% by HPLC) and unreacted tetraamine complex (MS) were detected. The suspension was allowed to cool to RT, and was stirred overnight. The next day, the suspension was filtered (largely KCl) and dried in vacuo at 70° C. overnight. This material may be further purified by extractive work-up as follows: 69 g of the crude bisimine were dissolved in 1.2 L of distilled water. The yellow-orange solution was extracted with $CH_2Cl_2$ (4×500 mL) and then 210 g of NaCl were added (final solution is ~15% w/v in NaCl). The resulting suspension was extracted with $CH_2Cl_2$ (4×500 mL). The combined extracts were pooled, dried over $MgSO_4$, filtered, and the solvent removed under reduced pressure. Upon drying in vacuo at 70° C. overnight, the product was isolated as an amorphous orange solid (ca. 50 g, 78% recovery) with a purity of ca. 98% by HPLC.

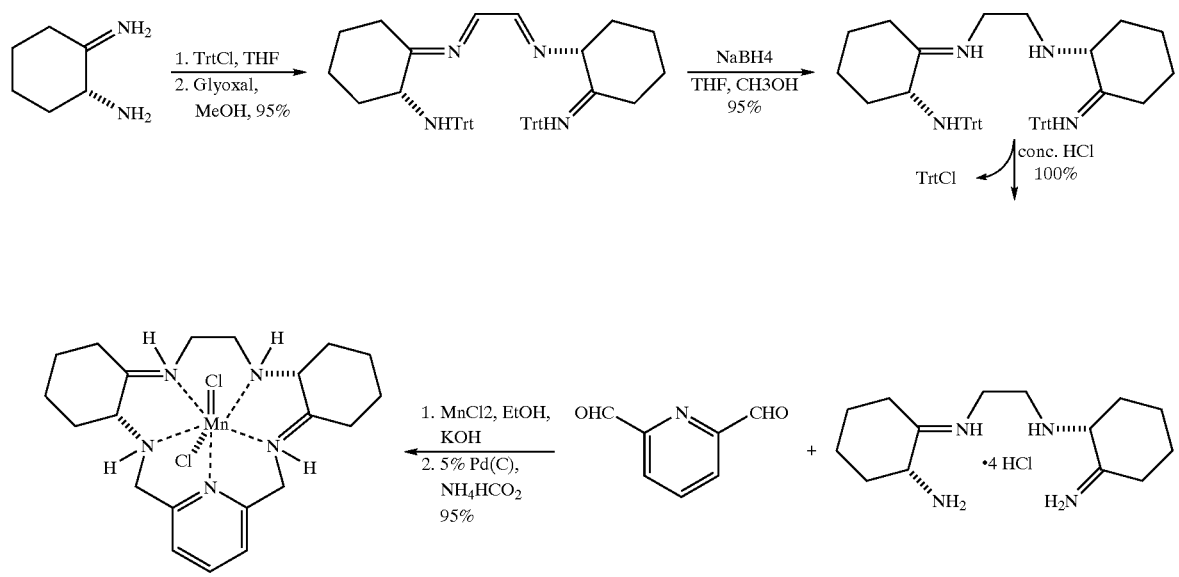

The Synthesis is Diagramed below:

Example 3

Template Synthesis of Compound 40

[Manganese(II)dichloro(4R,9R,11R,14R,19R)-3,10,13,20,26-pentaaza-(2R,21R)-dimethyltetracyclo[20.3.1.0$^{4,9}$.0$^{14,19}$]hexacose-1(25),22(26),23-triene, To a stirred solution of N,N'-Bis{(1R,2R)-[2-(amino)]cyclohexyl}-1,2-diaminoethane tetrahydrochloride (4.00 g, 10.0 mmol) in absolute ethanol (100 mL) was added KOH (2.55 g of ~88% material, 40.0 mmol) and the mixture was stirred at RT for 30 min. under an Ar atmosphere. $MnCl_2$ (anhydrous, 1.26 g, 10.0 mmol) was then added and the suspension stirred for an additional 30 min. or until $MnCl_2$ dissolved. At this point, 2,6-diacetylpyridine (1.63 g, 10.0 mmol) was added to the green mixture and after 30 minutes heating commenced. After refluxing for 5 d, the mixture was Transfer Hydrogenation with Ammonium Formate.

The purified bisimine (1.0 g, 1.97 mmol) was dissolved in 100 mL of anhydrous MeOH and the flask flushed with nitrogen while 3% Pd/C (0.5 g, 50% by weight) was added. The suspension was heated and 10 mL of a MeOH solution containing ammonium formate (1 g, 16 mmol) were added. After 30 and 60 min. of reflux, a second and third portion of formate were added (16 mmol each). The suspension was allowed to cool to RT after 2 h of reflux (at this point the supernatant was nearly colorless), filtered through celite and the solvent removed under reduced pressure. The resulting yellow-green semisolid was stirred with 50 mL of $CH_2Cl_2$ for 5–10 min., filtered, and the solvent removed once more. The remaining yellow-green foam consisted of ~95% S,S- and S,R-isomers in a 3.8:1 ratio as determined by HPLC.

The synthesis is diagramed below:

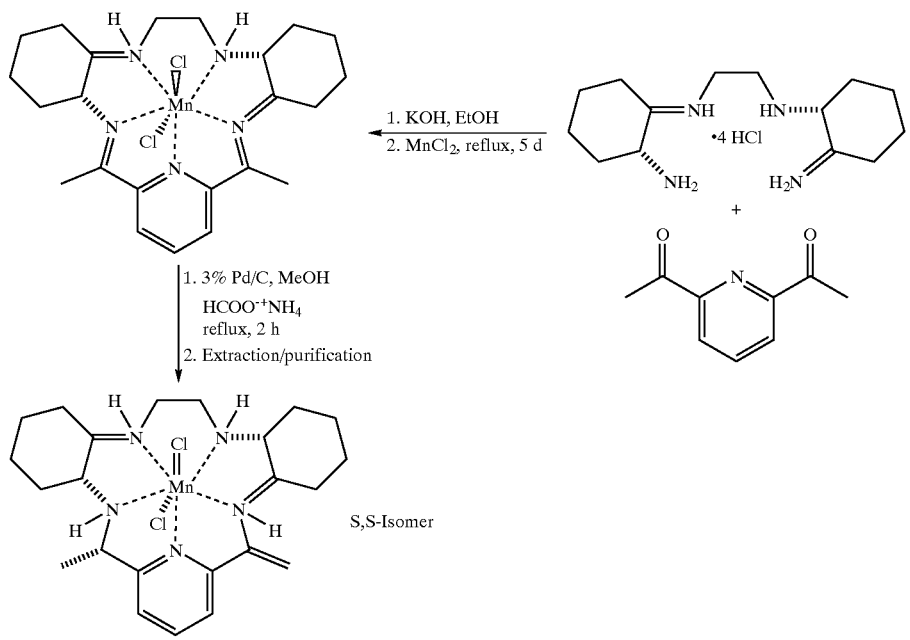

Purification Protocol.

Extraction of Comound 40 (S,S-isomer) from the Crude Mixture Obtained from Transfer Hydrogenation.

Crude product isolated after transfer hydrogenation (9.3 g) was dissolved in water (370 ml) and extracted with DCM (4×185 ml). All organic extracts and aqueous phase were analyzed by HPLC to follow the progress of extraction. Analysis was performed either in a complex form or after release of the free ligand. Recovery of R,S- and S,S-isomer from DCM (1+4, extracts from water): (2.42 g+1.18 g+1.24 g=4.84 g). After 4 extraction with DCM no R,S-isomer was detected by HPLC in aqueous phase. Then solid NaCl was added (10.82 g) to make up 0.5 M solution and S,S-complex (Compound 40) was extracted 4 times with DCM (370 ml each). Most of the S,S-isomer was extracted into the 1$^{st}$ DCM extract (purity by HPLC>94%). Impurities (others than R,S-isomer) were extracted at 4–6% level). After evaporaion of the first two DCM extracts and drying under high vacuum 3.04 g of S,S-isomer Compound 40 was obtained with purity 94%. The product was further purified by HPLC using YMC C18 column or by flash chromatography over C18 silica gel column.

Purification by Preparative HPLC

Compound 40 (200 mg) obtained from extraction (purity 91%) was dissolved in water (1.0 ml) and applied onto YMC CombiPrep column (20 mm×50 mm, ODS AQ 5 um 120A). The product was eluted using gradient—B 10 to 50% in 10 min, where A: 0.5M NaCl and B: Acetonitrile-Water (4:1), flow rate 25 ml/min, detection at l=265 nm. Fractions with purity >99% (8 to 20, each 5 ml) were combined and the solvents were evaporated to dryness. The residue was partitioned between 6 ml water and 10 ml of DCM. Seperated layers, extracted aqueous layer with 3×10 ml DCM. Combined DCM layers, dried over $Na_2SO_4$, filtered and evaporated solvents to off-white foam, Obtained 97 mg, 48%. ESMS m/z 475 [M–Cl]$^+$ Calcd for $C_{23}H_{39}Cl_2N_5Mn$.

Purification of Compound 40 by Flash Chromatography Over C18 Silica Gel 40 g of Bakerbond Octadecyl $C_{18}$ packing was packed into a 25 mm×130 mm column. Column was equilibrated with $CH_3CN$ (300 ml), 1:1=$H_2O$:$CH_3CN$ (200 ml), 15% $CH_3CN$ in $H_2O$ (200 ml) and 15% $CH_3CN$ in 0.5 M NaCl (200 ml). Compound 40 (1 g) obtained from extraction (purity 94% by HPLC) was dissolved in 3 ml of $H_2O$ and applied onto the column. The product was eluted with 15% CH3CN in 0.5M NaCl. Fractions were analyzed by HPLC. HPLC conditions were as follows: YMC $C_{18}$ column, 3 ml/min, l=265 nm, B=10–50% in 9 min, where A=0.5 M NaCl in $H_2O$ and B=$CH_3CN$:$H_2O$=4:1. The S,S-isomer eluted in fractions 51–170. Fractions with purity >95% (80–170) were combined and the solution was concentrated to 80 ml and extracted 2× with DCM. (40 ml each). Obtained 0.64 g (yield 64%) of the S,S-isomer (Compound 40), 100% pure by HPLC ESMS m/z 475 [M–Cl]$^+$ Calcd for $C_{23}H_{39}Cl_2N_5Mn$.

Example 4

Template Synthesis of Compound 42

Synthesis of 4-chloro-2,6-pyridinedicarboxaldehyde.

4-Chloro-2,6-dicarbomethoxypyridine:

Anhydrous chelidamic acid (230 g, 1.14 mol) was partially dissolved in CHCl3 (2 L) while stirring under N2. Then, over a period of 3 h, PCl5 (1,000 g, 4.8 mol) was added as a solid to the cream-colored suspension. Considerable gas evolution occurred with each solid addition. After 17 h, the white mixture was heated to reflux and a light yellow solution resulted within an hour. Seven hours later, heating was discontinued. The light suspension was treated with MeOH (1.25 L), added dropwise over 6.5 h. Then, after gas evolution had ceased, the solution was concentrated under reduced pressure and the off-white slurry that formed added to deionized water and vacuum-filtered. The residue was washed with more water (~5 L) until the pH of the filtrate was neutral. The residue was dried overnight in vacuo at 50–60° C. to afford 4-chloro-2,6-dicarbomethoxy-pyridine as white needles (175 g, 66%); m.p. 132–134 ° C. 1H-NMR is consistent with the structure.

4-Chloro-2,6-pyridinedimethanol:

The methyl ester prepared as above (675 g, 2.94 mmol) was partially dissolved in MeOH (16 L) and stirred under N2 with cooling in an ice bath. NaBH4 (500 g, 13.2 mol) was added as a solid in portions over the next 20 h. Over the course of 48 h, the reaction went from orange to red to yellow-green. Then, the temperature was allowed to reach RT overnight. After this period, the mixture was refluxed for 16 h, then cooled over 6 h to afford a clear yellow-green solution. Acetone (3.1 L) was added over 1.5 h, then the yellow solution was refluxed for 2 h. Concentration under reduced pressure yielded an amorphous light yellow gum. The gum was taken up in saturated Na2CO3 and heated to ~80 ° C. for 1 h. Upon cooling overnight, the viscous yellow supernatant was separated from the white precipitate by vacuum filtration. The solid was washed with CHCl3 (350 mL), then taken in THF (4.5 L) and refluxed for 30 min., then filtered. The filtrate was concentrated under removed pressure, the solid residue washed with CHCl3, then dried in vacuo overnight to afford the diol product (375 g, 68%) as a white solid. 1H-NMR is consistent with the structure.

4-Chloro-2,6-pyridinedicarboxaldehyde:

A solution of oxalyl chloride (110 mL, 1.27 mol) in CH2Cl2 (575 mL) was cooled to –60 ° C. and stirred under N2. To this solution was added a solution of dimethylsulfoxide (238 mL, 3.35 mol) in CH2Cl2 (575 mL) via cannula. Addition proceeded with vigorous gas evolution and a mild exothermic reaction over 1.5 h. After stirring for 10 min. a solution of the diol (100 g, 0.58 mol) in DMSO (288 mL) was added via cannula over a period of 30 min. The previously yellow solution turned into a suspension. After 2 h at –60 ° C., Et3N (1.5 L) was added dropwise over 1 h. After addition was complete and 30 min. had passed, the mixture was poured over water (2 L), shaken and allowed to settle. The organic layer was separated and the aqueous layer extracted with CH2Cl2 (4×300 mL). The combined CH2Cl2 layers were dried over MgSO4 and concentrated under reduced pressure to afford a combination of gray-yellow solid and a reddish liquid. The dark yellow solid was collected by filtration using Et2O to rinse out. This material was dissolved in 1L of CH2Cl2 and passed through a bed of SiO2 (~800 cm3) eluting with more CH2Cl2. A total of 65 g (67%) of the dialdehyde product were collected in this fashion. 1H-NMR is consistent with the structure.

Preparation of 4-chlorobisimine by Template Cyclization.

Bis-R,R-Cyclohexane tetraamine.4HCl (2.57 g, 6.42 mmol) was suspended in absolute EtOH (64 mL) and stirred under Ar. Pellets of KOH (1.65 g of 87.4% material, 25.68 mmol) were added and the suspension stirred for 30 min. until the pellets dissolved. After this period, MnCl2 (anhydrous, 0.806 g, 6.42 mmol) was added and allowed to stir for 1–2 h until the suspension turned greenish and all the MnCl2 dissolved. 4-Chloro-2,6-pyridinedicarboxaldehyde (1.09 g, 6.42 mmol) was added as a solid and the mixture stirred at room temperature for 30 min., then heated to reflux. The suspension gradually turns red-orange and after 48 hours it was cooled to room temperature. The mixture was filtered through a 10 m pore-size funnel and the solvent removed under reduced pressure to yield the desired product (3.47 g, 105%, contains some inorganic salts) as a red-orange solid.

NaBH4 Reduction.

The bis-imine complex (1.89 g, 3.68 mmol) was dissolved in anhydrous MeOH (50 mL) and stirred under Ar in an ice-water bath. Solid NaBH4 (0.278 g, 7.36 mmol) was added in one portion resulting in gas evolution. After 30 min., an additional portion of NaBH4 (7.36 mmol) was added and the mixture allowed to warm to RT, and stirred overnight. A third portion of NaBH4 (7.36 mmol) was added at 0EC, then the mixture allowed to warm and stirred overnight. After this period, MS still showed starting material remaining. A fourth, fifth, and sixth portion of NaBH4 (7.36 mmol each) were added with 2 hours passing in between addition.

After 24 h at RT, the lightly colored solution was carefully added onto 100 mL of saturated NaCl solution, and MeOH removed under reduced pressure. CH2Cl2 (100 mL) was added and the aqueous layer extracted (2×). The organic layer s were combined, dried over MgSO4, filtered and the solvent removed to afford, upon drying in vacuo, 2.1 g of crude material (60% product by HPLC). This material was purified by SiO2 flash chromatography using 1 à 3% MeOH: CH2Cl2 as eluent. Selected fractions yielded 0.77 g (40%) of HPLC-homogeneous material. ESI-MS: m/z (relative intensity) 481/479 (100/32) [M−Cl]+; and 223/221 (100/32) [M−2Cl]2+.

The Synthesis is Diagramed below:

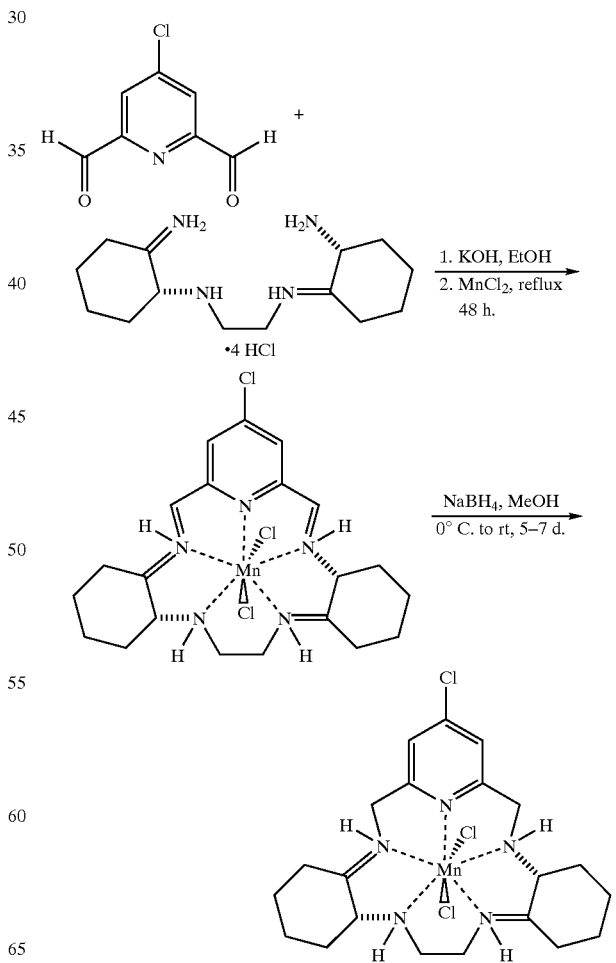

Example 5

Synthesis of Compound 43 from Compound 42

To a solution of 1.2% (w/v) 2-mercaptoethylamine (1 eq) in ethanol at 0° C. was added sodium ethoxide (1.1 eq) to generate the thiolate. After stirring for 1.75 h, the thiolate solution was added dropwise to a solution of 1.3% (w/v) SC 74897 (1 eq) in DMF at 0° C. The reaction mixture was allowed to stir overnight. The solvent was removed in vacuo, the product mixture was extracted with methylene chloride, and concentrated down in vacuo. Flash column chromatography using methylene chloride:methanol (9:1) as the eluent was used for purification, which was monitored via HPLC.

The synthesis is illustrated below:

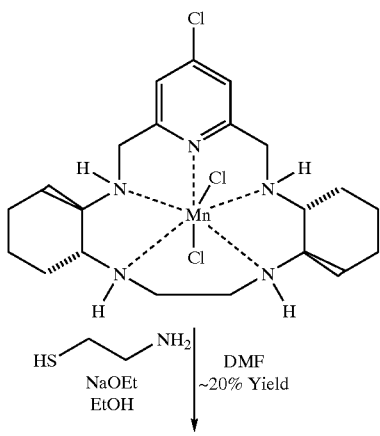

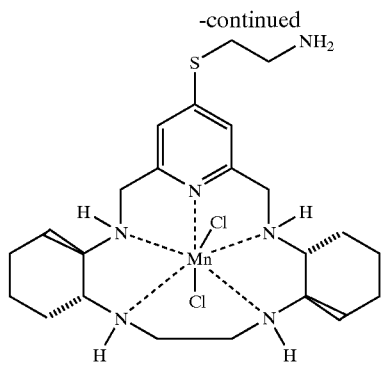

Example 6

Catalytic Hydrogenation of the Bisimine

Transfer Hydrogenation with Ammonium Formate.

The purified bisimine (1.0 g, 1.97 mmol) was dissolved in 100 mL of anhydrous MeOH and the flask flushed with nitrogen while 3% Pd/C (0.5 g, 50% by weight) was added. The suspension was heated and 10 mL of a MeOH solution containing ammonium formate (1 g, 16 mmol) were added. After 30 and 60 min. of reflux, a second and third portion of formate were added (16 mmol each). The suspension was allowed to cool to RT after 2 h of reflux (at this point the supernatant was nearly colorless), filtered through celite and the solvent removed under reduced pressure. The resulting yellow-green semisolid was stirred with 50 mL of $CH_2Cl_2$ for 5–10 min., filtered, and the solvent removed once more. The remaining yellow-green foam consisted of ~95% S,S- and S,R-isomers in a 3.8:1 ratio as determined by HPLC.

| | | | | % Area by HPLC[d] | | | | |
|---|---|---|---|---|---|---|---|---|
| Concentration (nM)[a] | Catalyst (% Pd.C)[b] | % by Weight | Time (hours) | Free Ligand | Monoimine | SS-isomer | SR-isomer | Ratio |
| 20 | 10 | 50 | 2 | — | — | 68 | 32 | 2.13 |
| 20 | 5 | 50 | 2 | 2 | — | 75 | 23 | 3.26 |
| 20 | 5 | 10 | 4 | 2 | 7 | 64 | 27 | 2.37 |
| 20 | 3 | 50 | 2 | 2 | 2 | 75 | 21 | 3.57 |
| 50 | 3 | 50 | 2 | 4 | — | 70 | 25 | 2.80 |
| 100 | 3 | 50 | 2 | 9 | <1 | 64 | 26 | 2.46 |

[a]Solvent is anhydrous MeOH.
[b]Available from Aldrich.
[c]Reflux time.
[d]Conditions: 3 mL/min. 10–50% B over 9 min. is (8:2 v/v) MeCN: water, A is 0.5N aq. NaCl. UV-detection at 265 nm.

Example 7

Conjugation of Polyethylene Terephthalate with a PACPeD Catalyst

A. Denier Reduction (Alkaline Hydrolysis) of Poly(ethylene Terephthalate) (PET) Film

20 mm×50 mm×5 mm PET film (37% crystallinity) pieces were cleaned by mixing for 30 min in a 1% (w/w) aqueous $Na_2CO_3$ solution (250 mL) at 75° C. The film pieces were removed and washed 30 min in water (HPLC grade, 250 mL) at 75° C. The pieces were next hydrolyzed for 30 min in a 0.5% (w/w) aqueous NaOH solution (250 mL) at 100° C. The film pieces added to a 1.2% (w/w) aqueous conc. HCl solution (250 mL) at room temperature. Finally, the film pieces were thoroughly rinsed in a stream of water (HPLC grade) at room temperature and dried to constant weight in vacuo.

B. Preparation of the Acid Chloride

A magnetic stir bar and anhydrous acetonitrile (50 mL) were added to a dry 100 mL round bottom flask. To the stirring solvent was added one piece of hydrolyzed film, pyridine (0.078 g, $9.89 \times 10^{-4}$ mol), and thionyl chloride (0.167 g, $1.4 \times 10^{-3}$ mol). After stirring for 24 h at room temperature, the film was removed and thoroughly rinsed in fresh acetonitrile. After drying to constant weight in vacuo, elemental analysis showed the presence of chlorine in the film.

C. Reaction with Amino Functional PACPeD

A magnetic stir bar and anhydrous acetonitrile (50 mL) were added to a dry 100 mL round bottom flask. Amino functional Compound 43 (0.138 g, $1.86 \times 10^{-4}$ mol) was added. Once in solution, the film step Bwas added and the reaction mixture was heated to reflux. After 24 h at reflux, the film was removed and rinsed in fresh acetonitrile before drying to constant weight in vacuo. ICAP analysis of the film revealed the presence of manganese.

The conjugation scheme is illustrated by the following:

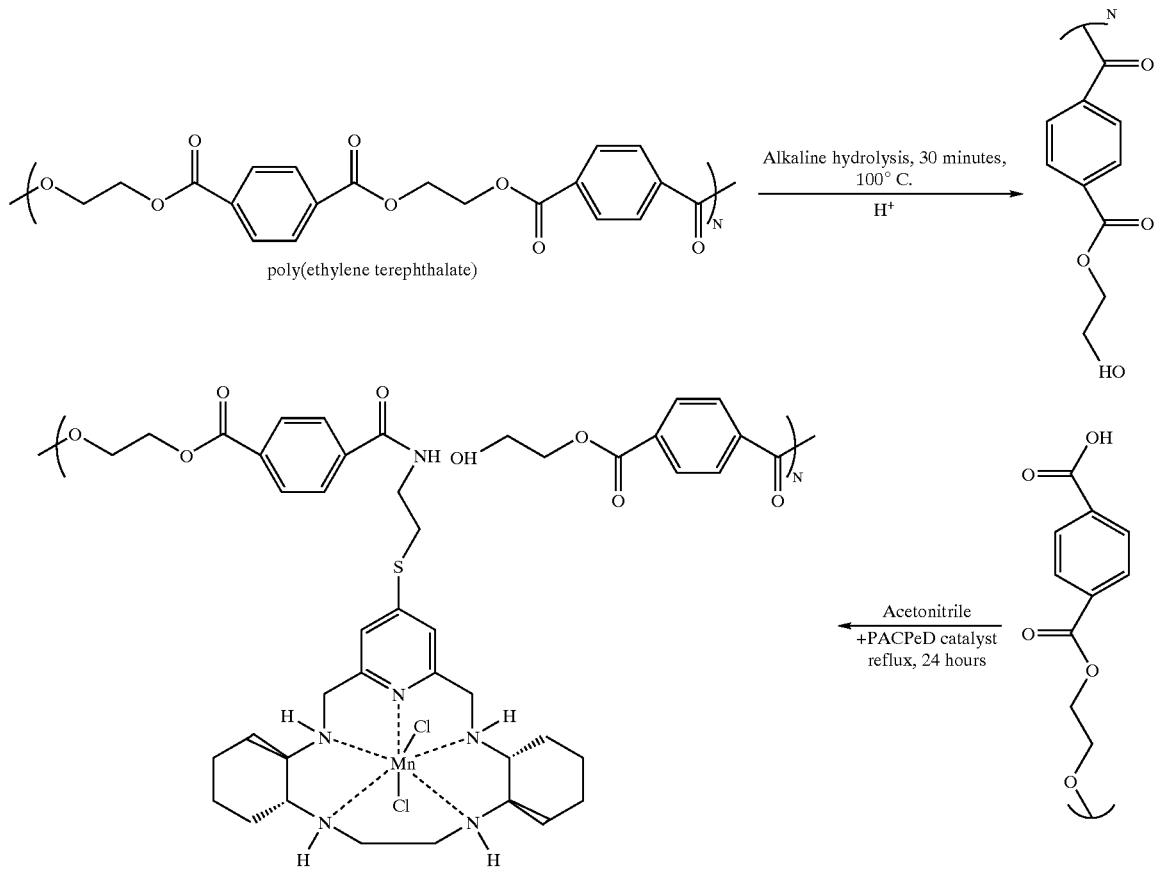

Example 8

Conjugation of Acrylic Acid Modified Polyethylene with a PACPeD Catalyst

A. Grafting of Acrylic Acid to PET Films

Pieces of 20 mm×50 mm×5 mm PET film (37% crystallinity) were used without cleaning. Film pieces were swollen in 80° C. 1,2-dichloroethane for 1 h. The films were then dried to constant weight in vacuo.

Swollen film pieces were added to a 0.08 M benzoyl peroxide in anhydrous toluene solution (125 mL). After mixing for 1 h at room temperature, the film pieces were removed, rinsed in fresh anhydrous toluene, and dried to constant weight in vacuo.

Next, the films were immersed in a 30 mL vial containing a 2 M acrylic acid (freshly distilled) and 0.1 mM Mohr's salt $\{(NH_4)_2Fe(SO_4)_2 \times 6\ H_2O\}$ aqueous solution (25 mL). The vial was purged with nitrogen, sealed, and immersed in an 80° C. oil bath. The film pieces were stirred for 20–24 h at 80° C. before removal and rinsing for several minutes in hot running tap water followed by a stream of room temperature water (HPLC grade). After drying overnight in vacuo, the acrylic acid grafted films were immersed for 5 h in boiling water (HPLC grade) and dried to constant weight in vacuo.

Preparation of the Hydrolyzed PET Film and Conjugation with the PACPeD Catalyst Proceeded as Described in Example 7.

The Conjugation Scheme is Illustrated by the Following:

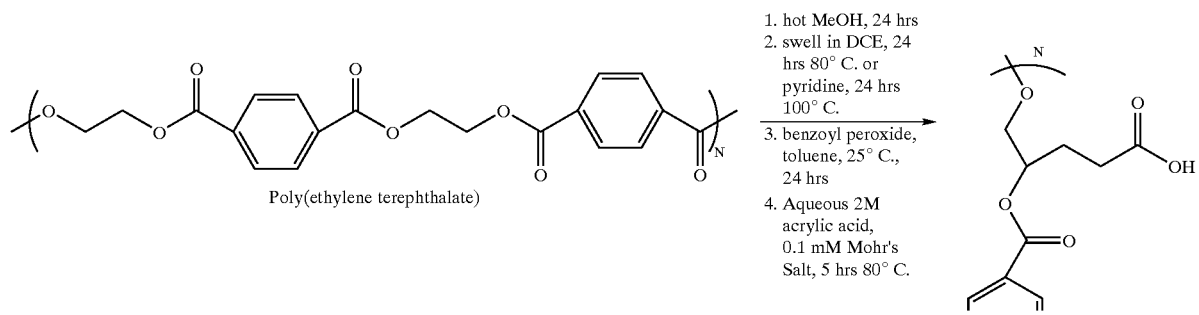

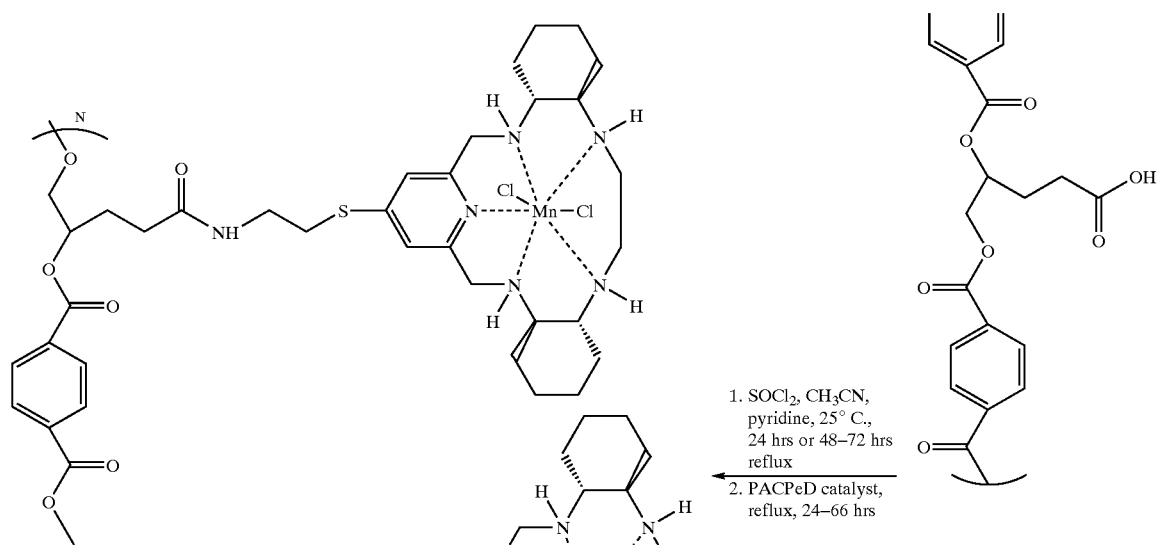

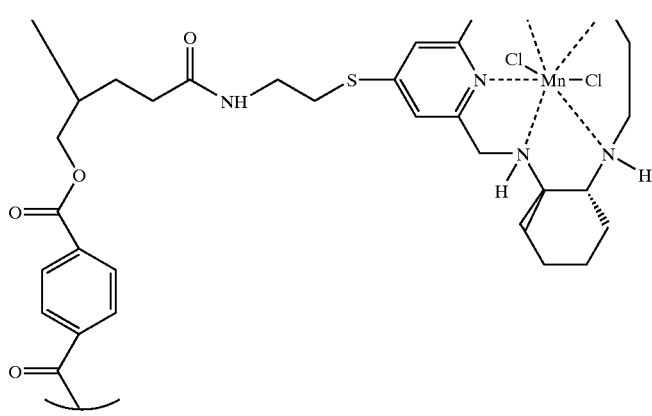

Poly(ethylene terephthalate) with surface bound PACPeD catalyst

Example 9

Surface Covalent Conjugation of Compound 43 with Poly(etherurethaneurea)

The poly(etherurethaneurea) (PEUU) ($M_n$=50,000) used for conjugation was a segmented block copolymer consisting of methylene di(p-phenyl isocyanate) (MDI), ethylene diamine, and poly(tetramethyleneglycol) (PTMG, $M_n$=2000). The ethylene diamine chain extended MDI makes up the hard segment and the PTMG makes up the soft segment. PEUU films were solvent cast from a solution of 20% PEUU in N,N-dimethylacetamide (DMAC) and allowed to dry under nitrogen for ~2 days. Films were further dried in vacuo before being cut into ~5 mm diameter disks of ~0.3 mm thickness.

PEUU disks were functionalized in a solution of 5.4% (w/v) HMDI in anhydrous toluene with triethyl amine added to serve as the catalyst. The reaction was allowed to stir at 55–60° C. for 24 h, the disks were thoroughly washed with anhydrous toluene, and dried. Disks were added to a solution of 0.3% (w/v) Compound 43 in anhydrous toluene and allowed to stir at 55–60° C. for 24 h. The disks were washed with toluene, methanol, and water to remove any unbound SOD mimic prior to implantation. By inductively coupled argon plasma analysis (ICAP, Galbraith Laboratories, Knoxville, Tenn.) of manganese there was 3.0% catalyst by weight.

To obtain a lower concentration of Compound 43, a solution of 0.7% (w/v) HMDI in anhydrous toluene (15 h) and a solution of 0.1% (w/v) Compound 43 in anhydrous toluene (24 h) was used. ICAP analysis of manganese indicated 0.6% Compound 43 by weight.

Example 10

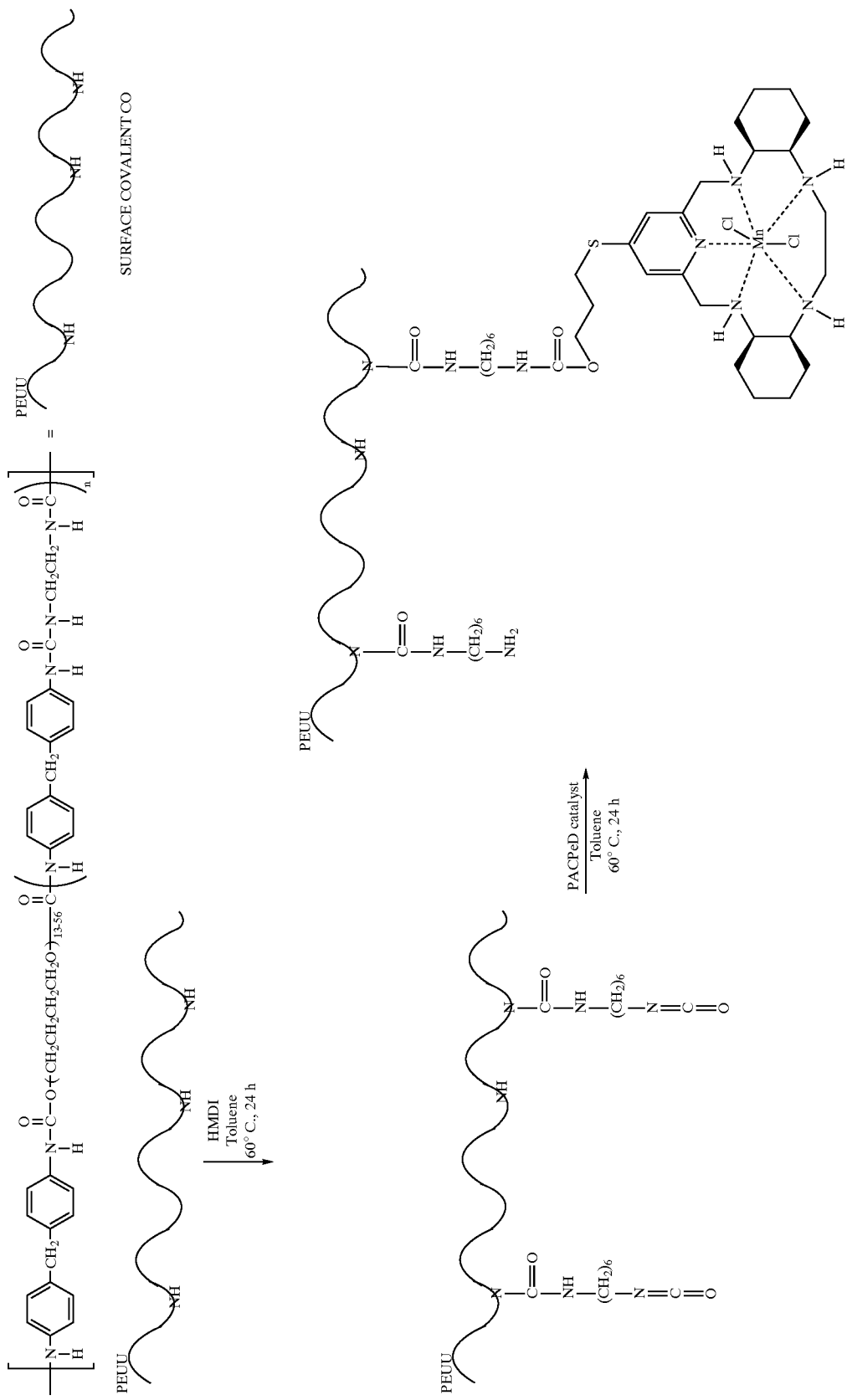

Njugation of Compound 43 and Poly(ethylene Acrylic Acid)

UHMWPE was melt blended with poly(ethylene-co-acrylic acid) in a ratio of 7:3 in a DACA twin screw at 175° C. Blends were cryoground and melt pressed into films with 5000 psi at 175° C. for 10 minutes. Films were cut into 5 mm diameter disks of ~0.5 mm thickness.

PE disks were chlorinated in a solution of 0.2% (w/v) thionyl chloride in acetonitrile. Pyridine was added to scavenge the HCl formed. The mixture was allowed to stir overnight, the disks were filtered, washed thoroughly with acetonitrile, and dried. Chlorinated disks were added to a solution of 0.1% (w/v) Compound 43 in acetonitrile, heated to reflux for 4 hours, and allowed to react at room temperature overnight. The disks were filtered and washed with acetonitrile and water. ICAP analysis for manganese indicated 1% Compound 43 by weight.

To obtain a lower concentration of Compound 43, the chlorinated disks were added to a solution of 0.02% (w/v) Compound 43 in DMSO and heated at 60° C. overnight. The disks were filtered and washed repeatedly with methanol and water. ICAP analysis for manganese indicated 0.06% Compound 43 by weight.

The synthesis is diagramed below:

Example 11
Surface Covalent Conjugation of Compound 52 with Poly(ethylene-co-acrylic Acid) via a PEO Linker To a flask under a $N_2$ purge was added polyethyene-co-polyacrylic acid (0.4 g) (15% acrylic acid by weight), DMSO (100 mL), and EDC (0.3192 g). The mixture was allowed to stir for 1 h, then polyoxyethyelene bisamine (amino-PEO) (2.65 g) (Sigma, MW=3400) was added. The mixture was allowed to stir overnight. The mixture was precipitated with water and dried in vacuo yielding 0.37 g of white powder. The powder was 1.9% N by weight as determined by elemental analysis.

To a flask under a $N_2$ purge was added EDC (0.0112 g), Compound 52 (0.031 g), and $CH_2Cl_2$. The solution was allowed to stir for 2 h at room temperature and then the amino terminated PEO functionalized polyethyene-co-polyacrylic acid (0.2 g) was added and the solution was allowed to stir overnight. Methanol (50 mL) was added to the solution, the precipitate was filtered off, washed with methanol and water, and dried in vacuo overnight. By ICAP analysis, 0.26% of manganese by weight was present.

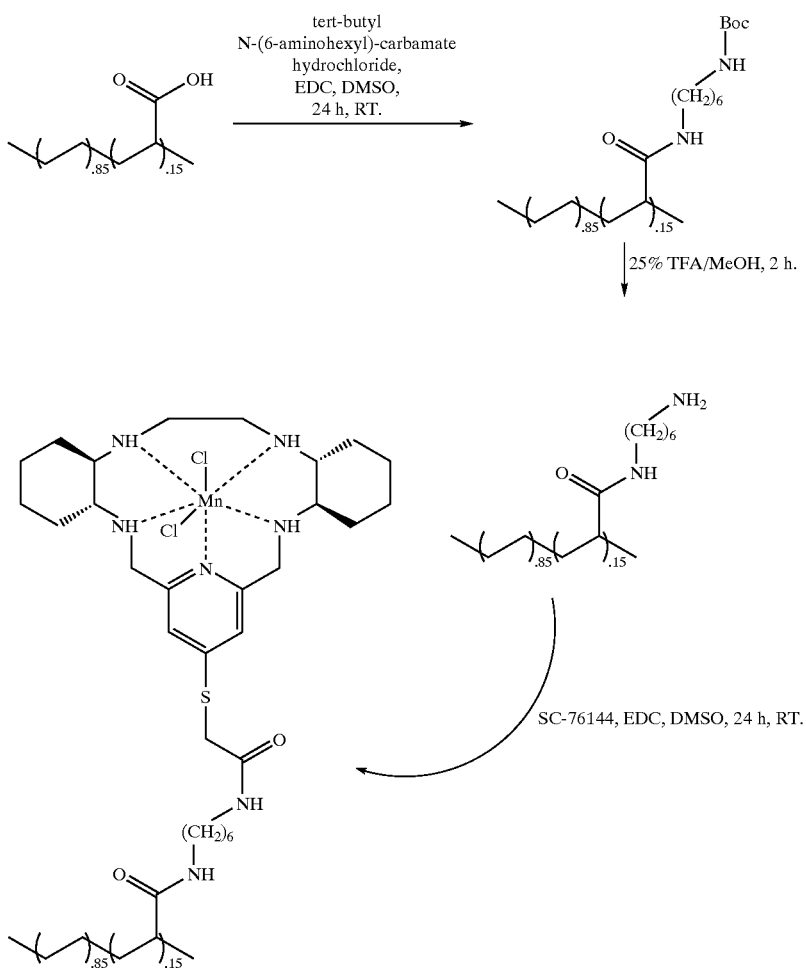

The Synthesis is Diagramed below:

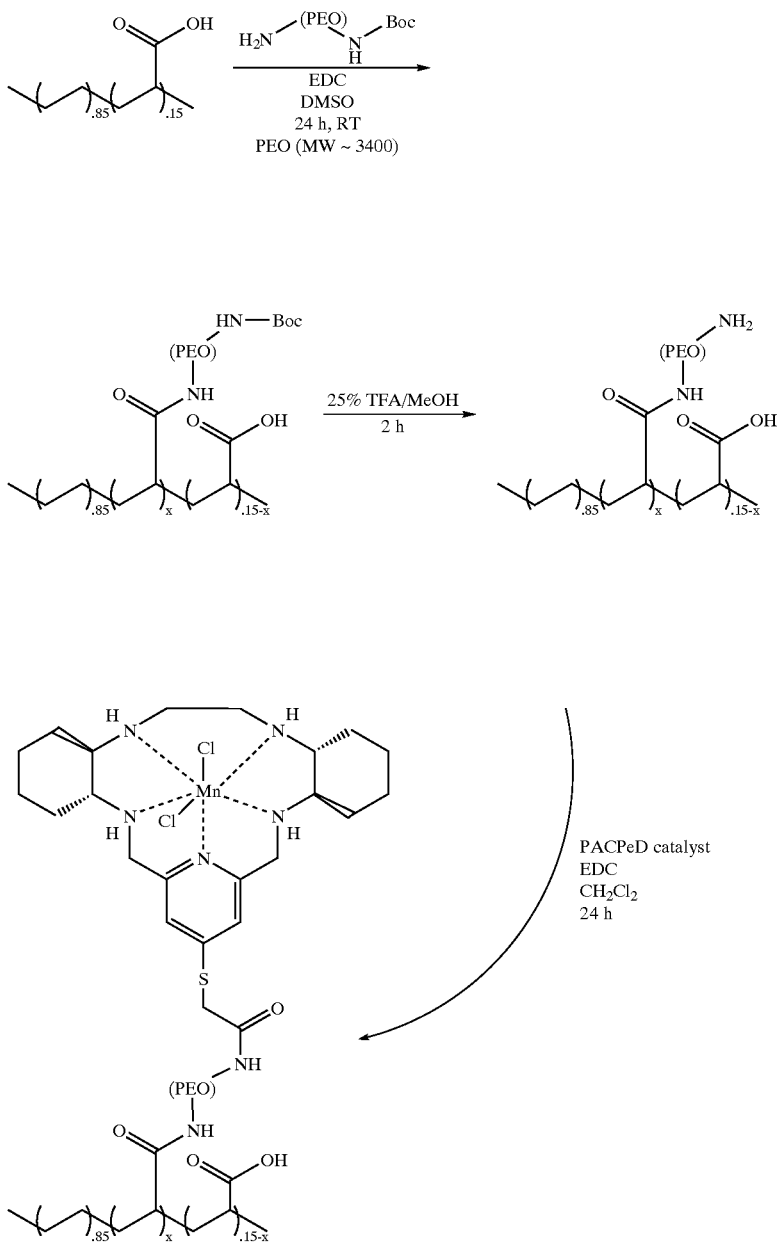

Example 12

Surface Covalent Conjugation of Compound 43 with Poly(etherurethane Urea) Coated Tantalum To a 0.5% (w/v) PEMP solution in DMAC was added 3-isocyanatopropyl triethoxysilane (3% w/v) and triethyl amine. The reaction mixture was heated to 55–60° C. for 18 h and then precipitated with ethanol, filtered, and dried. A solution of 1% (w/v) polymer in DMAc was formed. To the oxidized tantalum disks was added polymer solution and water (50:1, v:v). After agitation for 24 h, the disks were cured at 110° C. for 1 h, rinsed with DMAc, and dried. Half of the disks were set aside for use as controls during implantation. To the PEUU coated disks was added a solution of 5% (w/v) HMDI in anhydrous toluene and allowed to react at 55–60° C. for 24 h. After washing with anhydrous toluene and drying, a solution of 1% (w/v) Compound 43 in 1,1-dichloroethane was added and allowed to react for 24 h at 55–60° C. The disks were then washed with 1,1-dichloroethane, methanol, and water. After drying, ESCA was obtained and indicated a 1.2% atomic fraction of manganese on the surface.

The Synthesis is Diagramed below:

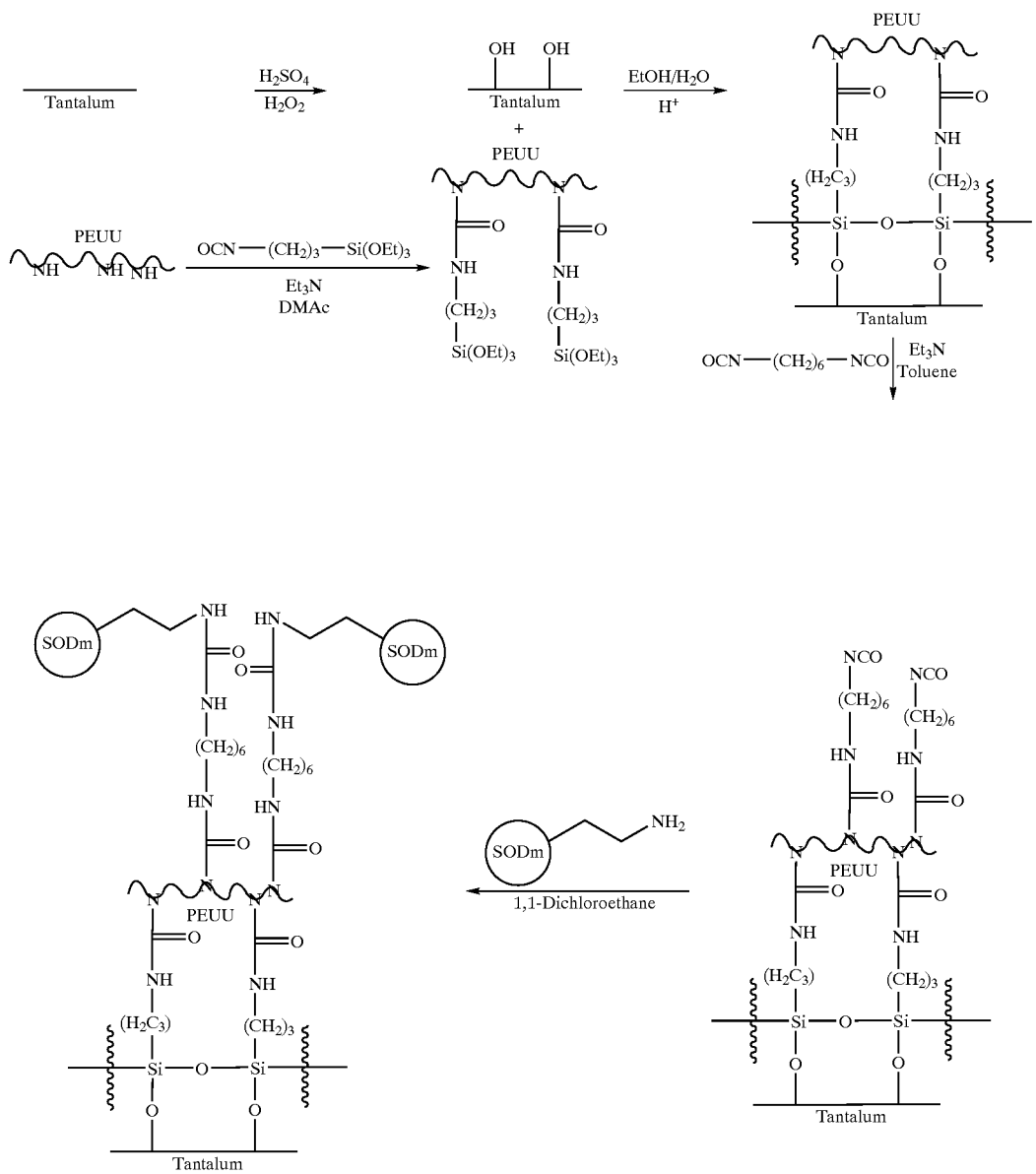

Example 13

Surface Covalent Conjugation of Compound 43 with Tantalum

Disks with a diameter of 6 mm were punched out from 0.25 mm thick tantalum sheets and the edges smoothed.

Tantalum disks were initially oxidized using a $H_2SO_4$: 30% $H_2O_2$ (1:1, v:v) solution. 3-isocyanatopropyl triethoxysilane (2% w/v) was added to an ethanol-water solution (0.8% water by weight) of pH=5 (adjusted with acetic acid) and agitated for 5 min. To the oxidized tantalum disks was added the silane and after agitation for 10 min. the disks were quickly rinsed with ethanol, and cured at 110° C. for 1 h. Half of the disks were set aside for use as controls during implantation. To the polysiloxane layered disks was added a solution of 0.5% (w/v). Compound 43 in DMAc and allowed to react at 60–65° C. for 24 h. After washing with DMAC and drying, one disk was studied by electron scanning for chemical analysis (ESCA), which indicated a 0.5% atomic fraction of manganese on the surface.

The synthesis is diagramed below:

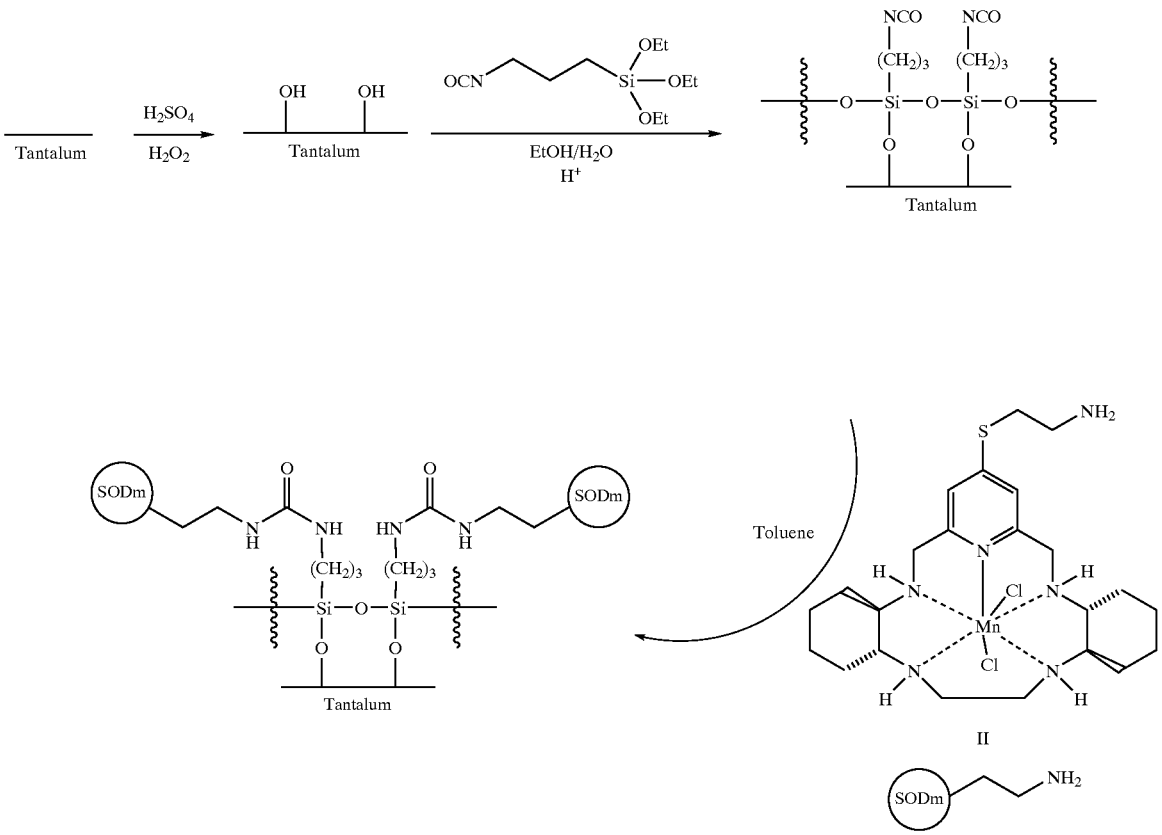

Example 14

Surface Covalent Conjugation of Compound 43 with Collagen

To a flask 0.5 g of bovine collagen (insoluble, type I from Achilles tendon) was suspended in a 4% solution of 1,4 butanediol diglycidyl ether in a buffer solution. The solution was stirred overnight. The solution was then centrifuged for about 10 minutes, and the supernatent was decanted. Any residual, adsorbed diglycidyl ether was removed from the above partially cross-linked collagen by repeated washings with methanol. At this point, the washed collagen was immersed in a solution of Compound 43 (100 mg in 50 ml) of the same buffer used in the reaction set-forth above. The contents were stirred at ambient temperature in a round bottomed flask overnight. At the end of this period, the contents were centrifuged and washed as in the earlier step to remove any unreacted Compound 43. The recovered collagen (0.304 g) was dried overnight in a vacuum oven at a temperature of 50° C.

ICAP analysis indicated 0.18% Mn in the collagen corresponding to 1.83% binding of Compound 43.

Example 15

Surface Covalent Conjugation of Compound 43 with Hyaluronic Acid

To a solution of 0.05 g of sodium salt of hyaluronic acid (Sigma H53388, Mol.Wt., $1.3 \times 10^6$) in 16.7 ml distilled water was added 0.070 g of Compound 43 and the pH of the solution lowered from 9.3 to 6.8 by careful addition of 0.1M HCl. A solution of 1-(3-Dimethylaminopropyl)-3-ethylcarbodiimide hydrochloride,[EDC.HCl] (0.012 g) and 1-Hydroxy-7-azabenzotriazole [HOAT] (0.009 g) in dimethylsulfoxide(DMSO)-water (0.5 ml; 1:1, v/v) was added and the pH was adjusted from 5.2 to 6.8 and maintained at 6.8 by incremental additions of 0.1 M sodium hydroxide. The contents were stirred overnight at ambient temperature. After 20 hr, the pH was readjusted to 6.8 from 6.94 and again stirred overnight for a total of 48 hr. At the end of this period, pH of the solution was again adjusted to 7.0 and dialyzed in Pierce Slide-a-dialyzer cassettes (Mol.Wt. cuttoff:10,000) against distilled water for 65 hr. Dialyzed contents from the cassettes were syringed out (16.7 ml) and 0.8 g of NaCl was added to obtain a 5% salt solution. The reaction product was precipitated by the addition of ethanol (×3 to 48 ml). The cotton-like white solid was recovered by filtration, dried under vacuum overnight. A total of 0.0523 g of the isolated product on ICAP analysis showed a 0.21% Mn corresponding to 2.1% binding of Compound 43 to hyaluronic acid.

The Synthesis is Diagramed below:

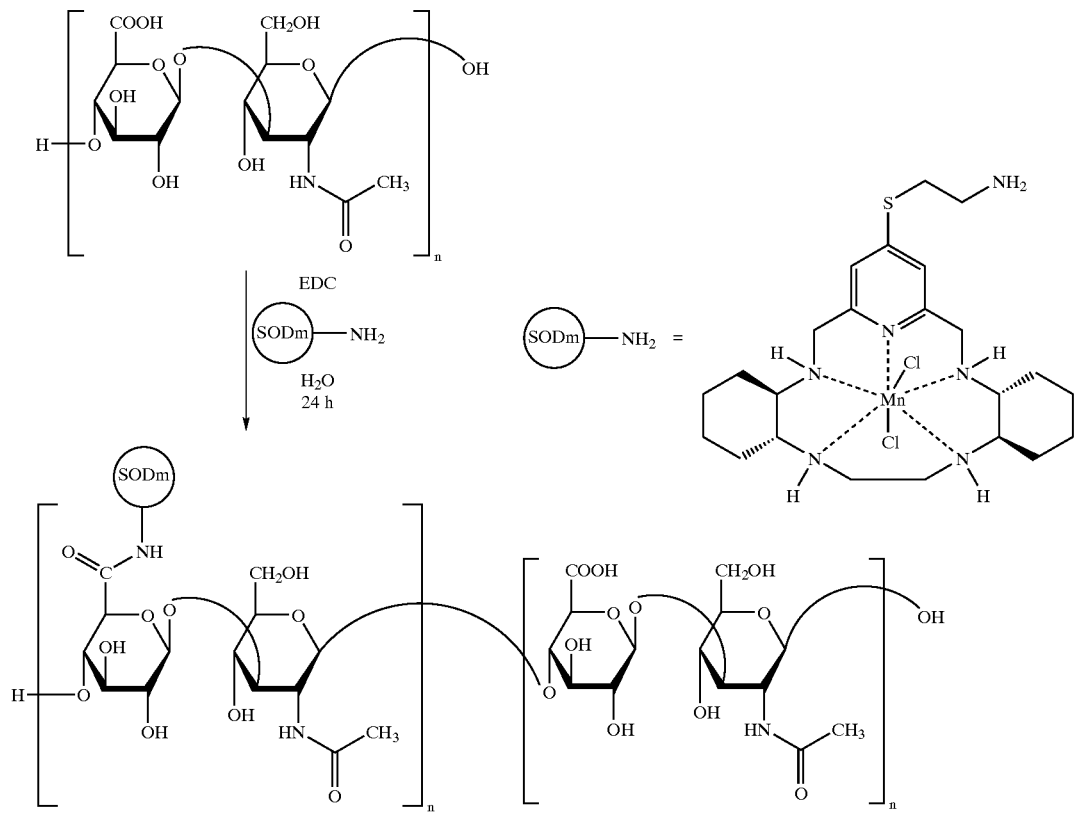

Example 16

Copolymerization of Compound 16 with Polyureaurethane

A solution of vacuum distilled 4,4'-methylenebis(phenylene isocyanate) (MDI) is prepared in N,N'-dimethylacetamide (DMA). Polytetramethylene oxide (PTMO), dehydrated under vacuum at 45–50°C for 24 h and stannous octoate catalyst are subsequently added to the stirred MDI solution at room temperature. The concentration of the reactants in solution is about 15% w/v and of the catalyst is 0.4–0.5% by weight of the reactants. After reacting at 60–65EC for 1 h, the mixture is cooled to 30EC. Ethylene diamine (ED) and diamino Compound 16 are then added and the temperature gradually brought back to 60–65°C. This is to prevent an excessively rapid reaction of the highly reactive aliphatic amine groups with isocyanates. The reaction is continued for an additional hour at about 65EC. The entire synthesis is carried out under a continuous purge of dry nitrogen. Molar ratios of MDI, ED, SODm, and PTMO and the molecular weight of PTMO are varied to produce polureaurethanes of varying hardness. The polymers are precipitated in a suitable non-solvent like methanol and dried in a vacuum oven at 70–75EC for about a week. Films for physical testing and implantation in rats are prepared by a conventional spin-casting technique followed by vacuum drying at 70EC for 4 days.

The Polymer Produced by this Method is Represented Diagrammatically below:

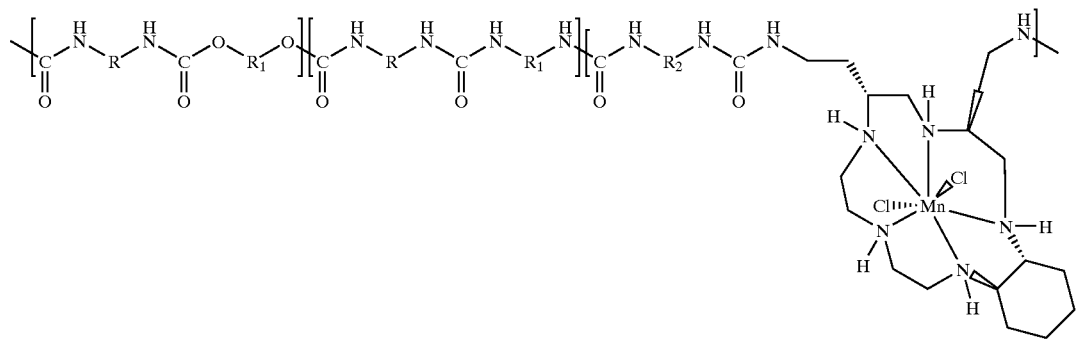

Example 17

Copolymerization of Compound 53 with Methacrylic

Synthesis of Methacryl Functional SODm:

A ~10 percent (w/v) solution of hydroxy (or amino) functional PACPeD in 1,2-dichloroethane is placed in a three necked flask equipped with a stirrer, a dropping funnel and a reflux condenser. To this solution, a ~10 percent (w/v) solution of methacryloyl chloride in 1,2 dichloroethane is added dropwise at 0°C followed by pyridine. The mixture is stirred at room temperature for about 16 h. The reaction mixture is filtered to remove pyridine hydrochloride and the filtrate is concentrated under reduced pressure. The residue is dissolved in methanol and the methacryl functional SODm is recovered by column chromatography.

Synthesis of (Meth)acrylic Copolymers Containing SODm:

Mixtures of freshly distilled methyl methacrylate and Compound 53 are dissolved in toluene (~10%w/v) and transferred to a three necked flask equipped with a stirrer, a nitrogen inlet/outlet and a reflux condenser. Azodiisobutyronitrile (1% on the weight of monomer mixture) is added and the solution is purged free of occluded air by oxygen free nitrogen. The contents are heated to 50°C and maintained at that temperature stirred under a nitrogen sweep for 48 h. The polymer solution is then slowly poured with good stirring into a large excess of methanol to recover the copolymer. The recovered copolymer can be further purified by reprecipitation from a toluene solution in methanol.

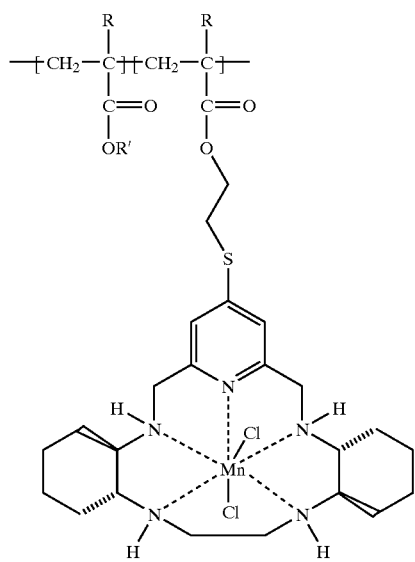

This Synthesis Results in the Following Polymer:

Example 18

Copolymerization of Hexamethylene Diamine with Compound 16

Synthesis of Poly(hexamethylene -co-SODm Sebacamide):

A mixture of hexamethylene diamine (HMD) and diamino Compound 16 is dissolved in absolute ethanol and added to a solution of sebacic acid in absolute ethanol. The mixing is accompanied by spontaneous warming. Crystallization soon occurs. After standing overnight, the salt is filtered, washed with cold absolute ethanol and air dried to constant weight. About 2% excess of HMD is used to promote a salt rich in diamine. HMD being the more volatile component, is lost during salt drying or during polycondensation.

The dried salt is heated in a suitable reactor with good stirring first to 2150°C for about an hour and then to 2700°C. After 30–60 minute heating under atomospheric pressure, the heating is continued under vacuum for about an hour. The polymer is then cooled under nitrogen and recovered.

Example 19
Copolymerization of Compound 27 with Tetramethylene Glycol and Isophthalate A three necked flask equipped with a nitrogen inlet tube extending below the surface of the reaction mixture, a mechanical stirrer, and an exit tube for nitrogen and evolved hydrogen chloride is flushed with nitrogen and charged first with a isophthaloyl chloride followed by a stoichiometric amount of a mixture of tetramethylene glycol and Compound 27 ligand. The heat of reaction would cause the isophthaloyl chloride to melt. The reaction is stirred vigorously and nitrogen is passed through the reaction mixture to drive away the hydrogen chloride (and collected in an external trap). The temperature of the reaction is then raised to 180° C. and held at that temperature for 1 hour. During the last 10 minutes of the 180° C. heating cycle, the last of the hydrogen chloride is removed by reducing the pressure to 0.5–1.0 mm. The copolymer is obtained as a white solid. Compound 27 in the polymer backbone is then complexed with manganese chloride.

Example 20

Admixture of Compound 38 with Polypropylene

Compound 38 was determined to be thermally stable up to 350°C. 0.105 g of Compound 38 was added to 4.9 g of cryoground polypropylene. The mixture was melted at 250°C and extruded into a strand and a fiber. In this manner, a polypropylene modified with a non-proteinaceous catalyst, 2% by weight, was made. The product strand was cryoground and extracted with pure water. Active Compound 38, as confirmed by both stopped-flow kinetic analysis and HPLC-UV spectroscopy, was extracted from the strand. The concentration of Compound 38 in the water was has been calculated to correspond to approximately a 10% elution of the admixed Compound 38 from the cryoground polymer. This suggests that the polypropylene would release active PACPeD catalyst at the plastic-human body tissue interface where it would serve to reduce inflammation. Other polymers which melt under 300°C and which would be suitable for use in the above process (with any appropriate temperature changes) are polyethylene, polyethylene terephthalate, and polyamides.

Example 21

In Vivo Evaluation of the Inflammatory Response to Several Surface Covalently Conjugated Polymers and Metal Samples of biomaterials, with and without PACPeD catalysts, in the form of 5–6 mm discs were implanted subcutaneously on the dorsal surface of female, 250–300 gm, Sprague Dawley rats. All disks were sterilized by three brief rinses in 70% alcohol followed by five brief rinses in sterile saline (0.9% NaCl) just prior to implantation. All biomaterials were conjugated with Compound 43. Polyurethane implants were bathed in sterile saline for one hour prior to sterilization in ethanol and implantation. Animals were initially anesthetized with 5% oxygen and 95% carbon dioxide to shave the dorsal region followed by methefane vapor administered through a nose cone during surgery. Following a sterile scrub of the surgical field, a 5 to 6 cm incision through the skin was made along the dorsal midline, a pocket in the interstitial fascia was prepared with a blunt scissors and the implant disks were inserted. The wound was closed with surgical staples. All animals were ambulatory within one hour of anesthesia. For the polyurethane and polyethylene study, each animal received an untreated control and two PACPeD treated disks at a high and low dose. For the tantalum study, each animal received a total of four disks, two controls containing to two types of linkers and two matched PACPeD treated discs. After periods of 3, 7, 14, and 28 days, animals were sacrificed with 100% carbon dioxide and the dorsal skin flap was removed and fixed in 10% neutral buffered formalin. The skin tissue was pinned upside down for photography of the implants in situ and the individual implants with surrounding tissue were excised and processed in paraffin for light microscopy. PE and PEUU implants were sectioned with the implants embedded in the paraffin block. Tantalum implants were embedded in paraffin and the paraffin block was cut in half with a low speed diamond saw. These halves were then cooled in liquid nitrogen and fractured with a cold razor blade to expose the tantalum disc. The disc was then removed from the block leaving the implant capsule intact. The tissue blocks were remelted and mounted to expose the implant capsule for microtomy. Sections were stained with hematoxylin and eosin and Gomori trichrome (Sigma, St. Louis Mo.). In addition, sections were stained immunohistochemically to identify monocyte-derived macrophages with a macrophage specific antibody, ED1 (Chemicon Inc., Temecula, Calif.). The cellular composition of the implant capsule and surrounding tissue and the matrix composition were scored visually. Measurements of foreign body giant cells number and capsule thickness were made by visual inspection and by computer based measurement of digital micrographs. All data were reported as the mean and standard deviation.

Results

Conjugated Polyethylene

Histological analysis was performed on triplicate sets of untreated control PE disks and two PACPeD treated PE disks having with either a low (0.06%) or high (1.1% (w/w)) level of PACPeD after 3, 7, 14 and 28 days of implantation. These times were selected in order to observe the acute inflammation phase and the progression to a chronic inflammation. Although differences in the healing response were observed at each time, major differences were apparent at 3 and 28 days. At 3 days, control PE disks were completely surrounded by a dense granulation tissue consisting of neutrophils and macrophages, FIG. 5A. Small blood vessels in tissue adjacent to the implant contained many adherent monocytes and leukocytes and some in various stages of transendothelial migration from blood to implant tissue. In striking contrast, the granulation tissue surrounding low and high dose PACPeD-PE, FIGS. 5B and 5C, contained very few and no neutrophils, respectively. Numerous macrophages were present on the low dose implant and labeled with ED1 antibody to suggest that they are monocyte derived. In the high dose implant capsule, the number of macrophages was greatly reduced and fibroblast like cells constituted the major cell type. In addition, blood vessels adjacent to the PACPeD-PE implants contained no adherent leukocytes or monocytes.

After 28 days equally remarkable differences were observed. In the control, foreign body giant cells (FBGCs) formed a layer between the implant and the implant capsule tissue, FIG. 6A, to indicate that chronic inflammation was underway. FBGCs also filled the many scratches that formed the rough PE surface. The implant capsule tissue consisted of layered fibroblasts, some ED1 positive macrophages, a few neutrophils and collagen matrix. For the low level PACPeD disks, the capsule had a marked reduction in FBGCs on the surface and in number of cells in the capsule in comparison to control, FIG. 6B. With the high PACPeD-PE disks, FBGCs were rarely observed, FIG. 6C. The number of FBGCs observed in two independent sections per disk for a total of six counts per treatment group were averaged and revealed a statistically significant decrease in FBGC with PACPeD-PE over control, FIG. 7. In addition, the thickness of the implant capsule as measured from the same sections was significantly reduced in comparison to untreated control PE.

Polyurethane

Histological analysis was performed on triplicate sets of untreated control PEUU disks and two PACPeD treated PE disks having with either a low (0.6%) or high (3.0% w/w) level of PACPeD after 3, 7, 14 and 28 days of implantation. Although, PEUU is well known to be less inflammatory than polyethylene, the effect of surface bound PACPeD mimic was obvious and similar to that observed for PE disks at 3 and 28 days. At 3 days, implant capsules of control PEUU disks contained neutrophils and ED1 positive macrophages although their numbers were estimated to be two orders of magnitude less than PE control. Capsules surrounding the low level PACPeD-PEUU implants had a markedly reduced but detectable number of neutrophils with macrophages and fibroblast being predominant. As was observed for the PACPeD-PE implants, capsule tissue around the high dose PACPeD-PEUU disks contained no observable neutrophils and a reduced number of macrophages.

At 28 days, implant capsules around the PEUU control disks had a layer of adherent FBGCs and layers of fibroblasts, ED1 positive macrophages and collagen matrix, FIG. 8A. With the low level PACPeD, FIG. 8B, the number of FBGCs was reduced although the implant capsule contained fibroblast and fewer ED1 positive macrophages and had a thickness similar to the control. The high level PACPeD-PEUU disk capsule had very few FBGCs and the capsule thickness was estimated to be one half of the control capsule, FIG. 8C.

It is well known that PEUU is susceptible to biodegradation in vivo leading to the formation of surface pits and cracks. To monitor this effect in control and functionalized disks, scanning electron microscopy, SEM, was used to examine non-implanted disks and 28 day implanted disks, FIGS. 1–3. The non-implanted PEUU film showed a smooth surface with no cracks or pitted areas, FIG. 1. The implanted control PEUU sample after 28 days contained large, multiple cracks and areas where the surface had been eroded, FIG. 2. The implanted PACPeD-PEUU sample showed no obvious differences compared to the non-implanted control, FIG. 3.

Hence, in addition to inhibiting both acute and chronic inflammatory responses, PACPeD linked to PEUU surface inhibited surface degradation observed at 28 days.

Tantalum

Tantalum disks treated with either the silane linker or the PACPeD and silane linker were implanted for 3 and 28 days. The healing response was similar to that seen for treated and untreated polymers. After 3 days, a neutrophil rich granulation tissue enveloped the Ta-silane linker treated disk, FIG. 9A. With PACPeD treatment, the neutrophils were absent with macrophages and matrix making up the bulk of the implant bed, FIG. 9B. After 28 days the control disks had a more pronounced implant capsule which was reduced in thickness at PACPeD treated disks, FIG. 10.

Example 22

In Vivo Evaluation of the Inflammatory Response to Polypropylene Admixed with Compound 54

Sample Fiber Preparation

The polypropylene implants for the rat studies were made in a fiber form. After a dry blend was made in the cryogrinder, the mixture was subjected to twin screw mixing in a DACA melt mixer. 3 gms of PP and 60 mg of Compound 54 (more lipophilic than Compound 38) was used. The impact time in the cryogrinder was 5 minutes. The melt mixing chamber was held at 250° C. The mixing time was 5 minutes with the rpm being 50. No appreciable differences in the torque was seen between the control and the Compound 54 incorporated PP.

A 50 denier fiber with 30% of elongation to break was the target. The parameters in the DACA melt spin equipment were the following:

| | |
|---|---|
| Diameter of the spinneret: | 0.5 mm |
| Piston speed: | 9.82 mm/min |
| Spin speed of the main godet: | 1 2.85 RPM |
| Draw ratio: | 7 |
| Temperature of the plate: | 125° C. |
| Temperature of the barrel: | 250° C. |

The extruded strands from the melt blending were cut into little pieces which fed into the barrel more easily. The melt spinning was done at 250° C. Because the medical grade polymer degrades after 20 minutes at high temperature we had to use a flow rate of 0.35 g/min (the amount of PP in the barrel is 7 g).

Implantation Procedure

Polypropylene fibers, with and without Compound 54 mimic, were implanted subdermally in 250–300 gram female rats. The polypropylene fiber implant consisted of a 15 to 20 cm length that was wrapped and tied into a figure eight shape measuring about 2 cm by 0.5. Animals were anesthetized with a mixture of 50/10 mg/kg Ketamine/Xylazine by intraperitoneal injection. The right flank was shaved and scrubbed with surgical scrub. A small 1.5 cm long incision was made over the right haunch. A subcutaneous pocket was made and the appropriate piece of material was placed in the pocket. The implants were briefly rinsed in 70% alcohol and rinsed with 2 dips in sterile saline prior to insertion into the tissue pocket. The incision was closed with a stainless steel staple. The rats were returned to their cages for recovery.

The animal were removed from their cages after 21 days post implant and sacrificed by $CO_2$ inhalation. The implants were removed with overlying skin attached and fixed in Streck STF fixative overnight at 4–8° C. The explants were cut into two or three pieces to expose polymer cross-sections and were processed for embedding in paraffin. Routine sections were cut and stained with hematoxylin and eosin or Masson Trichrome and immunostained with an antibody specific of macrophages, EDI (Chemicon Inc.).

In Vivo Response to Implanted Compound 54 Containing Polypropylene

Gross histology examination of control PP fibers attached to the under surface of the skin flap explants evidenced the fibers to be surrounded by a relatively thick matrix of collagen. The position and overall shape of the implant were discernible but individual fibers could not be seen. Histological cross-sections confirmed a relatively thick wrap of connective tissue. In addition to matrix, higher magnification views reveal an intense inflammatory reaction at each fiber. Control fibers cover with one to two layers of cells which appear to be macrophages based on positive immunohistochemical staining with the rate macrophage marker, ED1, FIG. 4A. In addition, foreign body giant cells were also present on all control fibers. These observations are consistent with the expected chronic inflammatory response.

Compound 54 containing PP fibers exhibited a different response. Gross examination reveal an implant site in which the individual fibers were clearly visible. It was obvious that the fibrotic and cellular response which covered the control PP fibers was reduced. Histologically, a reduced fibrotic response was apparent, with only a thin wrap of matrix being observed in Trichrome stained sections. In addition, the inflammatory response at individual SODm containing fibers was markedly reduced. Typically, modified fibers were covered by a thin layer of matrix and few fibroblasts and only partial coverage by macrophages, FIG. 4B. Foreign body giant cells were seldom observed on modified fibers. A count of foreign body giant cells per fiber were performed on control and Compound 54 containing PP fibers. Control fiber FBGC counts were 2.63±1.34 per fiber, n=20 while modified fibers had 1.28±1.04 FBGC per fiber, n=40.

Despite the striking difference in the inflammatory response, the number or density of fine capillaries appeared to be very similar between the control and modified fibers. This was assessed visually in tissues spaces between the fibers within the hank and the tissue surrounding the hank implant.

Example 23

Luminol Analysis of Modified Polymers and Metals to Determine Superoxide Dismutating Activity The Michelson assay uses xanthine oxidase and hypoxanthine to produce superoxide radical anion in situ in a steady-state manner. If not eliminated from the solution with an antioxidant, superoxide then reacts with luminol to produce a measurable amount of light. This reaction is stoichiometric and provides a linear response under pseudo first-order reaction conditions (i.e. [luminol]>>[O2-]). The light emission is measured over several minutes 9as the enzyme-substrate solution produces superoxide at a specific rate) and the integration of units over that time is reported. It should then be possible to take samples of antioxidants and determine the presence of catalyst, the rate of dismutation, and/or whether the compound is actually catalytic or stoichiometric in its ability to dismute superoxide.

Using this method, we have taken sample films[1/] p. 74. (lactide/glycolide polymer) doped with Compound 38, a known catalyst for the dismutation of superoxide and the parent compound in our current SAR, and analyzed them on a Turner Designs TD-20/20 Luminometer.[2/] unpublished results. 400 uL of a 0.05 unit/mL xanthine oxidase, 0.1 mM EDTA and 0.1 mM Luminol in 0.1 M glycine buffer at pH 9; 200 uL of a 250 uM xanthine solution are added via autoinjector to a one 2 square millimeter sample of each film in the sample well. The sample is then run on the Luminometer, and the reading translated into an integration. Samples of PEUU surface covalently conjugated with Compound 43 were tested and found to possess superoxide dismutating activity.

[1/] Michelson, A. M. In Handbook of Methods of Oxygen Radical Research, Greenwald, R. A., Ed., CRC:Boca Raton, 1989;

[2/] Gary W. Franklin; Monsanto Notebook, p. 6136376,

Example 24

Stopped-Flow Kinetic Analysis

Stopped-flow kinetic analysis has been utilized to determine whether a compound can catalyze the dismutation of superoxide (Riley, D. P., Rivers, W. J. and Weiss, R. H., "Stopped-Flow Kinetic Analysis for Monitoring Superoxide Decay in Aqueous Systems," Anal. Biochem, 196: 344–349 1991). For the attainment of consistent and accurate measurements all reagents were biologically clean and metal-free. To achieve this, all buffers (Calbiochem) were biological grade, metal-free buffers and were handled with utensils which had been washed first with 0.1N HCl, followed by purified water, followed by a rinse in a $10^{-4}$ M EDTA bath at pH 8, followed by a rinse with purified water and dried at 65. degree. C. for several hours. Dry DMSO solutions of potassium superoxide (Aldrich) were prepared under a dry, inert atmosphere of argon in a Vacuum Atmospheres dry glovebox using dried glassware. The DMSO solutions were prepared immediately before every stopped-flow experiment. A mortar and pestle were used to grind the yellow solid potassium superoxide (.about.100 mg). The powder was then ground with a few drops of DMSO and the slurry transferred to a flask containing an additional 25 ml of DMSO. The resultant slurry was stirred for ½ h and then filtered. This procedure gave reproducibly .about.2 mM concentrations of superoxide in DMSO. These solutions were transferred to a glovebag under nitrogen in sealed vials prior to loading the syringe under nitrogen. It should be noted that the DMSO/superoxide solutions are extremely sensitive to water, heat, air, and extraneous metals. A fresh, pure solution has a very slight yellowish tint.

Water for buffer solutions was delivered from an in-house deionized water system to a Barnstead Nanopure Ultrapure Series 550 water system and then double distilled, first from alkaline potassium permanganate and then from a dilute EDTA solution. For example, a solution containing 1.0 g of potassium permanganate, 2 liters of water and additional sodium hydroxide necessary to bring the pH to 9.0 were added to a 2-liter flask fitted with a solvent distillation head. This distillation will oxidize any trace of organic compounds in the water. The final distillation was carried out under nitrogen in a 2.5-liter flask containing 1500 ml of water from the first still and $1.0 \times 10^{-6}$ M EDTA. This step will remove remaining trace metals from the ultrapure water. To prevent EDTA mist from volatilizing over the reflux arm to the still head, the 40-cm vertical arm was packed with glass beads and wrapped with insulation. This system produces deoxygenated water that can be measured to have a conductivity of less than 2.0 nanomhos/cm².

The stopped-flow spectrometer system was designed and manufactured by Kinetic Instruments Inc. (Ann Arbor, Mich.) and was interfaced to a MAC IICX personal computer. The software for the stopped-flow analysis was provided by Kinetics Instrument Inc. and was written in Quick-Basic with MacAdios drivers. Typical injector volumes (0.10 ml of buffer and 0.006 ml of DMSO) were calibrated so that a large excess of water over the DMSO solution were mixed together. The actual ratio was approximately 19/1 so that the initial concentration of superoxide in the aqueous solution was in the range 60–120:M. Since the published extinction coefficient of superoxide in $H_2O$ at 245 nm is .about.$2250M^{-1}$ $cm^{-1}$ (1), an initial absorbance value of approximately 0.3–0.5 would be expected for a 2-cm path length cell, and this was observed experimentally. Aqueous solutions to be mixed with the DMSO solution of superoxide were prepared using 80 mM concentrations of the Hepes buffer, pH 8.1 (free acid+Na form). One of the reservoir syringes was filled with 5 ml of the DMSO solution while the other was filled with 5 ml of the aqueous buffer solution. The entire injection block, mixer, and spectrometer cell were immersed in a thermostated circulating water bath with a temperature of 21EC±0.5EC. Prior to initiating data collection for a superoxide decay, a baseline average was obtained by injecting several shots of the buffer and DMSO solutions into the mixing chamber. These shots were averaged and stored as the baseline. The first shots to be collected during a series of runs were with aqueous solutions that did not contain catalyst. This assures that each series of trials were free of contamination capable of generating first-order superoxide decay profiles. If the decays observed for several shots of the buffer solution were second-order, solutions of manganese(II) complexes could be utilized. In general, the potential SOD catalyst was screened over a wide range of concentrations. Since the initial concentration of superoxide upon mixing the DMSO with the aqueous buffer was about 1.2 times $10^{-4}$ M, we wanted to use a manganese (II) complex concentration that was at least 20 times less than the substrate superoxide. Consequently, we generally screened compounds for superoxide dismutating activity using concentrations ranging from $5 \times 10^{-7}$ to $8 \times 10^{-6}$ M. Data acquired from the experiment was imported into a suitable math program (e.g., Cricket Graph) so that standard kinetic data analyses could be performed. Catalytic rate constants for dismutation of superoxide by manganese(II) complexes were determined from linear plots of observed rate constants ($k_{obs}$) versus the concentration of the manganese(II) complexes. $k_{obs}$ values were obtained from linear plots of ln absorbance at 245 nm versus time for the dismutation of superoxide by the manganese(II) complexes.

Example 25

Use of Hyaluronic Acid Esters Surface Covalently Conjugated with Compound 43 to Produce a Neural Growth Guide Channel Device A guide channel with a composite thread/polymeric matrix structure wherein the thread comprises HYAFF 11 (total benzyl ester of HY, 100% esterified) and the matrix is composed of HYAFF 11p75 (benzyl ester of HY 75% esterified) is obtained by the following procedure.

A. Preparation of Esters

Preparation of the Benzyl Ester of Hyaluronic Acid (HY): 3 g of the potassium salt of HY with a molecular weight of 162,000 are suspended in 200 ml of dimethylsulfoxide; 120 mg of tetrabutylammonium iodide and 2.4 g of benzyl bromide are added. The suspension is kept in agitation for 48 hours at 30EC. The resulting mixture is slowly poured into 1,000 ml of ethyl acetate under constant agitation. A precipitate is formed which is filtered and washed four times with 150 ml of ethyl acetate and finally vacuum dried for twenty four hours at 30EC. 3.1 g of the benzyl ester product in the title are obtained. Quantitative determination of the ester groups is carried out according to the method described on pages 169–172 of Siggia S. and Hanna J. G. "Quantitative organic Analysis Via Functional Groups," 4th Edition, John Wiley and Sons.

Preparation of the (Partial) Benzyl Ester of Hyaluronic Acid (HY)—75% Esterified Carboxylic Groups,—25% Salified Carboxylic Groups (Na): 12.4 g of HY tetrabutylammonium salt with a molecular weight of 170,000, corresponding to 20 m.Eq. of a monomeric unit, are solubilized in 620 ml of dimethylsulfoxide at 25EC. 120 mg of tetrabutylammonium iodide and 15.0 m.Eq. of benzyl bromide are added and the resulting solution is kept at a temperature of 30E for 12 hours. A solution containing 62 ml of water and 9 g of sodium chloride is added and the resulting mixture is slowly poured into 3,500 ml of acetone under constant agitation. A precipitate is formed which is filtered and washed three times with 500 ml of acetone/water, 5:1, and three times with acetone, and finally vacuum dried for eight hours at 30EC.

The product is then dissolved in 550 ml of water containing 1% sodium chloride and the solution is slowly poured into 3,000 ml of acetone under constant agitation. A precipitate is formed which is filtered and washed twice with 500 ml of acetone/water, 5:1, three times with 500 ml of acetone, and finally vacuum dried for 24 hours at 30EC. 7.9 g of the partial propyl ester compound in the title are obtained. Quantitative determination of the ester groups is carried out using the method of R. H. Cundiff and P. C. Markunas Anal. Chem. 33, 1028–1030, (1961).

The HYAFP esters are then surface covalently conjugated with Compound 43 as in Example 14.

B. Production of the Device

A thread of total HYAFP 11 esters, 250 denier, with a minimum tensile strength at break of 1.5 gr/denier and 19% elongation is entwined around an electropolished AISI 316 steel bar with an outer diameter of 1.5 mm, which is the desired inner diameter of the composite guide channel. The woven product is obtained using a machine with 16 loaders per operative part.

A typical tube-weaving system system (like the one shown in U.S. Pat. No. 5,879,359) comprising the steel bar with a threaded tube fitted over it is placed in position. The apparatus is rotated at a speed of 115 rpm. A quantity of HYAFF 11p75/dimethylsulfoxide solution at a concentration of 135 mg/ml is spread over the rotating system. The excess solution is removed with a spatula, and the system is removed from the apparatus and immersed in absolute ethanol. After coagulation, the guide channel is removed from the steel bar and cut to size.

The channel made by the above technique is 20 mm long, 300.mu.m thick, has an internal diameter of 1.5 mm, and has a weight of 40 mg, equal to 20 mg/cm.

Example 26

Use of Metals Surface Covalently Conjugated with Compound 43 to Produce a Stent

A stent may be formed from surgical stainless steel alloy wire which is bent into a zigzag pattern, and then wound around a central axis in a helical pattern. Referring now more particularly to FIGS. 11–17, there is illustrated in FIG. 11 a midpoint in the construction of the stent which comprises the preferred embodiment of the present invention. FIG. 11 shows a wire bent into an elongated zigzag pattern 5 having a plurality of substantially straight wire sections 9–15 of various lengths separated by a plurality of bends 8. The wire has first and second ends designated as 6 and 7, respectively. Zigzag pattern 5 is preferably formed from a single strand of stainless steel wire having a diameter in the range of 0.005 to 0.025 inch.

FIG. 13 shows a completed stent 30. The construction of the stent is completed by helically winding elongated zigzag pattern 5 about a central axis 31. Zigzag pattern 5 is wound in such a way that a majority of the bends 8 are distributed in a helix along the length of the stent 30. There are preferably about twelve interconnected bends in each revolution of the helix, or six adjacent bends of the zigzag pattern in each revolution. The construction of stent 30 is completed by interconnecting adjacent bends of the helix with a filament 32, preferably a nylon monofilament suture. Filament 32 acts as a limit means to prevent the stent from further radial expansion beyond the tubular shape shown in FIGS. 13 and 14. The tubular shape has a central axis 31, a first end 33 and a second end 35. Each end of stent 30 is defined by a plurality of end bends 36, which are themselves interconnected with a filament 34. Other embodiments of the present invention are contemplated in which the end bends 36 are left unconnected in the finished stent. FIG. 14 shows an end view of stent 30 further revealing its tubular shape. FIG. 15 shows stent 30 of FIG. 13 when radially compressed about central axis 31 such that the straight wire sections and the bends are tightly packed around central axis 31.

Referring back to FIG. 11, the zigzag pattern is made up of straight wire sections having various lengths which are distributed in a certain pattern to better facilitate the helical structure of the final stent construction. For instance, in one embodiment, end wire sections 9 could be made to a length of 9 mm followed by two wire sections 11 each being 11 mm in length. Wire sections 11 are followed by two 13 mm wire sections 13, which are in turn followed by two wire sections 15 having a length of 15 mm. Sections 15 are followed by a single wire section 17 having a length of 17 mm. These gradually increasing wire sections at either end of the zigzag pattern enable the final stent to have well defined square ends. In other words, the gradually increasing length wire sections on either end of the zigzag pattern enable the final stent to have a tubular shape in which the ends of the tube are substantially perpendicular to the central axis of the stent. Following wire section 17, there are a plurality of alternating length sections 13 and 15. Short sections 13 being 13 mm in length and long sections 15 being 15 mm in length. This alternating sequence is continued for whatever distance is desired to correspond to the desired length of the final stent. The difference in length between the short sections 13 and long sections 15 is primarily dependent upon the desired slope of the helix (see .beta. in FIG. 16) and the desired number of bends in each revolution of the helix.

FIG. 16 is an enlarged view of a portion of the stent shown in FIG. 13. The body of stent 30 includes a series of alternating short and long sections, 13 and 15 respectively. A bend 8 connects each pair of short and long sections 13 and 15. Each bend 8 defines an angle 2∀ which can be bisected by a bisector 40. These short and long sections are arranged in such a way that bisector 40 is parallel to the central axis 31 of the stent. This allows the stent to be radially compressed without unnecessary distortion.

FIG. 12 shows an enlarged view of one end of the zigzag pattern. End 6 of the wire is bent to form a closed eye portion 20. Eye 20 is preferably kept closed by the application of the small amount of solder to the end 6 of the wire after it has been bent into a small loop. Each of the bends 8 of the zigzag pattern are bent to include a small eye portion designated as 21 and 23 in FIG. 12, respectively. Eye 21 includes a small amount of solder 22 which renders eye 21 closed. Eye 23 includes no solder and is left open. The bends 8 which define the helix can be either in the form of a closed eye, as in eye 21, or open as in eye 23.

After forming the stent, the stent is then modified by surface covalent conjugation with a silyl linker, as in Example 13. By treatment with acid mixtures well known in the art, the stainless steel surface can be oxidized to display a layer of hydroxide. The conjugation then proceeds as in Example 13.

Example 27

Use of Surface Covalently Conjugated Pet Fibers to Produce a Woven Vascular Graft PET fibers are surface covalently conjugated with Compound 43 according to Example 7. The vascular graft fabric is formed from single ply, 50 denier, 47 filament (1/50/47) pretexturized, high shrinkage (in excess of approximately 15%), polyethylene terephthalate (PET) yarns woven in a plain weave pattern with 83 ends/inch and 132 picks/inch (prior to processing). The vascular graft fabric, prior to processing, has a double wall size of less than 0.02 inches and preferably has a double wall thickness of about 0.01 inches. The yarns may be twisted prior to weaving and a graft with 8 twists per inch has provided acceptable properties. Other weave patterns, yarn sizes (including microdenier) and thread counts also are contemplated so long as the resulting fabric has the desired thinness, radial compliance and resistance to long term radial dilation and longitudinal expansion.

The woven fabric is washed at an appropriate temperature, such as between 60E–90EC, and then is steam set over a mandrel to provide the desired tubular configuration. The graft is then dried in an oven or in a conventional dryer at approximately 150EF. Any of the washing, steaming and drying temperatures may be adjusted to affect the amount of shrinkage of the fabric yarns. In this manner, the prosthetic is radially compliant to the extent necessary for the ends of the graft to conform to the slightly larger anchoring sections of the aorta, but resists radial dilation that otherwise could lead to rupture of the aneurysm and axial extension that could block the entrance to an iliac artery. Radial dilation is considered to occur when a graft expands a further 5% after radial compliance. The 5% window allows for slight radial expansion due to the inherent stretch in the yarn of the fabric.

The thin walled, woven vascular graft fabric is be formed into a tubular configuration and collapsed into a reduced profile for percutaneous delivery of the prosthetic to the delivery site. The implant is sufficiently resilient so that it will revert back to its normal, expanded shape upon deployment either naturally or under the influence of resilient anchors that secure the implant to the vessel wall, and or, alternatively, struts that prevent compression and twisting of the implant. The thin wall structure allows small delivery instruments (18 Fr or smaller) to be employed when the graft is percutaneously placed. The fine wall thickness also is believed to facilitate the healing process. The graft, when used for the repair of an abdominal aortic aneurysm, may be provided in a variety of outer diameters and lengths to match the normal range of aortic dimensions.

The biologically compatible prosthetic fabric encourages tissue ingrowth and the formation of a neointima lining along the interior surface of the graft, preventing clotting of blood within the lumen of the prosthetic which could occlude the graft. The graft has sufficient strength to maintain the patency of the vessel lumen and sufficient burst resistance to conduct blood flow at the pressures encountered in the aorta without rupturing. The graft is usually preclotted with either the patient's own blood or by coating the fabric with an impervious material such as albumin, collagen or gelatin to prevent hemorrhaging as blood initially flows through the graft. Although a constant diameter graft is preferred, a varying dimensioned prosthetic also is contemplated. The graft is also usually provided with one or more radiopaque stripes to facilitate fluoroscopic or X-ray observation of the graft.

Example 28

Use of Copolymerized Polyurethane to to Insulate Cardiac Simulator Lead Wire

A die-clad composite conductor is made with a highly conducting core and a cladding layer. Copper and copper alloys are particularly suitable for the core material of the composite conductor. Pure copper is preferable, but alloys such as Cu0.15Zr, Cu4Ti, Cu2Be, Cu1.7Be, Cu0.7Be, Cu28Zn, Cu37Zn, Cu6Sn, Cu8Sn and Cu2Fe may be used. A metal selected from the group consisting of tantalum, titanium, zirconium, niobium, titanium-base alloys, platinum, platinum-iridium alloys, platinum-palladium alloys and platinum-rhodium alloys is applied as a cladding layer to the conducting core by drawing through a die. The cladding layer thickness is between 0.0025 and 0.035 mm, while the core diameter is between 0.04 and 0.03 mm. Although a single strand conductor could be used, the risks of breakage are reduced and the conductivity is increased without going beyond the above described preferred ranges for core diameter and cladding if a stranded conductor is used. Furthermore a stranded conductor provides increased flexibility. Thus, it is preferred that the conductor in the cable be composed of two or more thinner strands twisted together.

The clad wire conductor is enclosed in an elastic covering tube, which consists of a synthetic elastomer such as flexible polyurethane. A polyurethane which has been copolymerized with a PACPeD catalyst, such as the polyurethane of Example 12, should be used. It is sufficiently elastic and flexible to make possible its introduction into the heart chamber simply by being carried along through the blood stream. The biocompatability of the clad wire conductor of the cable is improved by oxidizing the surface of the clad wire and covalently conjugating a PACPeD catalyst to the wire, as in Example 13.

What is claimed is:

1. A modified biopolymer comprising a biopolymer chosen from the group consisting of chitin, chitosan, cellulose, methyl cellulose, hyaluronic acid, keratin, fibroin, collagen, elastin, and saccharide polymers attached to at least one non-proteinaceous catalyst capable of dismutating superoxide in the biological system or precursor ligand thereof, wherein the non-proteinaceous catalyst capable of dismutating superoxide is chosen from the group consisting of:

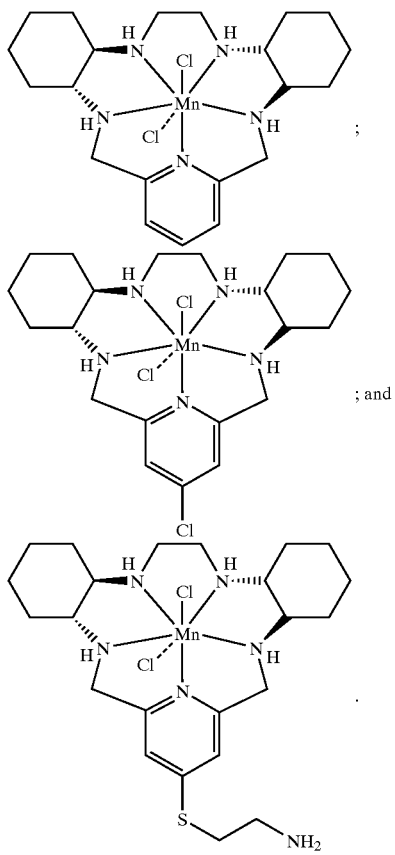

2. Modified hyaluronic acid prepared by reaction of hyaluronic acid with a non-proteinaceous catalyst capable of dismutating superoxide having the structure:

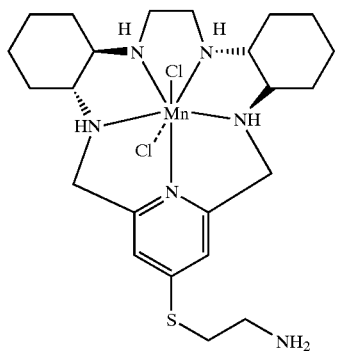

or a precursor ligand thereof under conditions appropriate to covalently attach the non-proteinaceous catalyst capable of dismutating superoxide to the hyaluronic acid.

3. The modified biopolymer of claim 1, wherein the biopolymer is hyaluronic acid.

4. A modified biopolymer comprising hyaluronic acid attached to at least one catalyst having the structure:

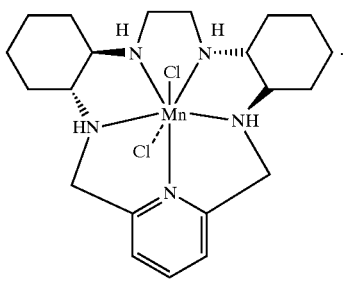

5. A modified biopolymer comprising hyaluronic acid attached to at least one catalyst having the structure:

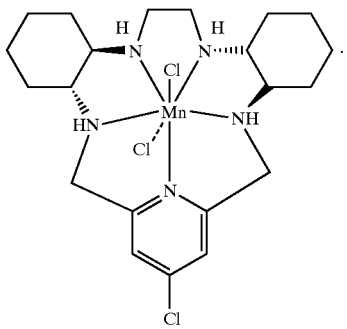

6. A modified biopolymer comprising hyaluronic acid attached to at least one catalyst having the structure:

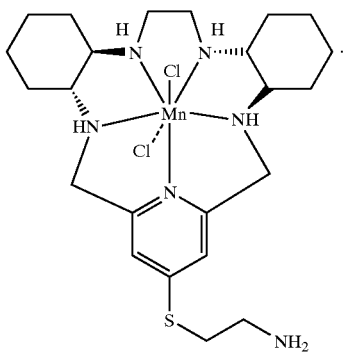

* * * * *